US006960635B2

(12) United States Patent
Stevens et al.

(10) Patent No.: US 6,960,635 B2
(45) Date of Patent: Nov. 1, 2005

(54) ISOTACTIC PROPYLENE COPOLYMERS, THEIR PREPARATION AND USE

(75) Inventors: James C. Stevens, Richmond, TX (US); Daniel D. Vanderlende, Sugarland, TX (US)

(73) Assignee: Dow Global Technologies Inc., Midland, MI (US)

( * ) Notice: Subject to any disclaimer, the term of this patent is extended or adjusted under 35 U.S.C. 154(b) by 105 days.

(21) Appl. No.: 10/139,786

(22) Filed: May 5, 2002

(65) Prior Publication Data

US 2003/0204017 A1 Oct. 30, 2003

Related U.S. Application Data

(60) Provisional application No. 60/338,881, filed on Nov. 6, 2001.

(51) Int. Cl.[7] .................................................. C08F 4/42
(52) U.S. Cl. ....................... 526/161; 526/351; 526/348; 526/160; 526/943
(58) Field of Search ................................ 526/351, 348, 526/160, 943, 161

(56) References Cited

U.S. PATENT DOCUMENTS

| | | | |
|---|---|---|---|
| 3,485,706 A | 12/1969 | Evans ........................... 161/72 |
| 3,520,861 A | 7/1970 | Thomson et al. ........... 260/88.1 |
| 4,076,698 A | 2/1978 | Anderson et al. ......... 526/348.6 |
| 4,322,027 A | 3/1982 | Reba ............................ 226/97 |
| 4,330,646 A | 5/1982 | Sakurai et al. ............... 526/116 |
| 4,413,110 A | 11/1983 | Kavesh et al. ............ 526/348.1 |
| 4,430,563 A | 2/1984 | Harrington ................... 235/494 |
| 4,542,199 A | 9/1985 | Kaminsky et al. ........... 526/160 |
| 4,544,762 A | 10/1985 | Kaminsky et al. ........... 556/179 |
| 4,599,392 A | 7/1986 | McKinney et al. ....... 526/318.6 |
| 4,612,300 A | 9/1986 | Coleman, III ............... 502/113 |
| 4,663,220 A | 5/1987 | Wisneski et al. ........... 428/221 |
| 4,668,566 A | 5/1987 | Braun ......................... 428/286 |
| 4,668,753 A | 5/1987 | Kashiwa et al. ............. 526/348 |
| 4,874,880 A | 10/1989 | Miya et al. ................... 556/53 |
| 4,960,878 A | 10/1990 | Crapo et al. ................. 556/179 |
| 4,988,781 A | 1/1991 | McKinney et al. ........... 526/68 |
| 5,015,749 A | 5/1991 | Schmidt et al. .............. 556/179 |
| 5,041,583 A | 8/1991 | Sangokoya ................. 556/179 |
| 5,041,584 A | 8/1991 | Crapo et al. ................. 556/179 |
| 5,041,585 A | 8/1991 | Deavenport et al. ........ 556/179 |
| 5,044,438 A | 9/1991 | Young ......................... 166/250 |
| 5,057,475 A | 10/1991 | Canich et al. ............... 502/104 |
| 5,064,802 A | 11/1991 | Stevens et al. .............. 502/155 |
| 5,093,415 A | 3/1992 | Brady, III et al. ............ 525/53 |
| 5,096,867 A | 3/1992 | Canich ........................ 502/103 |
| 5,132,380 A | 7/1992 | Stevens et al. .............. 526/126 |
| 5,134,209 A | 7/1992 | Job et al. ..................... 526/141 |
| 5,153,157 A | 10/1992 | Hlatky et al. ................ 502/117 |
| 5,198,401 A | 3/1993 | Turner et al. ................ 502/155 |
| 5,218,071 A | 6/1993 | Tsutsui et al. ............... 526/348 |
| 5,229,478 A | 7/1993 | Floyd et al. ................. 526/160 |
| 5,272,236 A | 12/1993 | Lai et al. ................... 526/348.5 |
| 5,278,272 A | 1/1994 | Lai et al. ................... 526/348.5 |
| 5,296,433 A | 3/1994 | Siedle et al. ................ 502/117 |
| 5,322,728 A | 6/1994 | Davey et al. ............... 428/296 |
| 5,324,800 A | 6/1994 | Welborn, Jr. et al. ....... 526/160 |
| 5,350,723 A | 9/1994 | Neithamer et al. .......... 502/104 |
| 5,358,792 A | 10/1994 | Mehta et al. ............... 428/516 |
| 5,380,810 A | 1/1995 | Lai et al. ..................... 526/352 |
| 5,384,373 A | 1/1995 | McKinney et al. .......... 526/212 |
| 5,408,017 A | 4/1995 | Turner et al. ................ 526/134 |
| 5,412,020 A | 5/1995 | Yamamoto et al. ......... 524/505 |
| 5,427,991 A | 6/1995 | Turner ......................... 502/103 |
| 5,472,775 A | 12/1995 | Obijeski et al. ............. 428/220 |
| 5,504,049 A | 4/1996 | Crowther et al. ............ 502/117 |
| 5,504,172 A * | 4/1996 | Imuta et al. |
| 5,516,866 A | 5/1996 | Resconi et al. ........... 526/348.6 |
| 5,556,928 A * | 9/1996 | Devore et al. |
| 5,599,761 A | 2/1997 | Turner ......................... 502/152 |
| 5,616,664 A | 4/1997 | Timmers et al. ............. 526/127 |
| 5,621,046 A | 4/1997 | Iwanami et al. ............. 525/240 |
| 5,621,127 A | 4/1997 | Langhauser et al. ......... 556/11 |
| 5,625,087 A | 4/1997 | Devore et al. ............... 556/468 |
| 5,637,660 A | 6/1997 | Nagy et al. .................. 526/160 |
| 5,645,542 A | 7/1997 | Anjur et al. ................. 604/368 |
| 5,656,374 A | 8/1997 | Marzola et al. ............. 428/402 |
| 5,685,128 A | 11/1997 | Chum et al. ................... 53/441 |
| 5,686,533 A | 11/1997 | Gahleitner et al. .......... 525/240 |
| 5,703,187 A | 12/1997 | Timmers ..................... 526/282 |
| 5,703,257 A | 12/1997 | Rosen et al. .................... 556/7 |
| 5,710,224 A | 1/1998 | Alt et al. ..................... 526/160 |
| 5,721,185 A | 2/1998 | LaPointe et al. ............ 502/117 |

(Continued)

FOREIGN PATENT DOCUMENTS

| | | | |
|---|---|---|---|
| WO | 00/59961 A1 | 10/2000 | .......... C08F/10/02 |
| WO | 01/74910 A2 | 10/2001 | .......... C08F/4/00 |
| WO | 02/38628 A2 | 5/2002 | .......... C08F/10/00 |

OTHER PUBLICATIONS

News Release, Japan Polychem Launches WINTEC Metallocene–Based PP Random Copolymer, Oct. 25, 2001, http://www.m-kagaku.co.jp/english/rel/2001/102501.htm.

Primary Examiner—Ling-Siu Choi
(74) Attorney, Agent, or Firm—Whyte Hirschboeck Dudek SC

(57) ABSTRACT

Unique copolymers comprising propylene, ethylene and/or one or more unsaturated comonomers are characterized as having: at least one, preferably more than one, of the following properties: (i) $^{13}C$ NMR peaks corresponding to a regio-error at about 14.6 and about 15.7 ppm, the peaks of about equal intensity, (ii) a B-value greater than about 1.4 when the comonomer content of the copolymer is at least about 3 wt %, (iii) a skewness index, $S_{ix}$, greater than about −1.20, (iv) a DSC curve with a $T_{me}$ that remains essentially the same and a $T_{max}$ that decreases as the amount of comonomer in the copolymer is increased, and (v) an X-ray diffraction pattern that reports more gamma-form crystals than a comparable copolymer prepared with a Ziegler-Natta catalyst. These polypropylene polymers are made using a nonmetallocene, metal-centered, heteroaryl ligand catalyst. These polymers can be blended with other polymers, and are useful in the manufacture of films, sheets, foams, fibers and molded articles.

29 Claims, 30 Drawing Sheets

U.S. PATENT DOCUMENTS

| | | | |
|---|---|---|---|
| 5,728,855 A | 3/1998 | Smith et al. | 556/179 |
| 5,731,253 A | 3/1998 | Sangokoya | 502/102 |
| 5,747,621 A | 5/1998 | Resconi et al. | 526/351 |
| 5,753,773 A | 5/1998 | Langhauser et al. | 525/323 |
| 5,760,141 A | 6/1998 | Watanabe et al. | 525/323 |
| 5,767,208 A | 6/1998 | Turner et al. | 526/160 |
| 5,869,575 A | 2/1999 | Kolthammer et al. | 525/240 |
| 5,874,505 A | 2/1999 | Saito et al. | 525/240 |
| 5,883,188 A | 3/1999 | Hwang et al. | 525/71 |
| 5,883,204 A | 3/1999 | Spencer et al. | 526/134 |
| 5,891,976 A | 4/1999 | Costa et al. | 526/351 |
| 5,907,021 A | 5/1999 | Turner et al. | 526/160 |
| 5,910,224 A | 6/1999 | Morman | 156/178 |
| 5,919,983 A | 7/1999 | Rosen et al. | 568/3 |
| 5,922,822 A | 7/1999 | Wilson et al. | 526/288 |
| 5,929,147 A | 7/1999 | Pierick et al. | 524/99 |
| 5,945,496 A | 8/1999 | Resconi et al. | 526/351 |
| 5,962,714 A | 10/1999 | McCullough et al. | 556/11 |
| 5,965,677 A | 10/1999 | Stephan et al. | 526/129 |
| 5,965,756 A | 10/1999 | McAdon et al. | 556/11 |
| 5,972,822 A * | 10/1999 | Timmers et al. | |
| 5,994,482 A | 11/1999 | Georgellis et al. | 526/65 |
| 6,001,933 A | 12/1999 | Tsuruoka et al. | 525/232 |
| 6,005,049 A | 12/1999 | Rebhan et al. | 525/53 |
| 6,013,819 A | 1/2000 | Stevens et al. | 556/11 |
| 6,015,868 A | 1/2000 | Nickias et al. | 526/127 |
| 6,034,021 A | 3/2000 | Wilson et al. | 502/103 |
| 6,034,240 A | 3/2000 | LaPointe | 546/24 |
| 6,037,417 A | 3/2000 | Nguyen et al. | 525/240 |
| 6,043,363 A | 3/2000 | LaPointe et al. | 544/225 |
| 6,074,977 A | 6/2000 | Rosen et al. | 502/103 |
| 6,103,657 A | 8/2000 | Murray | 502/155 |
| 6,111,046 A | 8/2000 | Resconi et al. | 526/348 |
| 6,117,962 A | 9/2000 | Weng et al. | 526/351 |
| 6,140,442 A | 10/2000 | Knight et al. | 526/348.1 |
| 6,150,297 A | 11/2000 | Campbell, Jr. et al. | 502/152 |
| 6,153,702 A | 11/2000 | Somers | 525/236 |
| 6,156,846 A | 12/2000 | Tsuruoka et al. | 525/240 |
| 6,162,887 A | 12/2000 | Yamada et al. | 526/351 |
| 6,169,151 B1 | 1/2001 | Waymouth et al. | 526/160 |
| 6,207,756 B1 | 3/2001 | Datta et al. | 525/191 |
| 6,211,300 B1 | 4/2001 | Terano et al. | 525/323 |
| 6,225,243 B1 | 5/2001 | Austin | 442/361 |
| 6,248,829 B1 | 6/2001 | Fischer et al. | 525/191 |
| 6,265,513 B1 | 7/2001 | Murray et al. | 526/352 |
| 6,268,063 B1 | 7/2001 | Kaminaka et al. | 428/500 |
| 6,268,444 B1 | 7/2001 | Klosin et al. | 526/127 |
| 6,268,447 B1 | 7/2001 | Murray et al. | 526/161 |
| 6,274,678 B1 | 8/2001 | Shinozaki et al. | 525/323 |
| 6,284,857 B1 | 9/2001 | Shinozaki et al. | 526/351 |
| 6,303,719 B1 | 10/2001 | Murray et al. | 526/161 |
| 6,306,973 B1 | 10/2001 | Takaoka et al. | 525/240 |
| 6,313,226 B1 | 11/2001 | Yasaka et al. | 525/240 |
| 6,319,991 B1 | 11/2001 | Okayama et al. | 525/240 |
| 6,320,002 B1 | 11/2001 | Murray et al. | 526/89 |
| 6,320,005 B1 | 11/2001 | Murray | 526/161 |
| 6,323,389 B1 | 11/2001 | Thomas et al. | 604/370 |
| 6,326,432 B1 | 12/2001 | Fujita et al. | 525/191 |
| 6,340,730 B1 | 1/2002 | Murray et al. | 526/114 |
| 6,342,564 B1 | 1/2002 | Pitkanen et al. | 525/191 |
| 6,342,566 B2 | 1/2002 | Burkhardt et al. | 525/191 |
| 6,355,725 B2 | 3/2002 | Terano et al. | 525/52 |
| 6,423,782 B1 | 7/2002 | Yukimasa et al. | 525/240 |
| 6,515,155 B1 | 2/2003 | Klosin et al. | 556/11 |
| 2001/0021732 A1 | 9/2001 | Terano et al. | 523/351 |
| 2001/0034411 A1 | 10/2001 | Burkhardt et al. | 525/191 |
| 2001/0034426 A1 | 10/2001 | Waymouth et al. | 526/160 |
| 2002/0004575 A1 * | 1/2002 | Cozewith et al. | |
| 2002/0006993 A1 | 1/2002 | Shinozaki et al. | 524/128 |
| 2002/0019507 A1 | 2/2002 | Karandinos et al. | 526/348.2 |
| 2002/0035210 A1 | 3/2002 | Silvestri et al. | 525/240 |
| 2002/0062011 A1 | 5/2002 | Campbell, Jr. et al. | 534/15 |
| 2002/0137845 A1 | 9/2002 | Boussie et al. | 525/170 |
| 2002/0142912 A1 | 10/2002 | Boussie et al. | 502/152 |
| 2002/0147288 A1 | 10/2002 | Boussie et al. | 526/160 |
| 2002/0151662 A1 | 10/2002 | Campbell, Jr. et al. | 526/127 |
| 2002/0156279 A1 | 10/2002 | Boussie et al. | 546/13 |
| 2002/0165329 A1 | 11/2002 | Klosin et al. | 526/126 |
| 2002/0173419 A1 | 11/2002 | Boussie et al. | 502/117 |
| 2002/0177711 A1 | 11/2002 | LaPointe et al. | 546/13 |
| 2003/0004286 A1 | 1/2003 | Klosin et al. | 526/126 |

* cited by examiner

DSC of the propylene /ethylene copolymer of Comparative Example 1 prepared using a metallocene catalyst.

DSC of the propylene homopolymer of Example 2 prepared using the process of this invention.

TREF DISTRIBUTION COMPARISON $^{13}$C NMR Spectrum of the propylene homopolymer product of Example 7, prepared using Catalyst G.

$^{13}$C NMR Spectrum of the propylene homopolymer product of Example 8, prepared using Catalyst H.

$^{13}C$ NMR Spectrum of the propylene/ethylene copolymer product of Example 2, prepared using Catalyst G.

$^{13}$C NMR Spectrum of the propylene/ethylene copolymer product of Comparative Example 1 prepared using metallocene Catalyst E.

Propylene/Ethylene Copolymers
Haze of 10 mil Compression Molded Films

Effect of Stretching on Elasticity of Various Thermoplastic Elastomers

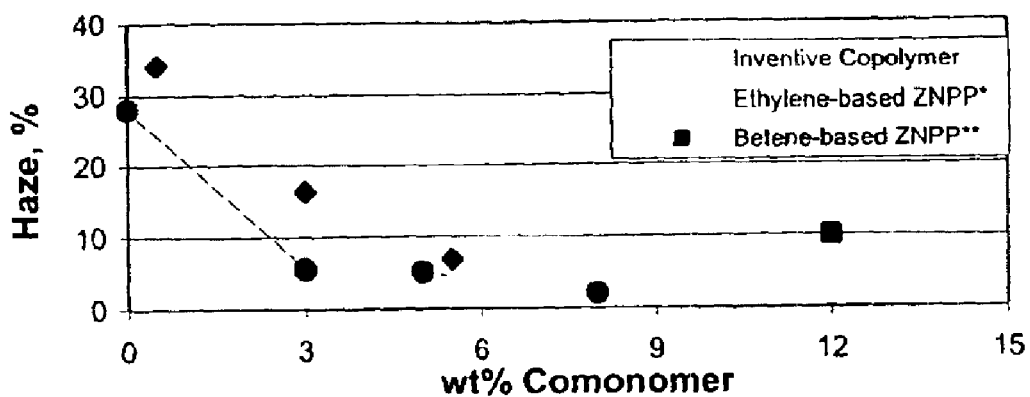
Figure 16 Haz for Various PP Films
*Ziegler-Natta random copolymer PP with ethylene, ** Ziegler-Natta PP with butene
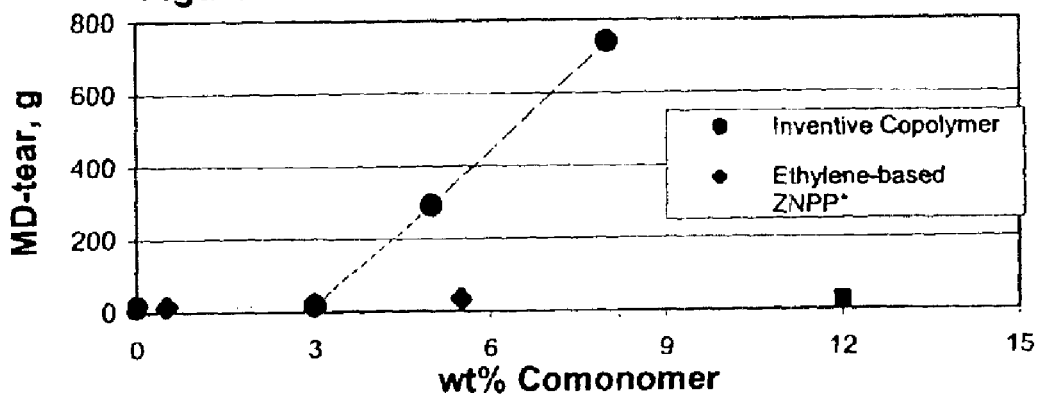
Figure 17 MD-tear for Various PP Films
*Ziegler-Natta randon copolymer PP with ethylene, ** Zeigler-Natta PP with butene

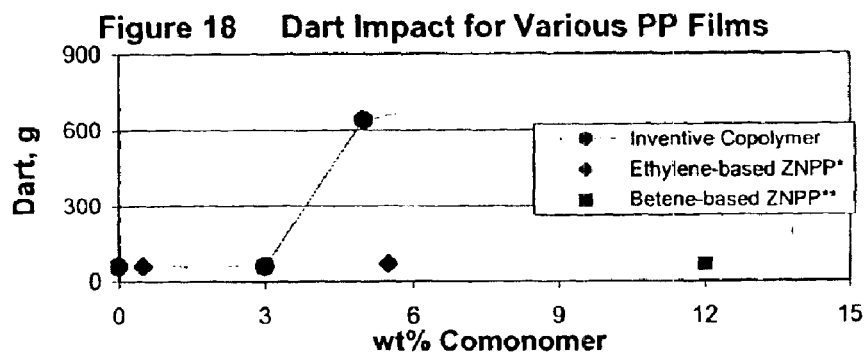
Figure 18  Dart Impact for Various PP Films
*Ziegler-Natta random copolymer PP with ethylene, ** Ziegle-Natta PP with butene
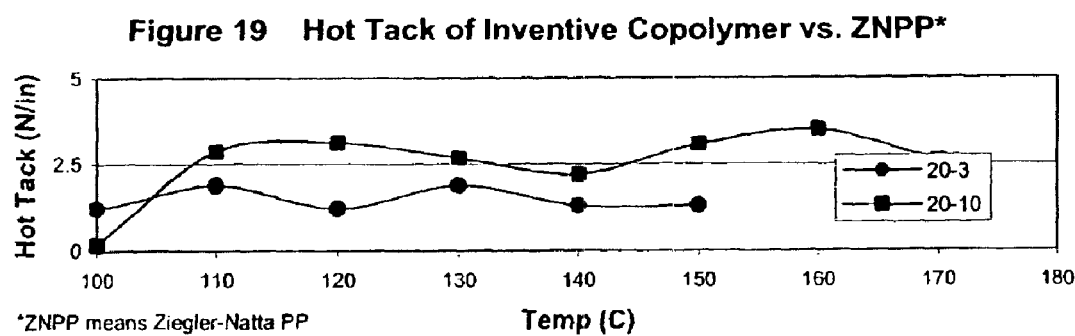
Figure 19  Hot Tack of Inventive Copolymer vs. ZNPP*
*ZNPP means Ziegler-Natta PP
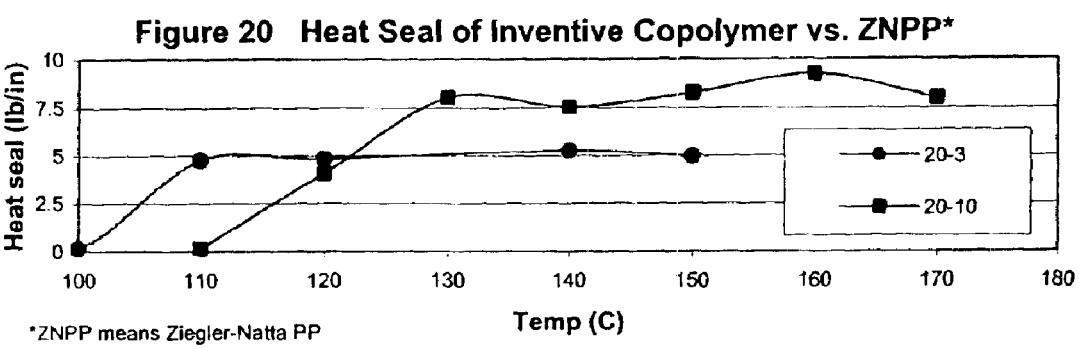
Figure 20  Heat Seal of Inventive Copolymer vs. ZNPP*
*ZNPP means Ziegler-Natta PP FIGURE 21B
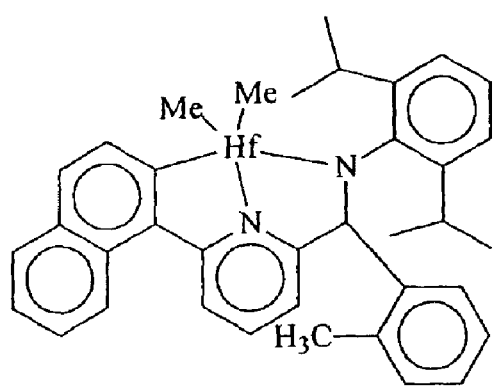
Catalyst J
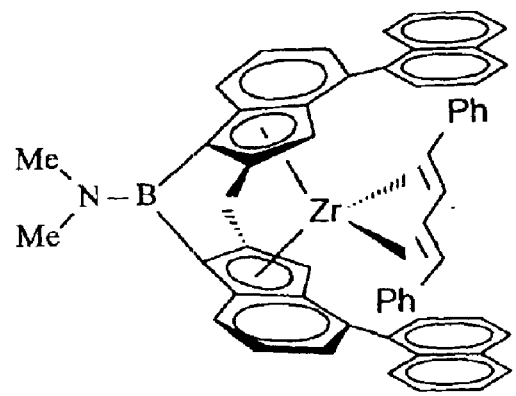
Catalyst I

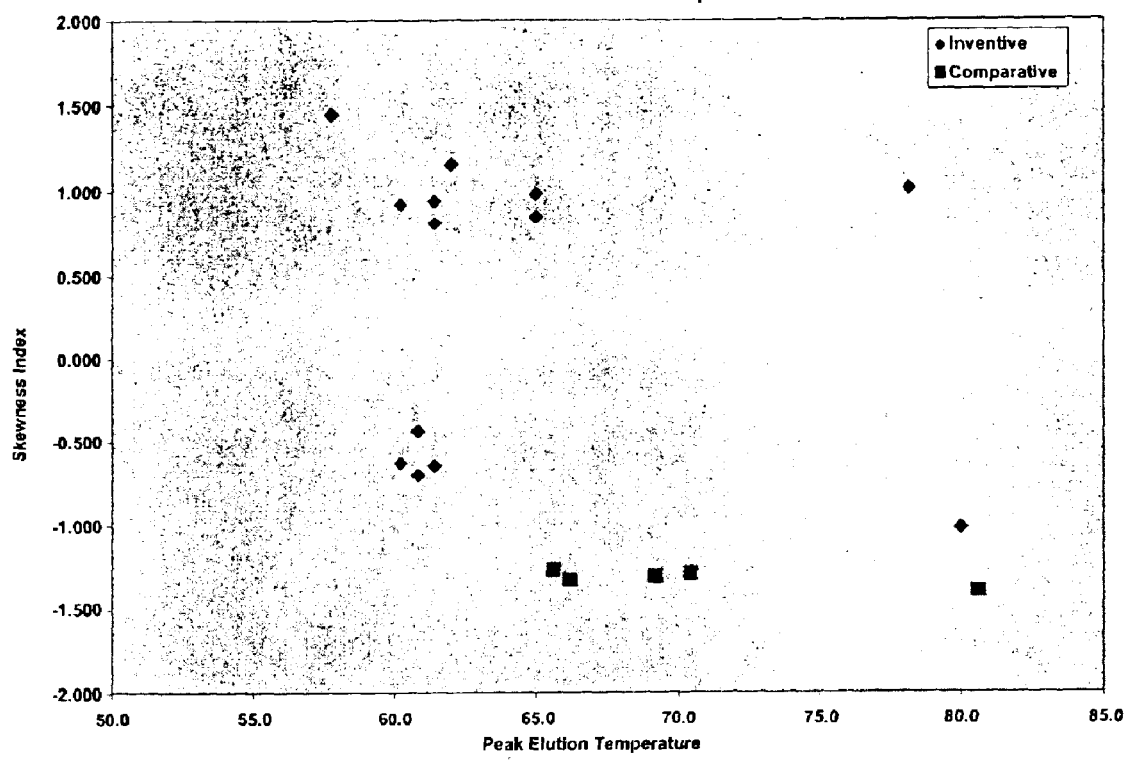

DSC heating trace of the propylene homopolymer of Example 8 prepared using Catalyst H DSC cooling trace of the propylene homopolymer of Example 8 prepared using Catalyst H Peak Melting Point of Propylene/Ethylene Copolymers (C) and Propylene Homopolymers (H)

$T_{1\%c}$ of Propylene/Ethylene Copolymers (C) and Propylene Homopolymers (H)

Breadth of Melting Curves of Propylene/Ethylene Copolymers (C) and Propylene Homopolymers (H)

Peak Melting Rate of Propylene/Ethylene Copolymers (C) and Propylene Homopolymers (H)

Rate of Final Melting of Propylene/Ethylene Copolymers (C) and Propylene Homopolymers (H)

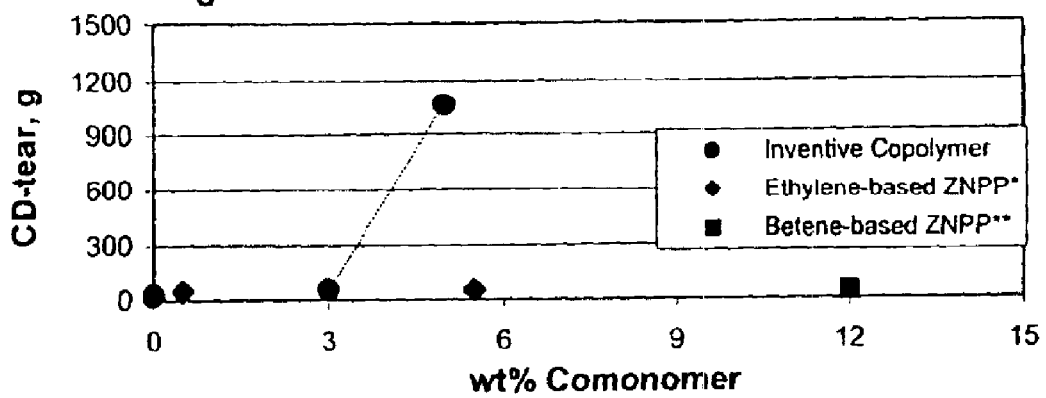
Figure 30 CD-tear for Various PP Films
*Ziegler-Natta random copolymer PP with ethylene. ** Ziegle-Natta PP with betene
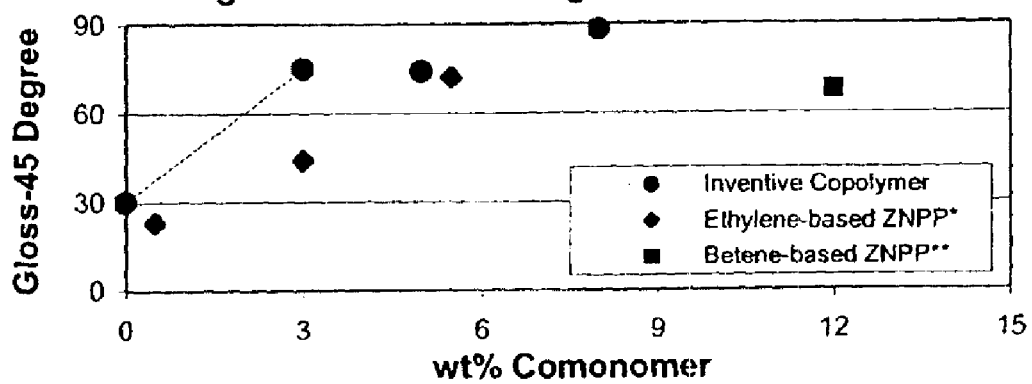
Figure 31 Gloss-45 Degree for Various PP Films
*Ziegler-Natta random copolymer PP with ethylene, ** Ziegler-Natta PP with butene

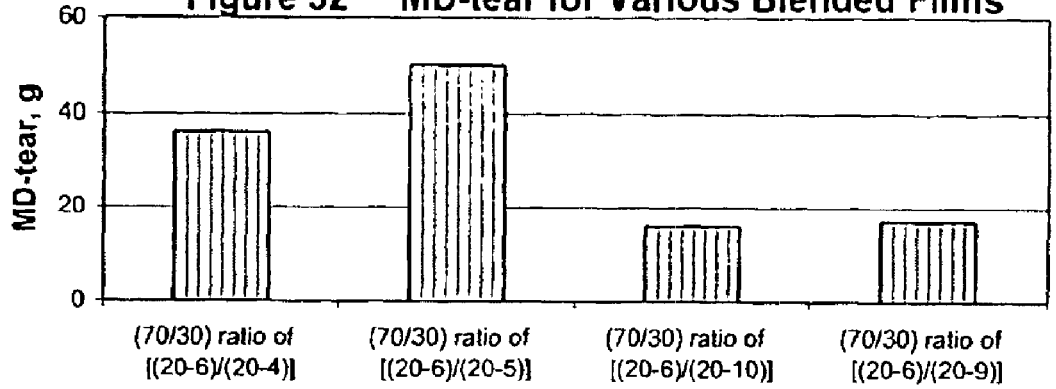
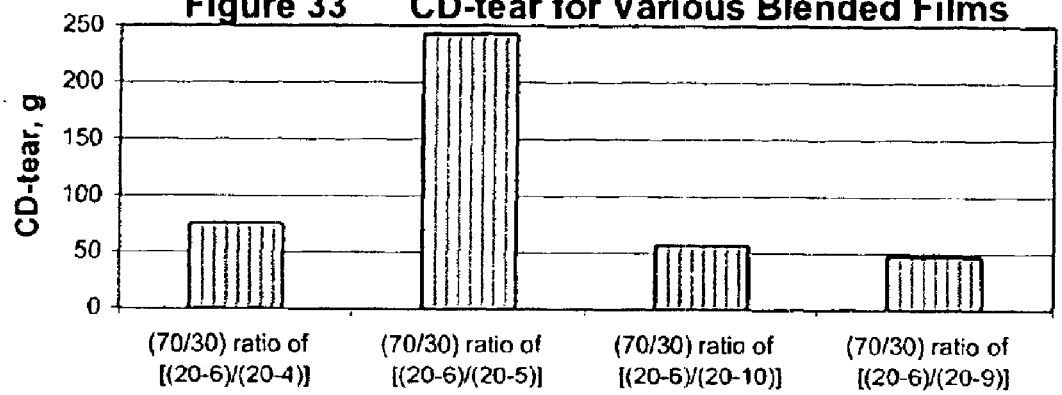
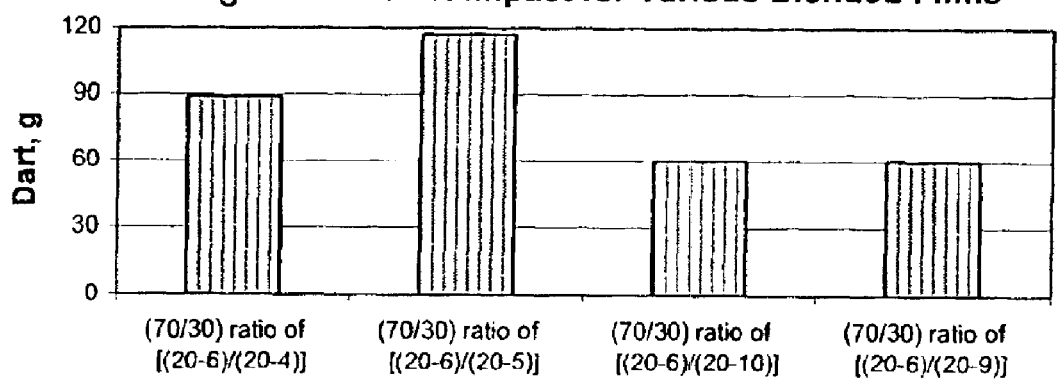

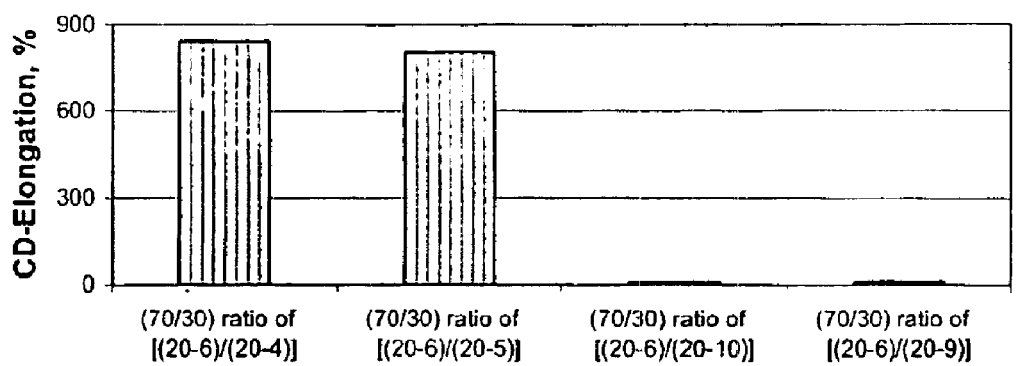
Figure 35  %CD-Elongation for Various Blend d Films
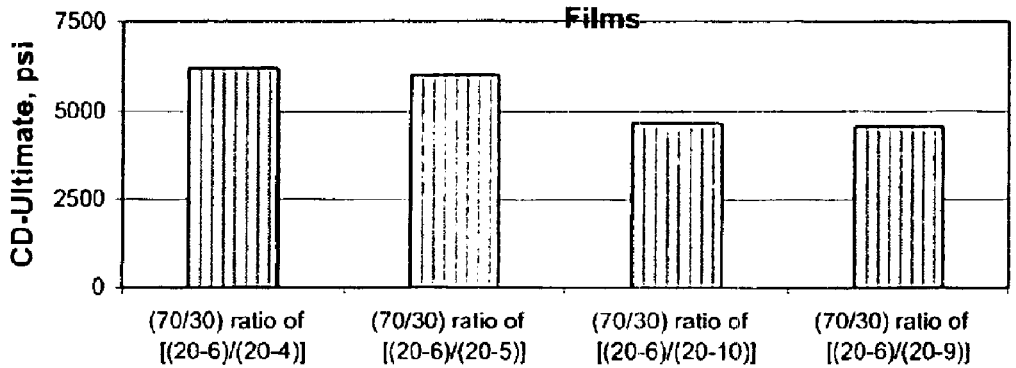
Figure 36  CD-Ultimate Strength for Various Blended Films

ISOTACTIC PROPYLENE COPOLYMERS, THEIR PREPARATION AND USE

CROSS REFERENCE TO RELATED APPLICATION

This application claims the benefit under 35 USC §119(e) of U.S. Provisional Application No. 60/338,881 filed Nov. 6, 2001.

FIELD OF THE INVENTION

This invention relates to polypropylene. In one aspect, the invention relates to isotactic copolymers of propylene and at least one of ethylene and an unsaturated comonomer while in another aspect, the invention relates to polymer blends in which at least one blend component is a copolymer of propylene and at least one of ethylene and an unsaturated comonomer. In another aspect, the invention relates to processes for preparing copolymers of propylene and at least one of ethylene and an unsaturated comonomer and in still another aspect, the invention relates to methods of using these copolymers and isotactic propylene homopolymers.

BACKGROUND OF THE INVENTION

Polypropylene in its many and varied forms is a long established staple of the polymer industry. Depending upon its form, it exhibits a number of desirable properties including toughness (as measured by any of a number of impact tests, e.g., notched Izod, dart drop, etc.), stiffness (as measured by any of a number of modulus tests e.g., Young's), clarity, chemical resistance and heat resistance. Often a particular combination of properties is desired that requires a balancing of various properties against one another (e.g., stiffness against toughness).

Crystalline polypropylene, typically a homopolymer, is used extensively in various moldings because it exhibits desirable mechanical (e.g., rigidity) and chemical resistance properties. For applications that require impact resistance (e.g., automobile parts, appliance facia, packaging, etc.), a copolymer of propylene and ethylene and/or one or more α-olefins is used, or a blend of crystalline polypropylene with one or more polymers that exhibit good impact resistance, e.g., ethylene-propylene (EP) and/or ethylene-propylene-diene (EPDM) rubber. For applications that require toughness and/or heat resistance (e.g., films), preferably the polypropylene has a relatively low melt flow ratio (MFR) or expressed alternatively, a relatively high weight average molecular weight ($M_w$). For applications that require good processing characteristics (e.g., fibers), preferably the polypropylene has a relatively narrow polydisperity or molecular weight distribution (MWD), e.g., less than 3.5.

Crystalline polypropylene has an isotactic structure, and it is readily produced using a Ziegler-Natta (Z-N) or a metal-locene catalyst. While metallocene catalysts are effective for producing propylene homo- and copolymers with a high isotactic index and a relatively narrow MWD, to produce high $M_w$, e.g., over 300,000, propylene homo- or copolymers economically with a metallocene catalyst is relatively difficult, especially in a solution process. Moreover, the industry maintains a continuing interest in new polypropylene polymers, particularly those for use in high impact and fiber applications.

SUMMARY OF THE INVENTION

In a first embodiment, the invention is a copolymer of propylene, ethylene and, optionally, one or more unsaturated comonomers, e.g., $C_{4-20}$ α-olefins, $C_{4-20}$ dienes, vinyl aromatic compounds (e.g., styrene), etc. These copolymers are characterized as comprising at least about 60 weight percent (wt %) of units derived from propylene, about 0.1–35 wt % of units derived from ethylene, and 0 to about 35 wt % of units derived from one or more unsaturated comonomers, with the proviso that the combined weight percent of units derived from ethylene and the unsaturated comonomer does not exceed about 40. These copolymers are also characterized as having at least one of the following properties: (i) $^{13}C$ NMR peaks corresponding to a regio-error at about 14.6 and about 15.7 ppm, the peaks of about equal intensity, (ii) a B-value greater than about 1.4 when the comonomer content, i.e., the units derived from ethylene and/or the unsaturated comonomer(s), of the copolymer is at least about 3 wt %, (iii) a skewness index, $S_{ix}$, greater than about −1.20, (iv) a DSC curve with a $T_{me}$ that remains essentially the same and a $T_{max}$ that decreases as the amount of comonomer, i.e., the units derived from ethylene and/or the unsaturated comonomer(s), in the copolymer is increased, and (v) an X-ray diffraction pattern that reports more gamma-form crystals than a comparable copolymer prepared with a Ziegler-Natta (Z-N) catalyst. Typically the copolymers of this embodiment are characterized by at least two, preferably at least three, more preferably at least four, and even more preferably all five, of these properties.

With respect to the X-ray property of subparagraph (v) above, a "comparable" copolymer is one having the same monomer composition within 10 wt %, and the same Mw within 10 wt %. For example, if an inventive propylene/ethylene/1-hexene copolymer is 9 wt % ethylene and 1 wt % 1-hexene and has a Mw of 250,000, then a comparable polymer would have from 8.1–9.9 wt % ethylene, 0.9–1.1 wt % 1-hexene, and a Mw between 225,000 and 275,000, prepared with a Ziegler-Natta catalyst.

In a second embodiment, the invention is a copolymer of propylene and one or more unsaturated comonomers. These copolymers are characterized in having at least about 60 wt % of the units derived from propylene, and between about 0.1 and 40 wt % the units derived from the unsaturated comonomer. These copolymers are also characterized as having at least one of the following properties: (i) $^{13}C$ NMR peaks corresponding to a regio-error at about 14.6 and about 15.7 ppm, the peaks of about equal intensity, (ii) a B-value greater than about 1.4 when the comonomer content, i.e., the units derived from the unsaturated comonomer(s), of the copolymer is at least about 3 wt %, (iii) a skewness index, $S_{ix}$, greater than about −1.20, (iv) a DSC curve with a $T_{me}$ that remains essentially the same and a $T_{max}$ that decreases as the amount of comonomer, i.e., the units derived from the unsaturated comonomer(s), in the copolymer is increased, and (v) an X-ray diffraction pattern that reports more gamma-form crystals than a comparable copolymer prepared with a Ziegler-Natta (Z-N) catalyst. Typically the copolymers of this embodiment are characterized by at least two, preferably at least three, more preferably at least four, and even more preferably all five, of these properties.

In a third embodiment, the invention is a blend of two or more copolymers in which at least one copolymer is at least one of the propylene/ethylene and propylene/unsaturated comomoner copolymers described in the first and second embodiments (individually and collectively "P/E*copolymer"). The amount of each component in the blend can vary to convenience. The blend may contain any weight percent, based on the total weight of the blend, of either component, and the blend may be either homo- or heterophasic. If the later, the copolymer of the first or second embodiment of this invention can be either the continuous or discontinuous (i.e., dispersed) phase.

In a fourth embodiment, the invention is a blend of (a) at least one propylene homopolymer, and (b) at least one other polymer, e.g. an EP or EPDM rubber. The propylene homopolymer is characterized as having $^{13}$C NMR peaks corresponding to a regio-error at about 14.6 and about 15.7 ppm, the peaks of about equal intensity. Preferably, the propylene homopolymer is characterized as having substantially isotactic propylene sequences, i.e., the sequences have an isotactic triad (mm) measured by $^{13}$C NMR of greater than about 0.85.

The at least one other polymer of (b) of this fourth embodiment is any polymer other than a P/E* copolymer. Typically and preferably, this other polymer(s) is (are) a polyolefin such as one or more of a polyethylene, ethylene/α-olefin, butylene/α-olefin, ethylene/styrene and the like. The blend may contain any weight percent, based on the total weight of the blend, of either component, and the blend may be either homo- or heterophasic. If the later, the propylene homopolymer can be either the continuous or dispersed phase.

In a fifth embodiment, the invention is a process for making a P/E*copolymer, the process comprising contacting propylene and at least one of ethylene and/or one or more unsaturated comonomers under polymerization conditions with an activated, nonmetallocene, metal-centered, heteroaryl ligand catalyst. The process can be conducted in the solution, slurry or gas phase using conventional polymerization conditions and equipment.

In a sixth embodiment, the invention is a solution phase process for making a high $M_w$, narrow MWD P/E* copolymer, the process comprising contacting propylene and at least one of ethylene and one or more unsaturated comonomers under polymerization conditions with an activated, nonmetallocene, metal-centered, heteroaryl ligand catalyst.

In a seventh embodiment, the invention is a series reactor process for making a polymer blend, the blend comprising (A) a P/E* copolymer of this invention, and (B) a propylene homopolymer and/or a second copolymer. The homopolymer may or may not exhibit $^{13}$C NMR peaks corresponding to a regio-error at about 14.6 and about 15.7 ppm, the peaks of about equal intensity, and the second copolymer may or may not exhibit one or more properties characterisic of the P/E* copolymers, e.g., the second copolymer may be an ethylene/α-olefin copolymer. The reactors of this embodiment number two or more. One variation of this process comprises:

1. Contacting in a first reactor (a) propylene, (b) ethylene, and (c) a catalyst under polymerization conditions to make a P/E copolymer, the propylene, ethylene, catalyst, and P/E copolymer forming a reaction mass within the first reactor;
2. Transferring the reaction mass of the first reactor to a second reactor;
3. Feeding additional propylene and/or ethylene to the second reactor;
4. Contacting within the second reactor under polymerization conditions the additional propylene and/or propylene fed to the second reactor with the reaction mass from the first reactor to make the polypropylene homopolymer or the second copolymer; and
5. Recovering the blend from the second reactor.

In one variation, one or both of the P/E copolymer and the second copolymer is a P/E* copolymer. In another variation, if neither the P/E copolymer nor the second copolymer is a P/E* copolymer, then the homopolymer of (A) exhibits $^3$C NMR peaks corresponding to a regio-error at about 14.6 and about 15.7 ppm, the peaks of about equal intensity.

In another variation on this embodiment, the process comprises:

A. Contacting in a first reactor (i) propylene, (ii) ethylene, and (iii) an activated, nonmetallocene, metal-centered, heteroaryl ligand catalyst under polymerization conditions such that at least about 50 wt % of the propylene and substantially all of the ethylene are converted to a P/E*copolymer, the propylene, ethylene, catalyst, and P/E* copolymer forming a reaction mass within the first reactor;

B. Transferring the reaction mass of the first reactor to a second reactor;

C. Optionally, feeding additional propylene to the second reactor;

D. Contacting within the second reactor under polymerization conditions the propylene fed to the second reactor with the reaction mass from the first reactor to make the propylene homopolymer or the second copolymer; and E. Recovering the blend from the second reactor.

If (i) the only comonomers fed to the first reactor are propylene and ethylene, (ii) substantially all of the ethylene is consumed (i.e., converted to polymer), and (iii) only propylene is fed to the second reactor (as unreacted propylene from the first reactor and/or as added propylene), then only propylene polymer containing minor, if any, amounts of ethylene is made in the second reactor.

One interesting feature of certain of the nonmetallocene metal-centered, heteroaryl ligand catalysts used in the practice of this invention is the ability to convert a very high percentage of ethylene monomer to P/E* copolymer in a reactor during a propylene/ethylene copolymerization reaction. For example, with a propylene conversion of about 50% or more, the ethylene conversion may be about 90% or higher. Preferably, the ethylene conversion may be higher than about 95%, more preferably greater than about 97%, even more preferably greater than about 98%, or most preferably greater than about 99%.

One consequence of this high ethylene conversion is that, in a multiple-reactor process, a tough, high $M_w$ propylene/ethylene copolymer can be prepared in one reactor which consumes the majority of the ethylene in the process. Subsequent reactors will experience a greatly reduced ethylene concentration, which can allow for the production of high melting point propylene homopolymer or interpolymers. Preferably, the peak crystallization temperature in a DSC cooling curve of the propylene copolymer comprising propylene and ethylene made in one reactor using a catalyst comprising a nonmetallocene, metal-centered, heteroaryl ligand catalyst is at least 10 degrees C. lower than the peak crystallization temperature in a DSC cooling curve of the propylene interpolymer comprising propylene and ethylene made in a subsequent reactor. Preferably, the peak crystallization temperature is at least 15, more preferably 20, most preferably 40 degrees C. lower. Preferably, at least 2 reactors are used in series, and the process is a solution, slurry, or gas-phase process, or a combination of two or more of these processes. For economic reasons, a continuous process is preferred, but batch or semi-batch processes can also be employed.

In another variation on this embodiment of the invention, the order of the reactors is reversed. In this arrangement, propylene homopolymer, or a propylene copolymer containing only minor amounts of ethylene, as described below, can be made in the first reactor (to which the only monomer fed is propylene) and a copolymer of the first embodiment of this invention is made in the second reactor (to which is fed both propylene and ethylene, and optionally, one or more unsaturated comonomers). This arrangement can be particularly useful for gas phase reactions, but also may be used in a solution or slurry process. Irrespective of the order of the reactors, for this embodiment of the invention it should be appreciated that, when the process is a continuous process involving recovery of the polymer product, recovery of the solvent (if any) and unreacted monomers, and recycle of the solvent (if any) and unreacted monomers to the reactors, small amounts of unconverted ethylene may be present in the recycle stream. For the purposes of this invention, when it is stated that only propylene (or only any other particular monomer(s)) is added to any reactor in such a process, that small amounts of ethylene or other monomers may be present in the recycle stream.

The reactors are operated such that the polymer made in one reactor is different from the polymer made in at least one other reactor. These operational differences include using (i) different weight or mole ratios of propylene, ethylene and/or unsaturated comonomer, (ii) catalysts (each reactor containing a different activated, nonmetallocene, metal-centered, heteroaryl ligand catalyst, or one or more reactors containing an activated nonmetallocene, metal-centered, heteroaryl ligand catalyst and one or more other reactors containing another type of catalyst, e.g., a metallocene catalyst, a Ziegler-Natta (Z-N) catalyst, a constrained geometry catalyst, etc., and/or (iii) operating parameters. One or more reactors can contain more than one catalyst, e.g., one reactor can contain both a metallocene and a Z-N catalyst.

In an eighth embodiment, the invention is a parallel reactor process for making a polymer blend, the blend comprising (a) a P/E* copolymer, and (b) a propylene homopolymer and/or a second copolymer. The homopolymer may or may not exhibit $^{13}$C NMR peaks corresponding to a regio-error at about 14.6 and about 15.7 ppm, the peaks of about equal intensity, and the second copolymer may or may not exhibit one or more properties characterisic of the P/E* copolymers, e.g., the second copolymer may be an ethylene/α-olefin copolymer. One variation of this process comprises:

A. Contacting in a first reactor under polymerization conditions propylene and, optionally, one or more of ethylene and an unsaturated comonomer to make the first polymer;

B. Contacting in a second reactor under polymerization conditions propylene and, optionally, one or more of ethylene and an unsaturated comonomer to make the second polymer;

C. Recovering the first polymer from the first reactor and the second polymer from the second reactor; and D. Blending the first and second polymers to form the polymer blend;

such that at least one of the first and second polymers comprise either (1) a P/E* copolymer, or (2) a propylene homopolymer exhibiting $^{13}$C NMR peaks corresponding to a regio-error at about 14.6 and about 15.7 ppm, the peaks of about equal intensity, made with a nonmetallocene, metal-centered, heteroaryl ligand catalyst.

The first and second reactors are operated such that the first and second polymers are different from one another. These operational differences include using different weight or mole ratios of propylene, ethylene and/or unsaturated comonomer, catalysts (each reactor containing a different nonmetallocene, metal-centered, heteroaryl ligand catalyst, or one or more reactors containing a nonmetallocene, metal-centered, heteroaryl ligand catalyst and one or more other reactors containing a catalyst other than a nonmetallocene, metal-centered, heteroaryl ligand catalyst), and/or operating parameters.

The nonmetallocene, metal-centered, heteroaryl ligand catalysts used in the practice of this invention are used in combination with one or more activators, e.g., an alumoxane. In certain embodiments, the metal is one or more of hafnium and zirconium.

More specifically, in certain embodiments of the catalyst, the use of a hafnium metal has been found to be preferred as compared to a zirconium metal for heteroaryl ligand catalysts. A broad range of ancillary ligand substituents may accommodate the enhanced catalytic performance. The catalysts in certain embodiments are compositions comprising the ligand and metal precursor, and, optionally, may additionally include an activator, combination of activators or activator package.

The catalysts used in the practice of this invention additionally include catalysts comprising ancillary ligand-hafnium complexes, ancillary ligand-zirconium complexes and optionally activators, which catalyze polymerization and copolymerization reactions, particularly with monomers that are olefins, diolefins or other unsaturated compounds. Zirconium complexes, hafnium complexes, compositions or compounds using the disclosed ligands are within the scope of the catalysts useful in the practice of this invention. The metal-ligand complexes may be in a neutral or charged state. The ligand to metal ratio may also vary, the exact ratio being dependent on the nature of the ligand and metal-ligand complex. The metal-ligand complex or complexes may take different forms, for example, they may be monomeric, dimeric or of an even higher order.

For example, suitable ligands useful in the practice of this invention may be broadly characterized by the following general formula:

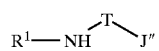

wherein $R^1$ is a ring having from 4–8 atoms in the ring generally selected from the group consisting of substituted cycloalkyl, substituted heterocycloalkyl, substituted aryl and substituted heteroaryl, such that $R^1$ may be characterized by the general formula:

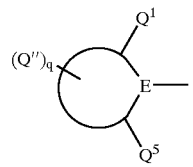

where $Q^1$ and $Q^5$ are substituents on the ring other than to atom E, with E being selected from the group consisting of carbon and nitrogen and with at least one of $Q^1$ or $Q^5$ being bulky (defined as having at least 2 atoms). $Q''_q$ represents additional possible substituents on the ring, with q being 1, 2, 3, 4 or 5 and Q'' being selected from the group consisting of hydrogen, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxyl, aryloxyl, silyl, boryl, phosphino, amino, thio, seleno, halide, nitro, and combinations thereof. T is a bridging group selected group consisting of —CR²R³— and —SiR²R³— with R² and R³ being independently selected from the group consisting of hydrogen, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxyl, aryloxyl, silyl, boryl, phosphino, amino, thio, seleno, halide, nitro, and combinations thereof. J" is generally selected from the group consisting of heteroaryl and substituted heteroaryl, with particular embodiments for particular reactions being described herein.

Also for example, in some embodiments, the ligands of the catalyst used in the practice of this invention may be combined with a metal precursor compound that may be characterized by the general formula $Hf(L)_n$ where L is independently selected from the group consisting of halide (F, Cl, Br, I), alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, carboxylates, thio, 1,3-dionates, oxalates, carbonates, nitrates, sulphates, and combinations thereof. n is 1, 2, 3, 4, 5, or 6.

In certain aspects, it has been discovered that certain ligands complex to the metal resulting in novel complexes that can be used in the practice of this invention. In one aspect, the 3,2 metal-ligand complexes that can be used in the practice of this invention may be generally characterized by the following formula:

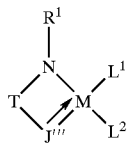

where M is zirconium or hafnium;

R¹ and T are defined above;

J'" being selected from the group of substituted heteroaryls with 2 atoms bonded to the metal M, at least one of those atoms being a heteroatom, and with one atom of J'" is bonded to M via a dative bond, the other through a covalent bond; and L¹ and L² are independently selected from the group consisting of halide, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, carboxylates, thio, 1,3-dionates, oxalates, carbonates, nitrates, sulphates, and combinations of these radicals.

In a ninth embodiment, the invention is the use of the polypropylene homo- and copolymers to make various fabricated articles. These polymers are particularly useful in the manufacture of such shaped articles as films, sheets, fibers, foams and molded articles.

BRIEF DESCRIPTION OF THE DRAWINGS

FIG. 16 shows a comparison of the haze of a blown film made from a P/E* copolymer of this invention against the haze of blown films made from Z-N catalyzed conventional P/E copolymers.

FIG. 17 shows a comparison of the MD-tear of a blown film made from a P/E* copolymer of this invention against the MD-tear of blown films made from Z-N catalyzed conventional P/E copolymers.

FIG. 18 shows a comparison of the dart of a blown film made from a P/E* copolymer of this invention against the dart of blown films made from Z-N catalyzed conventional P/E copolymers.

FIG. 19 shows a comparison of the hot tack behavior of a blown film made from a P/E* copolymer of this invention against the hot tack behavior of blown films made from Z-N catalyzed conventional P/E copolymers.

FIG. 20 shows a comparison of the heat sealing behavior of a blown film made from a P/E* copolymer of this invention against the heat sealing behavior of blown films made from Z-N catalyzed conventional P/E copolymers.

FIGS. 21A and 21B show the chemical structures of various catalysts suitable for embodiments of the invention.

FIG. 22 shows a comparison of the skewness index for the P/E* copolymer of this invention and several P/E copolymers known in the art.

FIG. 30 shows a comparison of the CD-tear of a blown film made from a P/E* copolymer of this invention against the CD-tear of blown films made from Z-N catalyzed conventional P/E copolymers.

FIG. 31 shows a comparison of the Gloss-45 of a blown film made from a P/E* copolymer of this invention against the MD-tear of blown films made from Z-N catalyzed conventional P/E copolymers.

FIG. 32 shows the MD-tear for various blown films made from a blend of P/E* copolymer of this invention and various other P/E copolymers.

FIG. 33 shows the CD-tear for various blown films made from a blend of P/E* copolymer of this invention and various other P/E copolymers.

FIG. 34 shows the Dart Impact for various blown films made from a blend of P/E* copolymer of this invention and various other P/E copolymers.

FIG. 35 shows the CD-Elongation percent for various blown films made from a blend of P/E* copolymer of this invention and various other P/E copolymers.

FIG. 36 shows the CD-Ultimate in psi for various blown films made from a blend of P/E* copolymer of this invention and various other P/E copolymers.

DESCRIPTION OF THE PREFERRED EMBODIMENTS

Molecular Weight

Figure 1:
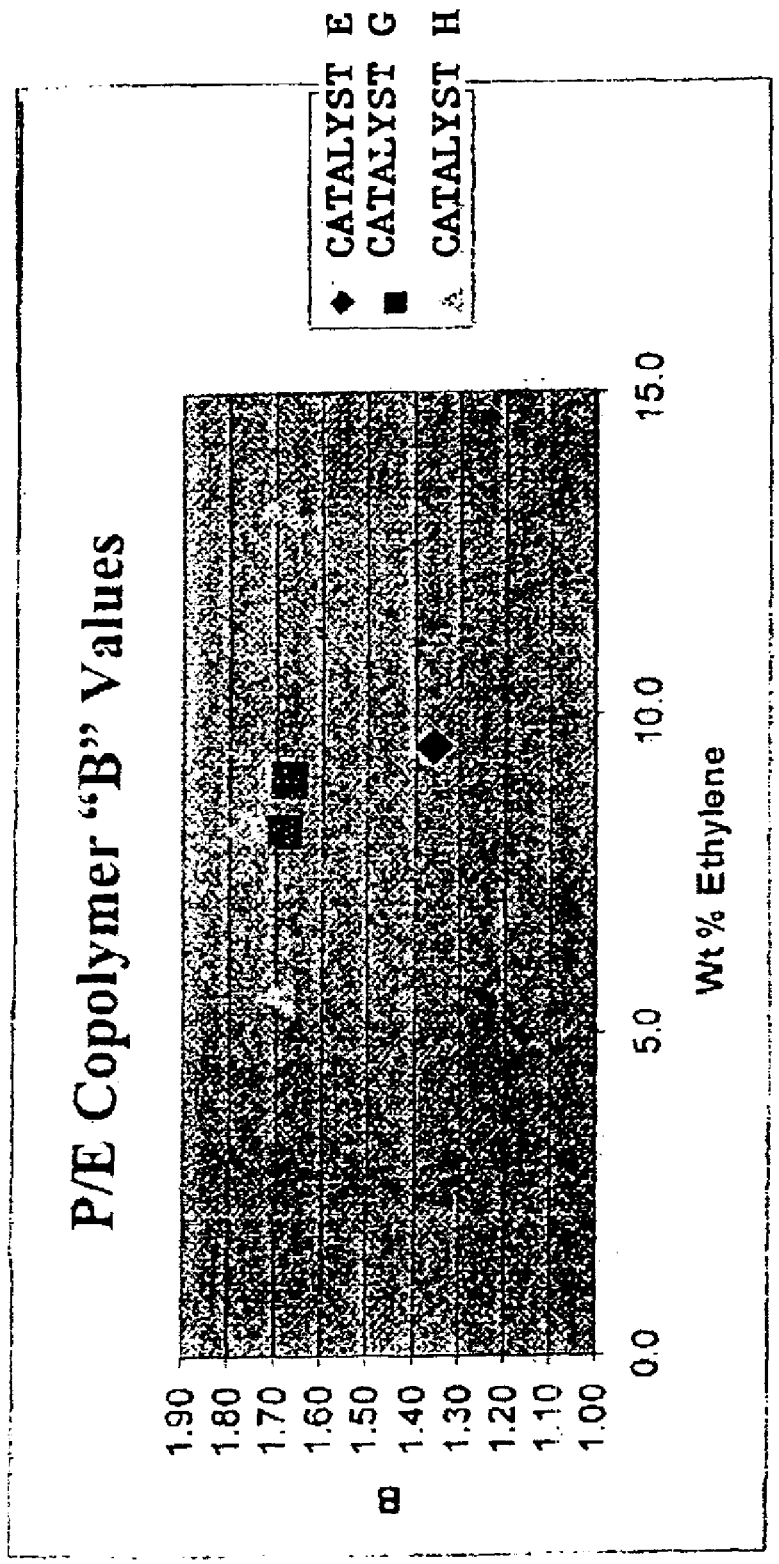
FIG. 1 illustrates the unusual comonomer distribution of a propylene/ethylene copolymer of this invention.

The weight average molecular weight (Mw) of the polymers of this invention can vary widely, but typically it is between about 30,000 and 1,000,000 (with the understanding that the only limit on the minimum or the maximum $M_w$ is that set by practical considerations). Preferably the minimum Mw is about 50,000, more preferably about 75,000 and even more preferably about 100,000. "High molecular weight", "high weight average molecular weight", "high Mw" and similar terms mean a weight average molecular weight of at least about 250,000, preferably of at least about 300,000 and more preferably 350,000, and more preferably at least about 400,000.

Polydispersity

The polydispersity of the polymers of this invention is typically between about 2 and about 6. "Narrow polydisperity", "narrow molecular weight distribution", "narrow MWD" and similar terms mean a ratio ($M_w/M_n$) of weight average molecular weight ($M_w$) to number average molecular weight ($M_n$) of less than about 3.5, preferably less than about 3.0, more preferably less than about 2.8, more preferably less than about 2.5, and most preferably less than about 2.3. Polymers for use in fiber and extrusion coating applications typically have a narrow polydispersity.

Blends comprising the inventive polymers may have a higher polydispersity, depending on the molecular weight of the other components of the blend. In particular, blends produced utilizing any of the multiple reactor processes disclosed in the present invention may have a broad range of polydispersities, from as low as about 2 to as high as 100 or more. Preferably, the $M_w/M_n$ of such blends is between about 2 and about 50, more preferably between about 2 and about 20, most preferably between about 2 and about 10.

Gel Permeation Chromatography

Molecular weight distribution of the polymers is determined using gel permeation chromatography (GPC) on a Polymer Laboratories PL-GPC-220 high temperature chromatographic unit equipped with four linear mixed bed columns (Polymer Laboratories (20-micron particle size)). The oven temperature is at 160° C. with the autosampler hot zone at 160° C. and the warm zone at 145° C. The solvent is 1,2,4-trichlorobenzene containing 200 ppm 2,6-di-t-butyl-4-methylphenol. The flow rate is 1.0 milliliter/minute and the injection size is 100 microliters. About 0.2% by weight solutions of the samples are prepared for injection by dissolving the sample in nitrogen purged 1,2,4-trichlorobenzene containing 200 ppm 2,6-di-t-butyl-4-methylphenol for 2.5 hrs at 160° C. with gentle mixing.

The molecular weight determination is deduced by using ten narrow molecular weight distribution polystyrene standards (from Polymer Laboratories, EasiCal PS1 ranging from 580–7,500,000 g/mole) in conjunction with their elution volumes. The equivalent polypropylene molecular weights are determined by using appropriate Mark-Houwink coefficients for polypropylene (as described by Th. G. Scholte, N. L. J. Meijerink, H. M. Schoffeleers, and A. M. G. Brands, J. Appl. Polym. Sci., 29, 3763–3782 (1984)) and polystyrene (as described by E. P. Otocka, R. J. Roe, N. Y. Hellman, P. M. Muglia, Macromolecules, 4, 507 (1971)) in the Mark-Houwink equation:

$$\{N\}=KM^a$$

where $K_{pp}$=1.90E–04, $a_{pp}$=0.725 and $K_{ps}$=1.26E–04 $a_{ps}$=0.702.

Differential Scanning Calorimetry

Differential scanning calorimetry (DSC) is a common technique that can be used to examine the melting and crystallization of semi-crystalline polymers. General principles of DSC measurements and applications of DSC to studying semi-crystalline polymers are described in standard texts (e.g., E. A. Turi, ed., *Thermal Characterization of Polymeric Materials,* Academic Press, 1981). Certain of the copolymers of this invention are characterized by a DSC curve with a $T_{me}$ that remains essentially the same and a $T_{max}$ that decreases as the amount of unsaturated comonomer in the copolymer is increased. $T_{me}$ means the temperature at which the melting ends. $T_{max}$ means the peak melting temperature.

Differential Scanning Calorimetry (DSC) analysis is determined using a model Q1000 DSC from TA Instruments, Inc. Calibration of the DSC is done as follows. First, a baseline is obtained by running the DSC from −90° C. to 290° C. without any sample in the aluminum DSC pan. Then 7 milligrams of a fresh indium sample is analyzed by heating the sample to 180° C., cooling the sample to 140° C. at a cooling rate of 10° C./min followed by keeping the sample isothermally at 140° C. for 1 minute, followed by heating the sample from 140° C. to 180° C. at a heating rate of 10° C./min. The heat of fusion and the onset of melting of the indium sample are determined and checked to be within 0.5° C. from 156.6° C. for the onset of melting and within 0.5 J/g from 28.71 J/g for the heat of fusion. Then deionized water is analyzed by cooling a small drop of fresh sample in the DSC pan from 25° C. to −30° C. at a cooling rate of 10° C./min. The sample is kept isothermally at −30° C. for 2 minutes and heated to 30° C. at a heating rate of 10° C./min. The onset of melting is determined and checked to be within 0.5° C. from 0° C.

The polypropylene samples are pressed into a thin film at a temperature of 190° C. About 5 to 8 mg of sample is weighed out and placed in the DSC pan. The lid is crimped on the pan to ensure a closed atmosphere. The sample pan is placed in the DSC cell and the heated at a high rate of about 100° C./min to a temperature of about 30° C. above the melt temperature. The sample is kept at this temperature for about 3 minutes. Then the sample is cooled at a rate of 10° C./min to −40° C., and kept isothermally at that temperature for 3 minutes. Consequently the sample is heated at a rate of 10° C./min until complete melting. The resulting enthalpy curves are analyzed for peak melt temperature, onset and peak crystallization temperatures, heat of fusion and heat of crystallization, $T_{me}$, and any other DSC analyses of interest.

B-Value

"High B-value" and similar terms mean the ethylene units of a copolymer of propylene and ethylene, or a copolymer of propylene, ethylene and at least one unsaturated comononomer, is distributed across the polymer chain in a nonrandom manner. B-values range from 0 to 2 with 1 designating a perfectly random distribution of comonomer units. The higher the B-value, the more alternating the comonomer distribution in the copolymer. The lower the B-value, the more blocky or clustered the comonomer distribution in the copolymer. The high B-values of the polymers of this invention are typically at least about 1.3, preferably at least about 1.4, more preferably at least about 1.5 and most preferably at least about 1.7. The B-value is calculated as follows.

B is defined for a propylene/ethylene copolymer as:

$$B = \frac{f(EP + PE)}{2 \cdot F_E \cdot F_P}$$

where f(EP+PE)=the sum of the EP and PE diad fractions; and Fe and Fp=the mole fraction of ethylene and propylene in the copolymer, respectively. B-values can be calculated for other copolymers in an analogous manner by assignment of the respective copolymer diads. For example, calculation of the B-value for a propylene/1-octene copolymer uses the following equation:

$$B = \frac{f(OP + PO)}{2 \cdot F_O \cdot F_P}$$

For propylene polymers made with a metallocene catalyst, the B-values are typically between 1.1 and 1.3. For propylene polymers made with a constrained geometry catalyst, the B-values are typically between 0.9 and 1.0. In contrast, the B-values of the propylene polymers of this invention, typically made with an activated nonmetallocene, metal-centered, heteroaryl ligand catalyst, are above about 1.4, typcially between about 1.5 and about 1.85. In turn, this means that for any propylene-ethylene copolymer of this invention, not only is the propylene block length relatively short for a given percentage of ethylene but very little, if any, long sequences of 3 or more sequential ethylene insertions are present in the copolymer, unless the ethylene content of the polymer is very high. FIG. 1 and the data of the following tables are illustrative. The catalysts are activated nonmetallocene, metal-centered, heteroaryl ligand catalysts, and these made polymers of this invention. The Catalyst E is a metallocene catalyst, and it did not make the polymers of this invention. Interestingly, the B-values of the propylene polymers of this invention remained high even for polymers with relatively large amounts, e.g., >30 mole %, ethylene.

TABLE A

B-Values of Selected Propylene Polymers

| Number | Description | MFR (g/10 min) | Density (kg/dm 3#) | Ethylene (mol %) | Regio-errors 14–16 ppm (mole %) (average of two) | B | Tmax (° C.) | Cryst. (%) (from Hf) | Tg (° C.) |
|---|---|---|---|---|---|---|---|---|---|
| A-1 | P/E* via Catalyst I | 25.8 | 0.8864 | 10.6 | 0.00 | 1.40 | 104.7 | 37.3 | −20.9 |
| A-2 | HPP via Catalyst G | 1.9 | 0.8995 | 0.0 | 1.35 | None | 139.5 | 48.7 | −6.9 |
| A-3 | P/E* via Catalyst G | 1.7 | 0.8740 | 11.8 | 0.24 | 1.67 | 63.3 | 24.4 | −23.6 |
| A-4 | P/E* via Catalyst G | 1.5 | 0.8703 | 12.9 | 0.32 | 1.66 | 57.7 | 21.9 | −24.5 |
| A-5 | HPP via Catalyst H | 2.5 | 0.9021 | 0.0 | 1.18 | none | 143.5 | 61.4 | −6.0 |
| A-6 | P/E* via Catalyst H | 1.9 | 0.8928 | 4.3 | 0.57 | 1.77 | 120.6 | 48.3 | −13.8 |
| A-7 | P/E* via Catalyst H | 2.2 | 0.8850 | 8.2 | 0.47 | 1.71 | 96.0 | 40.5 | −19.3 |
| A-8 | P/E* via Catalyst H | 2.3 | 0.8741 | 11.8 | 0.34 | 1.79 | 67.9 | 27.4 | −23.7 |

TABLE A-continued

B-Values of Selected Propylene Polymers

| Number | Description | MFR (g/10 min) | Density (kg/dm 3#) | Ethylene (mol %) | Regio-errors 14–16 ppm (mole %) (average of two) | B | Tmax (° C.) | Cryst. (%) (from Hf) | Tg (° C.) |
|---|---|---|---|---|---|---|---|---|---|
| A-9 | P/E* via Catalyst H | 2 | 0.8648 | 15.8 | 0.24 | 1.67 | 53.7 | 10.5 | −27.6 |
| A-10 | P/E* via Catalyst H | 2.0 | 0.8581 | 18.6 | 0.18 | 1.70 | none | 2.6 | −29.9 |

Catalyst I is dimethyleamidoborane-bis-$\eta^5$-(2-methyl-4-napthylinden-1-yl)zirconium $\eta^4$-1,4,-diphenyl-1,3-butadine.
HPP means polypropylene homopolymer.

TABLE B

B-Values of Selected Propylene/Ethylene Copolymers

| Number | Description | MFR (g/10 min) | Density (kg/dm3) | Ethylene (mol %) | Regio-errors 14–16 ppm (mole %) (average of two) | B | Tmax (° C.) | Cryst. (%) (from Hf) | Tg (° C.) |
|---|---|---|---|---|---|---|---|---|---|
| B-1 | P/E* via Catalyst H | 1.8 | | 1.6 | 0.37 | 1.78 | 138.2 | 53.9 | −8.1 |
| B-2 | P/E* via Catalyst H | 1.7 | | 7.7 | 0.38 | 1.66 | 105.6 | 38.9 | −18.5 |
| B-3 | P/E* via Catalyst H | 27.0 | | 7.8 | 0.41 | 1.61 | 107.7 | 39.6 | −18.2 |
| B-4 | P/E* via Catalyst H | 1.9 | | 12.3 | 0.31 | 1.58 | 74.7 | 30.7 | −22.5 |
| B-5 | P/E* via Catalyst H | 25.5 | | 14.8 | 0.21 | 1.67 | 90.6 | 31.2 | −22.9 |
| B-6 | P/E* via Catalyst H | 25.7 | | 12.4 | 0.31 | 1.61 | 67.4 | 20.8 | −26.8 |
| B-7 | P/E* via Catalyst H | 52.2 | | 14.7 | 0.30 | 1.60 | 78.1 | 19.9 | −25.9 |
| B-8 | P/E* via Catalyst H | 27.0 | | 33.7 | 0.00 | 1.67 | none | 0.0 | −39.2 |
| B-9 | P/E* via Catalyst H | 76.0 | | 31.3 | 0.00 | 1.67 | none | 0.0 | −39.2 |
| B-10 | P/E* via Catalyst J | | | 12.0 | 0.25 | 1.61 | 72.4 | 33.2 | −22.8 |
| B-11 | P/E* via Catalyst J | | | 8.9 | 0.37 | 1.63 | 91.4 | 40.1 | −19.8 |
| B-12 | P/E* via Catalyst J | | | 8.5 | 0.44 | 1.68 | 101.7 | 38.7 | −20.0 |
| B-13 | P/E* via Catalyst J | | | 7.6 | 0.47 | 1.68 | 107.6 | 43.2 | −18.8 |
| B-14 | P/E* via Catalyst J | | | 7.6 | 0.35 | 1.64 | 106.2 | 42.4 | −18.5 |
| B-15 | P/E* via Catalyst J | | | 8.6 | 0.33 | 1.64 | 104.4 | 41.0 | −19.5 |
| B-16 | P/E* via Catalyst J | | | 9.6 | 0.35 | 1.65 | 85.5 | 38.1 | −20.6 |
| B-17 | P/E* via Catalyst J | | | 8.6 | 0.37 | 1.63 | 104.1 | 41.8 | −19.6 |
| B-18 | P/E* via Catalyst J | | | 8.6 | 0.34 | 1.62 | 90.8 | 40.8 | −19.6 |
| B-19 | P/E* via Catalyst J | | | 8.6 | 0.40 | 1.58 | 93.3 | 41.9 | −19.2 |

Figure 2A:
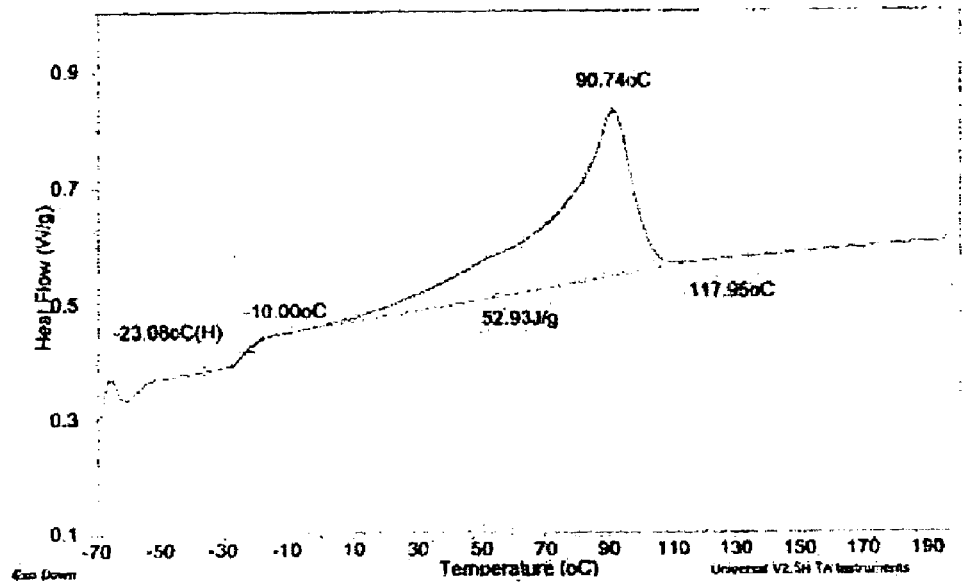
FIGS. 2A and 2B show a comparison of the DSC heating traces of the propylene/ethylene (P/E) copolymer of Comparative Example 1 and the P/E* copolymer of Example 2, respectively.
Figure 2B:
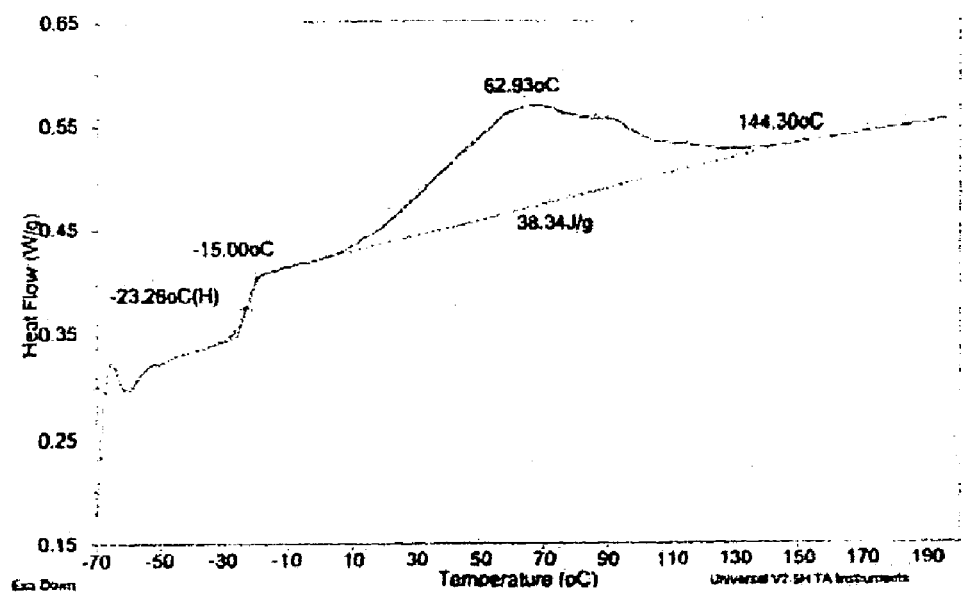

The novel processes disclosed of this invention can be used to produce propylene interpolymers of ethylene and optionally $C_4$–$C_{20}$ alpha-olefins having a relatively broad melting point in a DSC heating curve. While not wishing to be held to any particular theory of operation, it is believed that the high B values for the novel propylene/ethylene interpolymers and the process for their manufacture lead to an ethylene distribution within the polymer chains that leads to a broad melting behavior. In FIGS. 2A and 2B, for example, a relatively narrow melting peak is observed for a propylene/ethylene copolymer prepared using a metallocene as a comparative example (Comparative Example 1), while the melting peak for a similar copolymer of propylene and ethylene prepared according to the teachings herein exhibits a broad melting point. Such broad melting behavior is useful in applications requiring, for example, a relatively low heat seal initiation temperature, or a broad hot tack and/or heat seal window.

Thermal Properties

Figure 3:
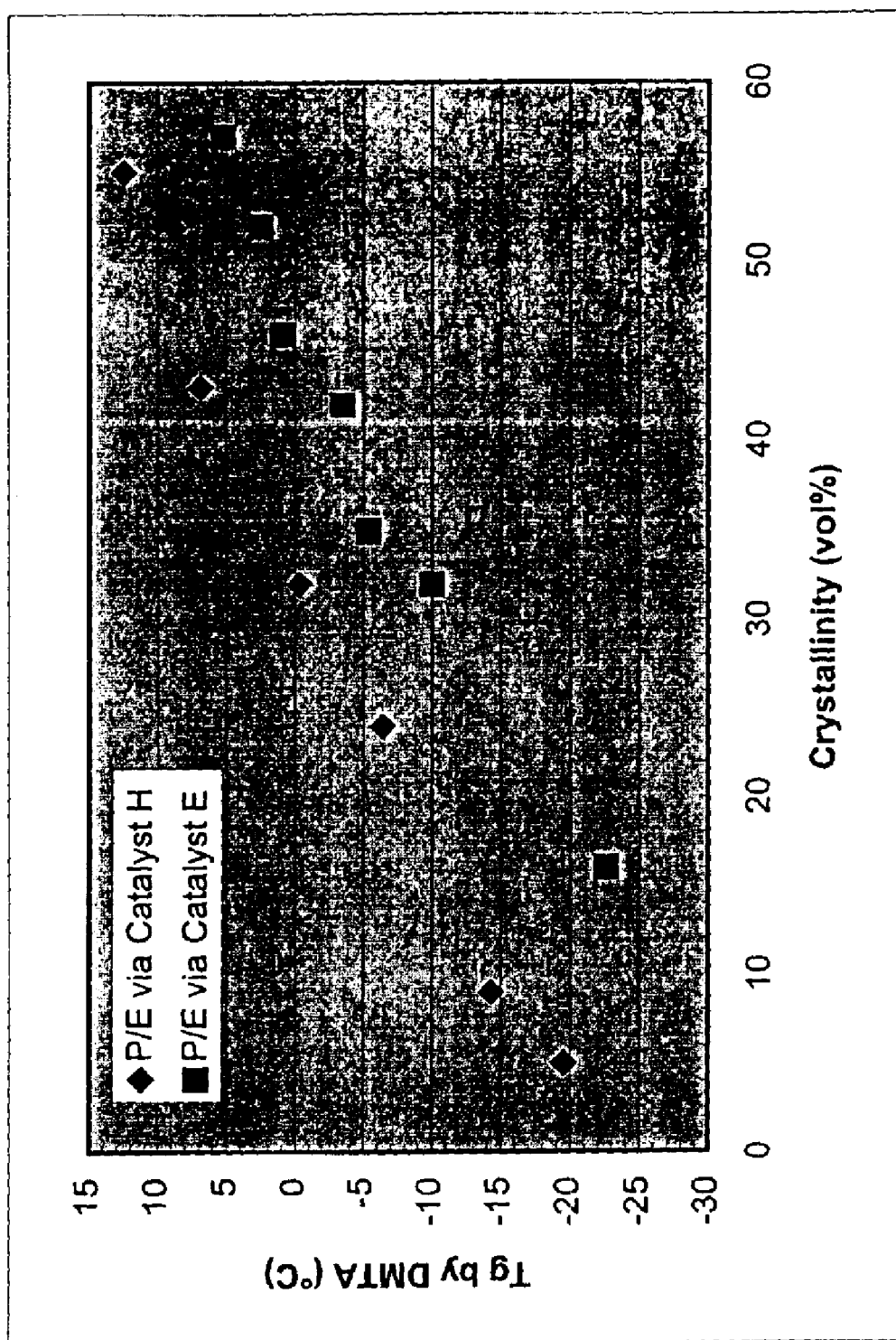
FIG. 3 shows a comparison of the Tg data of a propylene/ethylene (P/E*) copolymer of this invention and a conventional Ziegler-Natta (Z-N) catalyzed P/E copolymer at equivalent crystallinity.
Figure 4:
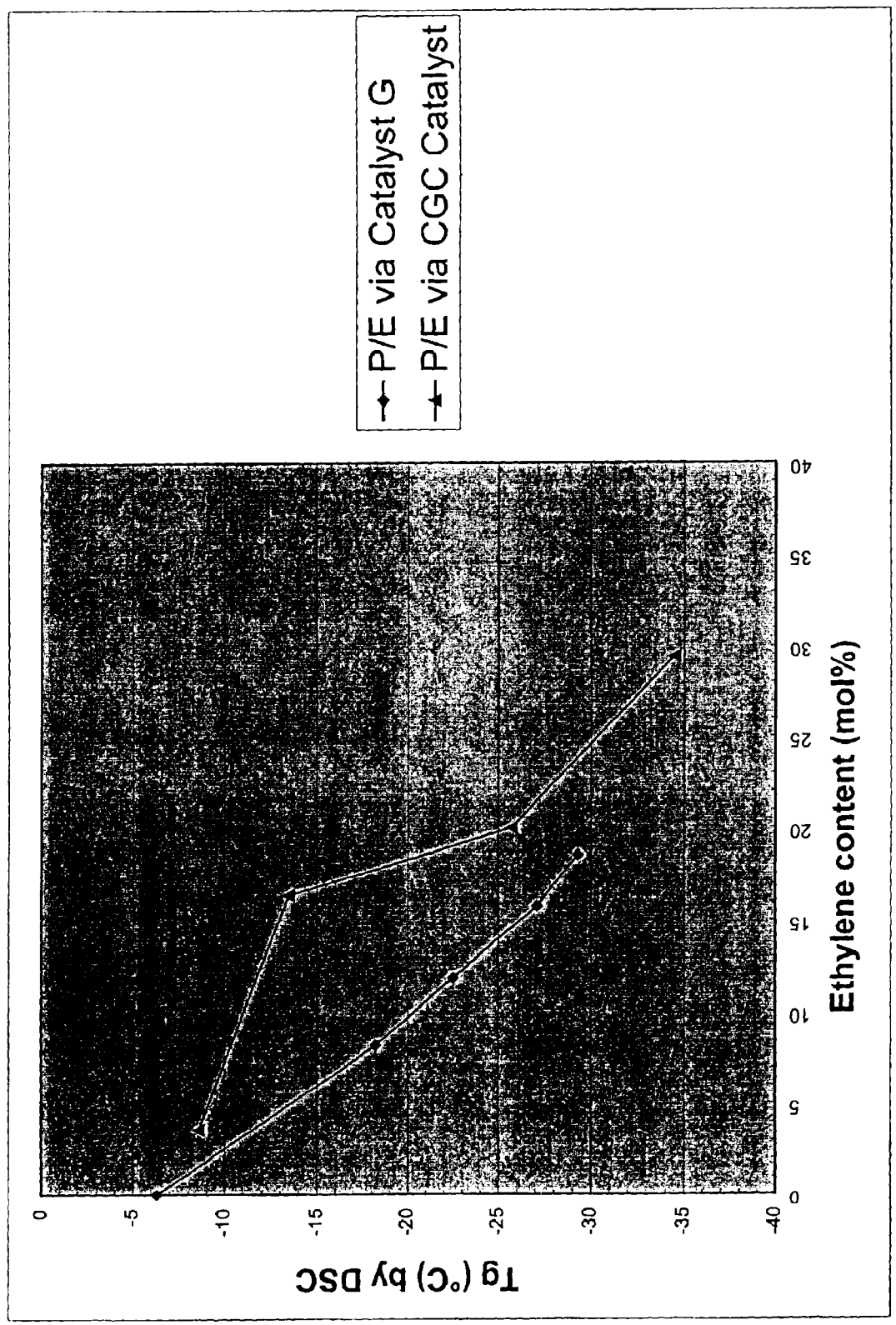
FIG. 4 shows a comparison of the Tg data of a P/E* copolymer of this invention and a conventional constrained geometry catalyst (CGC) P/E copolymer at the same ethylene content.

FIGS. 3 and 4 further illustrate the thermal properties of the propylene polymers of this invention. FIG. 3 illustrates that the propylene polymers of this invention have a higher glass transition temperature (Tg) than do comparable metallocene-catalysed propylene polymers at a equivalent crystallinity. This means that the P/E* copolymers of this invention are likely to exhibit better creep resistance than conventional metallocene-catalyzed propylene copolymers.

Moreover, the $T_{max}$ data of Table A shows that the P/E* copolymers of this invention have a lower melting point at the same crystallinity as a metallocene-catalyzed propylene copolymer. This, in turn, means that the propylene polymers of this invention are likely to process better (e.g., require less heating) than conventional metallocene-catalyzed propylene polymers.

FIG. 4 illustrates that the propylene polymers of this invention also have a lower Tg at an equivalent ethylene content than a propylene polymer made with a constrained geometry catalyst (CGC) and this, in turn, means that the inventive propylene polymers are likely to exhibit better low temperature toughness than the CGC propylene polymers making the inventive polymers attractive candidates for food packaging applications.

Temperature-Rising Elution Fractionation

The determination of crystallizable sequence length distribution can be accomplished on a preparative scale by temperature-rising elution fractionation (TREF). The relative mass of individual fractions can be used as a basis for estimating a more continuous distribution. L. Wild, et al., *Journal of Polymer Science: Polymer. Physics Ed.,* 20, 441 (1982), scaled down the sample size and added a mass detector to produce a continuous representation of the distribution as a function of elution temperature. This scaled down version, analytical temperature-rising elution fractionation (ATREF), is not concerned with the actual isolation of fractions, but with more accurately determining the weight distribution of fractions.

While TREF was originally applied to copolymers of ethylene and higher α-olefins, it can also be used for the analysis of copolymers of propylene with ethylene (or higher α-olefins). The analysis of copolymers of propylene requires higher temperatures for the dissolution and crystallization of pure, isotactic polypropylene, but most of the copolymerization products of interest elute at similar temperatures as observed for copolymers of ethylene. The following table is a summary of conditions used for the analysis of copolymers of propylene. Except as noted the conditions for TREF are consistent with those of Wild, et al., ibid, and Hazlitt, *Journal of Applied Polymer Science: Appl. Polym. Symp.*,45, 25(1990).

TABLE C

Parameters Used for TREF

| Parameter | Explanation |
| --- | --- |
| Column type and size | Stainless steel shot with 1.5 cc interstitial volume |
| Mass detector | Single beam infrared detector at 2920 cm$^{-1}$ |
| Injection temperature | 150° C. |
| Temperature control device | GC oven |
| Solvent | 1,2,4-trichlorobenzene |
| Concentration | 0.1 to 0.3% (weight/weight) |
| Cooling Rate 1 | 140° C. to 120° C. @ −6.0° C./min. |
| Cooling Rate 2 | 120° C. to 44.5° C. @ −0.1° C./min. |
| Cooling Rate 3 | 44.5° C. to 20° C. @ −0.3° C./min. |
| Heating Rate | 20° C. to 140° C. @ 1.8° C./min. |
| Data acquisition rate | 12/min. |

Figure 5:
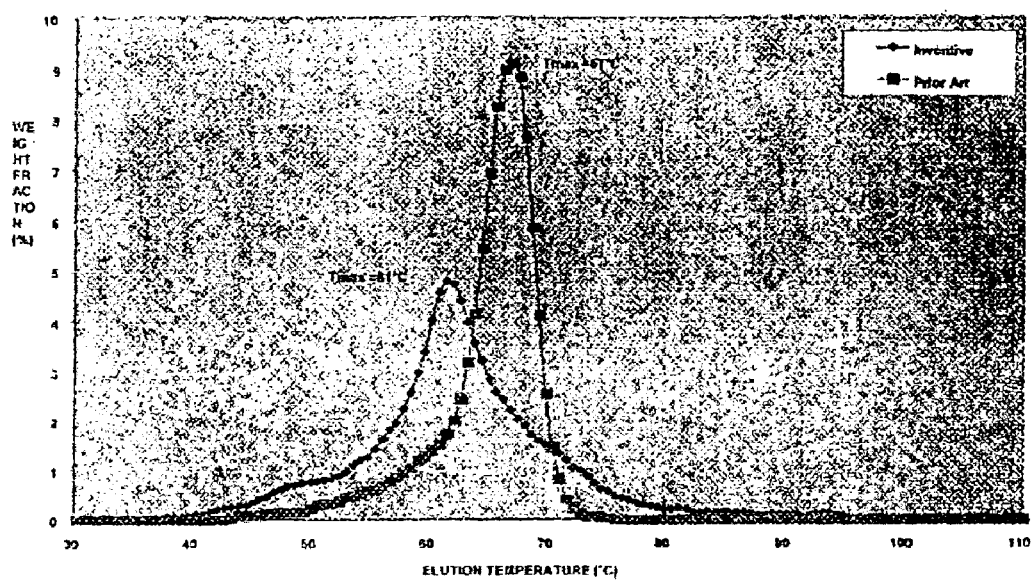
FIG. 5 shows a comparison of a TREF curve for a conventional metallocene catalyzed P/E copolymer and a P/E* copolymer of this invention.

The data obtained from TREF are expressed as a normalized plot of weight fraction as a function of elution temperature. The separation mechanism is analogous to that of copolymers of ethylene, whereby the molar content of the crystallizable component (ethylene) is the primary factor that determines the elution temperature. In the case of copolymers of propylene, it is the molar content of isotactic propylene units that primarily determines the elution temperature. FIG. 5 is a representation of the typical type of distribution one would expect for a propylene/ethylene copolymer made with a metallocene polymer and an example of the current invention.

The shape of the metallocene curve in FIG. 5 is typical for a homogeneous copolymer. The shape arises from the inherent, random incorporation of comonomer. A prominent characteristic of the shape of the curve is the tailing at lower elution temperature compared to the sharpness or steepness of the curve at the higher elution temperatures. A statistic that reflects this type of asymmetry is skewness. Equation 1 mathematically represents the skewness index, $S_{ix}$, as a measure of this asymmetry.

$$S_{ix} = \frac{\sqrt[3]{\sum w_i * (T_i - T_{Max})^3}}{\sqrt{\sum w_i * (T_i - T_{Max})^2}}.$$

Equation 1

The value, $T_{Max}$, is defined as the temperature of the largest weight fraction eluting between 50 and 90° C. in the TREF curve. $T_i$ and $w_i$ are the elution temperature and weight fraction respectively of an arbitrary, i$^{th}$ fraction in the TREF distribution. The distributions have been normalized (the sum of the $w_i$ equals 100%) with respect to the total area of the curve eluting above 30° C. Thus, the index reflects only the shape of the crystallized polymer and any uncrystallized polymer (polymer still in solution at or below 30° C.) has been omitted from the calculation shown in Equation 1.

Polymer Definitions and Descriptions

"Polymer" means a macromolecular compound prepared by polymerizing monomers of the same or different type. "Polymer" includes homopolymers, copolymers, terpolymers, interpolymers, and so on. The term "interpolymer" means a polymer prepared by the polymerization of at least two types of monomers or comonomers. It includes, but is not limited to, copolymers (which usually refers to polymers prepared from two different types of monomers or comonomers, although it is often used interchangeably with "interpolymer" to refer to polymers made from three or more different types of monomers or comonomers), terpolymers (which usually refers to polymers prepared from three different types of monomers or comonomers), tetrapolymers (which usually refers to polymers prepared from four different types of monomers or comonomers), and the like. The terms "monomer" or "comonomer" are used interchangeably, and they refer to any compound with a polymerizable moiety which is added to a reactor in order to produce a polymer. In those instances in which a polymer is described as comprising one or more monomers, e.g., a polymer comprising propylene and ethylene, the polymer, of course, comprises units derived from the monomers, e.g., —CH$_2$—CH$_2$—, and not the monomer itself, e.g., CH$_2$=CH$_2$.

"Metallocene-catalyzed polymer" or similar term means any polymer that is made in the presence of a metallocene catalyst. "Constrained geometry catalyst catalyzed polymer", "CGC-catalyzed polymer" or similar term means any polymer that is made in the presence of a constrained geometry catalyst. "Ziegler-Natta-catalyzed polymer", Z-N-catalyzed polymer" or similar term means any polymer that is made in the presence of a Ziegler-Natta catalyst. "Metallocene" means a metal-containing compound having at least one substituted or unsubstituted cyclopentadienyl group bound to the metal. "Constrained geometry catalyst" or "CGC" as here used has the same meaning as this term is defined and described in U.S. Pat. Nos. 5,272,236 and 5,278,272.

"Random copolymer" means a copolymer in which the monomer is randomly distributed across the polymer chain. "Impact copolymer" means two or more polymers in which one polymer is dispersed in the other polymer, typically one polymer comprising a matrix phase and the other polymer comprising an elastomer phase. The matrix polymer is typically a crystalline polymer, e.g., polypropylene homopolymer or copolymer, and the polymer comprising the elastomer phase is typically a rubber or elastomer, e.g., an EP or an EPDM rubber. The polymer that forms the elastomer phase typically comprises between about 5 and about 50, preferably between about 10 and 45 and more preferably between about 10 and 40, weight percent of the impact polymer.

"Propylene homopolymer" and similar terms mean a polymer consisting solely or essentially all of units derived from propylene. "Polypropylene copolymer" and similar terms mean a polymer comprising units derived from propylene and ethylene and/or one or more unsaturated comonomers. The term "copolymer" includes terpolymers, tetrapolymers, etc.

The unsaturated comonomers used in the practice of this invention include, C$_{4-20}$ α-olefins, especially C$_{4-12}$ α-olefins such as 1-butene, 1-pentene, 1-hexene, 4-methyl-1-pentene, 1-heptene, 1-octene, 1-decene, 1-dodecene and the like; C$_{4-20}$ diolefins, preferably 1,3-butadiene, 1,3-pentadiene, norbornadiene, 5-ethylidene-2-norbornene (ENB) and dicyclopentadiene; C$_{8-40}$ vinyl aromatic compounds including sytrene, o-, m-, and p-methylstyrene, divinylbenzene, vinylbiphenyl, vinylnapthalene; and halogen-substituted $C_{8-40}$ vinyl aromatic compounds such as chlorostyrene and fluorostyrene. For purposes of this invention, ethylene is not included in the definition of unsaturated comonomers.

The propylene copolymers of this invention typically comprise units derived from propylene in an amount of at least about 60, preferably at least about 80 and more preferably at least about 85, wt % of the copolymer. The typical amount of units derived from ethylene in propylene/ethylene copolymers is at least about 0.1, preferably at least about 1 and more preferably at least about 5 wt %, and the maximum amount of units derived from ethylene present in these copolymers is typically not in excess of about 35, preferably not in excess of about 30 and more preferably not in excess of about 20, wt % of the copolymer. The amount of units derived from the unsaturated comonomer(s), if present, is typically at least about 0.01, preferably at least about 1 and more preferably at least about 5, wt %, and the typical maximum amount of units derived from the unsaturated comonomer(s) typically does not exceed about 35, preferably it does not exceed about 30 and more preferably it does not exceed about 20, wt % of the copolymer. The combined total of units derived from ethylene and any unsaturated comonomer typically does not exceed about 40, preferably it does not exceed about 30 and more preferably it does not exceed about 20, wt % of the copolymer.

The copolymers of this invention comprising propylene and one or more unsaturated comonomers (other than ethylene) also typically comprise units derived from propylene in an amount of at least about 60, preferably at least about 70 and more preferably at least about 80, wt % of the copolymer. The one or more unsaturated comonomers of the copolymer comprise at least about 0.1, preferably at least about 1 and more preferably at least about 3, weight percent, and the typical maximum amount of unsaturated comonomer does not exceed about 40, and preferably it does not exceed about 30, wt % of the copolymer.

$^{13}$C NMR

The copolymers of this invention are further characterized as having substantially isotactic propylene sequences. "Substantially isotactic propylene sequences" and similar terms mean that the sequences have an isotactic triad (mm) measured by $^{13}$C NMR of greater than about 0.85, preferably greater than about 0.90, more preferably greater than about 0.92 and most preferably greater than about 0.93. Isotactic triads are well known in the art and are described in, for example, U.S. Pat. No. 5,504,172 and WO 00/01745 which refer to the isotactic sequence in terms of a triad unit in the copolymer molecular chain determined by $^{13}$C NMR spectra. NMR spectra are determined as follows.

$^{13}$C NMR spectroscopy is one of a number of techniques known in the art of measuring comonomer incorporation into a polymer. An example of this technique is described for the determination of comonomer content for ethylene/α-olefin copolymers in Randall (Journal of Macromolecular Science, Reviews in Macromolecular Chemistry and Physics, C29 (2 & 3), 201–317 (1989)). The basic procedure for determining the comonomer content of an olefin interpolymer involves obtaining the $^{13}$C NMR spectrum under conditions where the intensity of the peaks corresponding to the different carbons in the sample is directly proportional to the total number of contributing nuclei in the sample. Methods for ensuring this proportionality are known in the art and involve allowance for sufficient time for relaxation after a pulse, the use of gated-decoupling techniques, relaxation agents, and the like. The relative intensity of a peak or group of peaks is obtained in practice from its computer-generated integral. After obtaining the spectrum and integrating the peaks, those peaks associated with the comonomer are assigned. This assignment can be made by reference to known spectra or literature, or by synthesis and analysis of model compounds, or by the use of isotopically labeled comonomer. The mole % comonomer can be determined by the ratio of the integrals corresponding to the number of moles of comonomer to the integrals corresponding to the number of moles of all of the monomers in the interpolymer, as described in Randall, for example.

The data is collected using a Varian UNITY Plus 400 MHz NMR spectrometer, corresponding to a $^{13}$C resonance frequency of 100.4 MHz. Acquisition parameters are selected to ensure quantitative $^{13}$C data acquisition in the presence of the relaxation agent. The data is acquired using gated $^1$H decoupling, 4000 transients per data file, a 7 sec pulse repetition delay, spectral width of 24,200 Hz and a file size of 32K data points, with the probe head heated to 130° C. The sample is prepared by adding approximately 3 mL of a 50/50 mixture of tetrachloroethane-d2/orthodichlorobenzene that is 0.025M in chromium acetylacetonate (relaxation agent) to 0.4 g sample in a 10 mm NMR tube. The headspace of the tube is purged of oxygen by displacement with pure nitrogen. The sample is dissolved and homogenized by heating the tube and its contents to 150° C. with periodic refluxing initiated by heat gun.

Following data collection, the chemical shifts are internally referenced to the mmmm pentad at 21.90 ppm.

For propylene/ethylene copolymers, the following procedure is used to calculate the percent ethylene in the polymer. Integral regions are determined as follows:

TABLE D

Integral Regions for Determining % Ethylene

| Region designation | Ppm |
|---|---|
| A | 44–49 |
| B | 36–39 |
| C | 32.8–34 |
| P | 31.0–30.8 |
| Q | Peak at 30.4 |
| R | Peak at 30 |
| F | 28.0–29.7 |
| G | 26–28.3 |
| H | 24–26 |
| I | 19–23 |

Region D is calculated as D=P−(G−Q)/2. Region E=R+Q+(G−Q)/2.

TABLE E

Calculation of Region D

PPP = (F + A − 0.5D)/2
PPE = D
EPE = C
EEE = (E − 0.5G)/2
PEE = G
PEP = H
Moles P = sum P centered triads
Moles E = sum E centered triads
Moles P = (B + 2A)/2
Moles E = (E + G + 0.5B + H)/2

C2 values are calculated as the average of the two methods above (triad summation and algebraic) although the two do not usually vary.

The mole fraction of propylene insertions resulting in regio-errors is calculated as one half of the sum of the two of methyls showing up at 14.6 and 15.7 ppm divided by the total methyls at 14–22 ppm attributable to propylene. The mole percent of the regio-error peaks is the mole fraction times 100.

Isotacticity at the triad level (mm) is determined from the integrals of the mm triad (22.70–21.28 ppm), the mr triad (21.28–20.67 ppm) and the rr triad (20.67–19.74). The mm isotacticity is determined by dividing the intensity of the mm triad by the sum of the mm, mr, and rr triads. For ethylene copolymers the mr region is corrected by subtracting 37.5–39 ppm integral. For copolymers with other monomers that produce peaks in the regions of the mm, mr, and rr triads, the integrals for these regions are similarly corrected by subtracting the intensity of the interfering peak using standard NMR techniques, once the peaks have been identified. This can be accomplished, for example, by analysis of a series of copolymers of various levels of monomer incorporation, by literature assignments, by isotopic labeling, or other means which are known in the art.

The $^{13}$C NMR peaks corresponding to a regio-error at about 14.6 and about 15.7 ppm are believed to be the result of stereoselective 2,1-insertion errors of propylene units into the growing polymer chain. In a typical polymer of this invention, these peaks are of about equal intensity, and they represent about 0.02 to about 7 mole percent of the propylene insertions into the homopolymer or copolymer chain. For some embodiments of this invention, they represent about 0.005 to about 20 mole % or more of the propylene insertions. In general, higher levels of regio-errors lead to a lowering of the melting point and the modulus of the polymer, while lower levels lead to a higher melting point and a higher modulus of the polymer.

It should be appreciated that the nature and level of comonomers other than propylene also control the melting point and modulus of the copolymer. In any particular application, it may be desirable to have either a high or low melting point or a high or low modulus modulus. The level of regio-errors can be controlled by several means, including the polymerization temperature, the concentration of propylene and other monomers in the process, the type of (co) monomers, and other factors. Various individual catalyst structures may inherently produce more or less regio-errors than other catalysts. For example, in Table A above, the propylene homopolymer prepared with Catalyst G has a higher level of regio-errors and a lower melting point than the propylene homopolymer prepared with Catalyst H, which has a higher melting point. If a higher melting point (or higher modulus) polymer is desired, then it is preferable to have fewer regio-errors than about 3 mole % of the propylene insertions, more preferably less than about 1.5 mole % of the propylene insertions, still more preferably less than about 1.0 mole % of the propylene insertions, and most preferably less than about 0.5 mole % of the propylene insertions. If a lower melting point (or modulus) polymer is desired, then it is preferable to have more regio-errors than about 3 mole % of the propylene insertions, more preferably more than about 5 mole % of the propylene insertions, still more preferably more than about 6 mole % of the propylene insertions, and most preferably more than about 10 mole % of the propylene insertions.

It should be appreciated by the skilled artisan that the mole % of regio-errors for an inventive polymer which is a component of a blend refers to the mole % of regio-errors of the particular inventive polymer component of the blend that is the particular inventive polymer, and not as a mole % of the overall blend.

Figure 6:
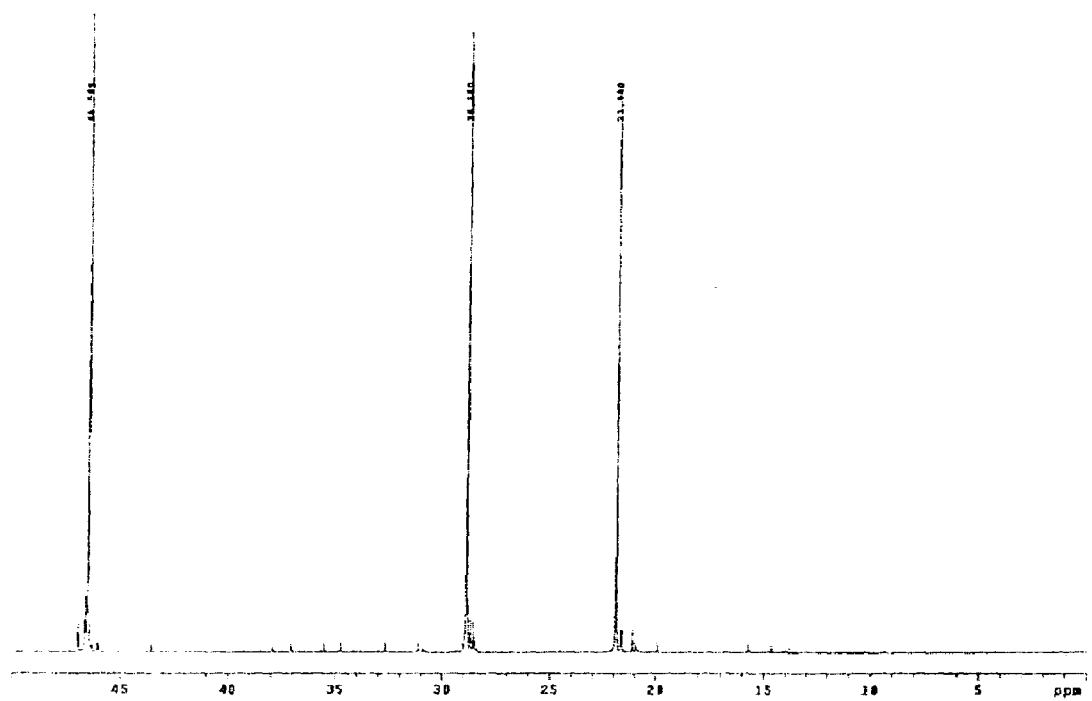
FIG. 6 shows the ¹³C NMR spectrum of the propylene homopolymer product of Example 7, prepared using Catalyst G. This spectrum shows the high degree of isotacticity of the product.
Figure 7:
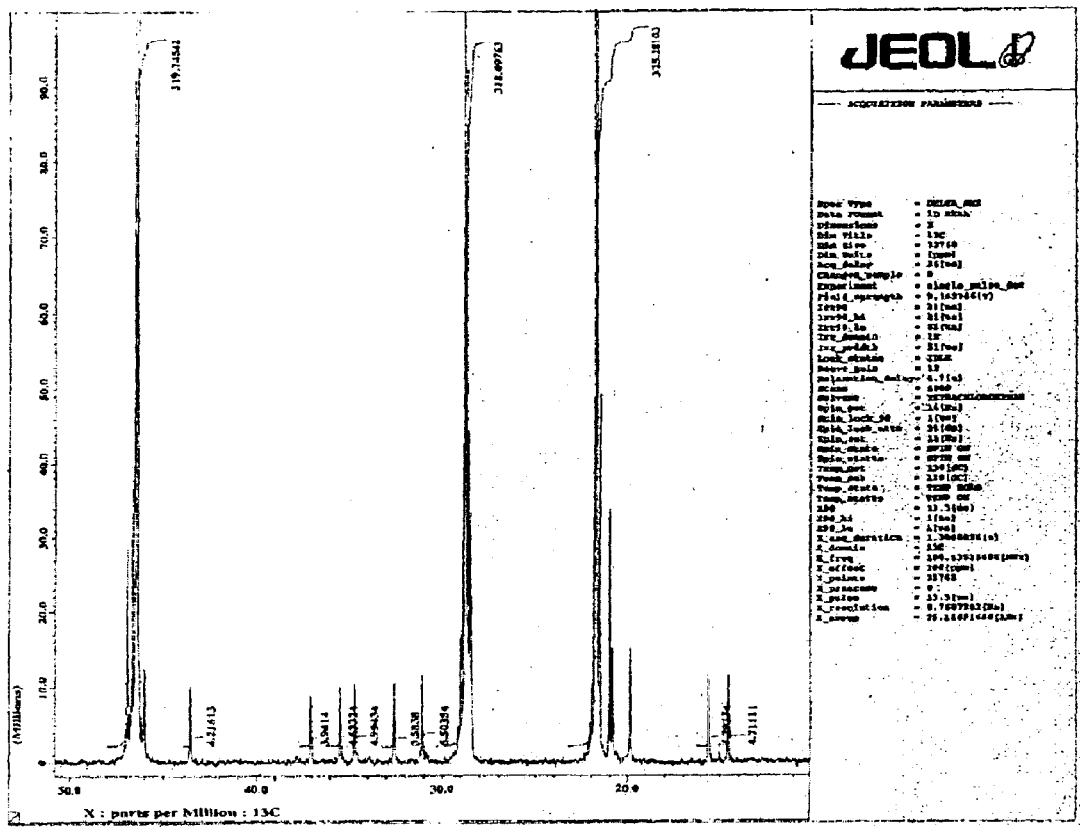
FIG. 7 shows the ¹³C NMR Spectrum of the propylene homopolymer product of Example 8, prepared using Catalyst H. This spectrum is shown at an expanded Y-axis scale relative to FIG. 6 in order to more clearly show the regio-error peaks.
Figure 8:
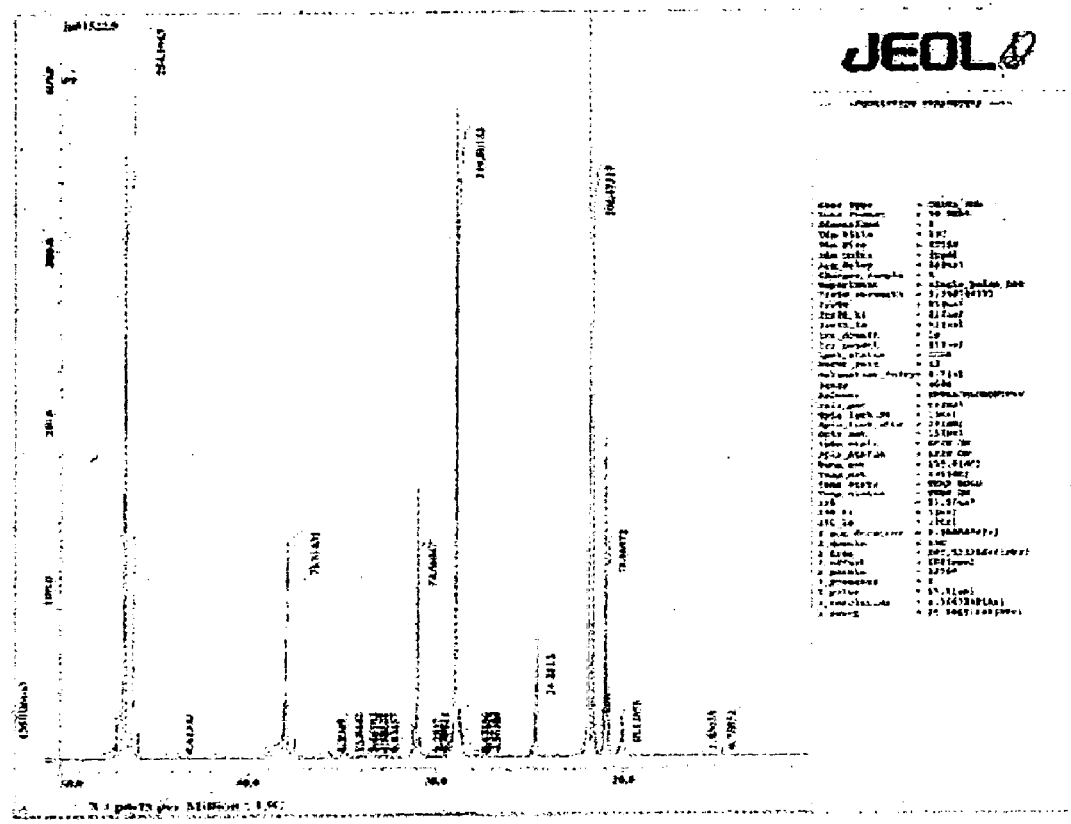
FIG. 8 shows the ¹³C NMR Spectrum of the P/E* copolymer product of Example 2 prepared using Catalyst G.
Figure 9:
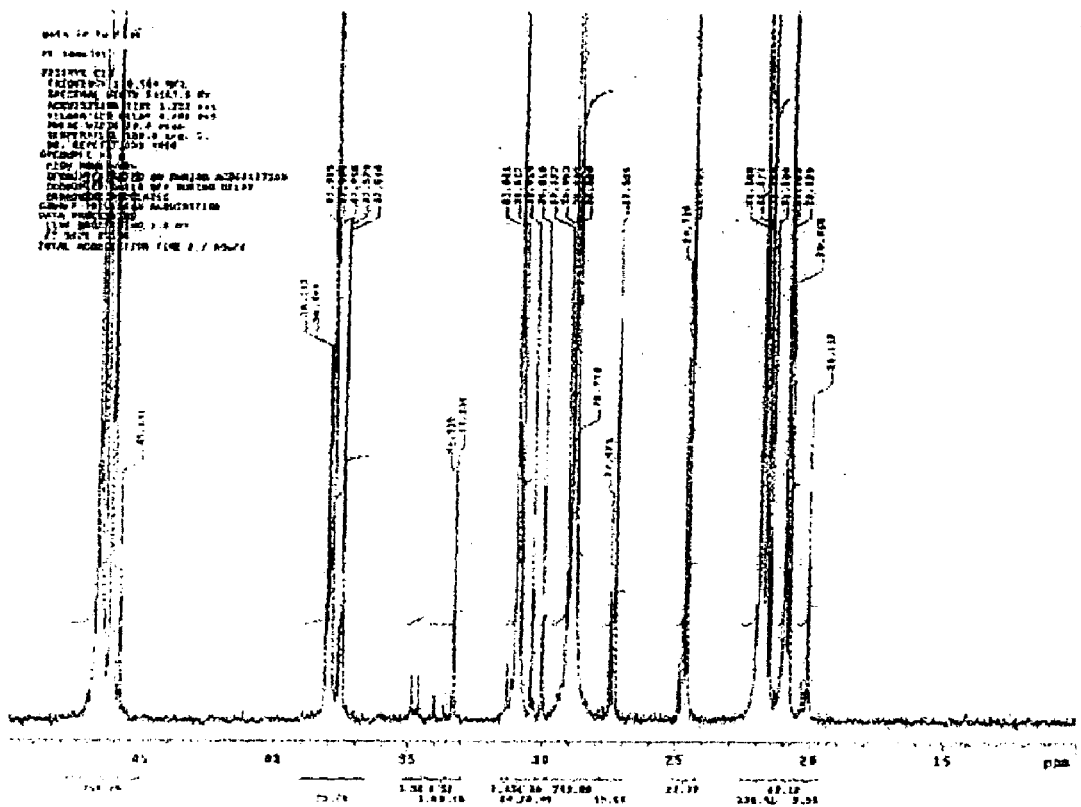
FIG. 9 shows the ¹³C NMR Spectrum of the P/E copolymer product of Comparative Example 1 prepared using metallocene Catalyst E demonstrating the absence of regio-error peaks in the region around 15 ppm.

The comparison of several $^{13}$C NMR sprectra further illustrates the unique regio-errors of the propylene polymers of this invention. FIGS. 6 and 7 are the spectra of the propylene homopolymer products of Examples 7 and 8, respectively, each made with an activated nonmetallocene, metal-centered, heteroaryl ligand catalyst. The spectrum of each polymer reports a high degree of isotacticity and the unique regio-errors of these inventive polymers. FIG. 8 is the $^{13}$C NMR spectrum of the propylene-ethylene copolymer of Example 2, made with the same catalyst used to make the propylene homopolymer of Example 7, and it too reports a high degree of isotacticity and the same regio-errors of the propylene homopolymers of FIGS. 9 and 10. The presence of the ethylene comonomer does not preclude the occurrence of these unique regio-errors. The $^{13}$C NMR spectrum of FIG. 9 is that of the propylene-ethylene copolymer product of Comparative Example 1 which was prepared using a metallocene catalyst. This spectrum does not report the regio-error (around 15 ppm) characteristic of the propylene polymers of this invention.

Melt Flow Rate (MFR)

The propylene copolymers of this invention typically have an MFR of at least about 0.01, preferably at least about 0.05, more preferably at least about 0.1 and most preferably at least about 0.2. The maximum MFR typically does not exceed about 1,000, preferably it does not exceed about 500, more preferably it does not exceed about 100, further more preferably it does not exceed about 80 and most preferably it does not exceed about 50. MFR for polypropylene and copolymers of propylene and ethylene and/or one or more $C_4$–$C_{20}$ α olefins is measured according to ASTM D-1238, condition L (2.16 kg, 230 degrees C.).

Propylene Copolymers

The propylene copolymers of this invention of particular interest include propylene/ethylene, propylene/1-butene, propylene/1-hexene, propylene/4-methyl-1-pentene, propylene/1-octene, propylene/ethylene/1-butene, propylene/ethylene/ENB, propylene/ethylene/1-hexene, propylene/ethylene/1-octene, propylene/styrene, and propylene/ethylene/styrene.

Catalyst Definitions and Descriptions

The propylene copolymers of this invention are prepared by a process comprising contacting under solution, slurry or gas phase polymerization conditions propylene and at least one of ethylene and one or more unsaturated monomers with a nonmetallocene, metal-centered, heteroaryl ligand catalyst. Propylene homopolymers are similarly prepared by a process comprising contacting under solution, slurry or gas phase polymerization conditions propylene with a nonmetallocene, metal-centered, heteroaryl ligand catalyst. "Nonmetallocene" means that the metal of the catalyst is not attached to a substituted or unsubstituted cyclopentadienyl ring. Representative nonmetallocene, metal-centered, heteroarly ligand catalysts are described in U.S. Provisional Patent Application Nos. 60/246,781 filed Nov. 7, 2000 and 60/301,666 filed Jun. 28, 2001.

As here used, "nonmetallocene, metal-centered, heteroaryl ligand catalyst" means the catalyst derived from the ligand described in formula I. As used in this phrase, "heteroaryl" includes substituted heteroaryl.

As used herein, the phrase "characterized by the formula" is not intended to be limiting and is used in the same way that "comprising" is commonly used. The term "independently selected" is used herein to indicate that the R groups, e.g., $R^1$, $R^2$, $R^3$, $R^4$, and $R^5$ can be identical or different (e.g. $R^1$, $R^2$, $R^3$, $R^4$, and $R^5$ may all be substituted alkyls or $R^1$ and $R^2$ may be a substituted alkyl and $R^3$ may be an aryl, etc.). Use of the singular includes use of the plural and vice ver-a (e.g., a hexane solvent, includes hexanes). A named R group will generally have the structure that is recognized in the art as corresponding to R groups having that name. The terms "compound" and "complex" are generally used interchangeably in this specification, but those of skill in the art may recognize certain compounds as complexes and vice versa. For the purposes of illustration, representative certain groups are defined herein. These definitions are intended to supplement and illustrate, not preclude, the definitions known to those of skill in the art.

"Hydrocarbyl" refers to univalent hydrocarbyl radicals containing 1 to about 30 carbon atoms, preferably 1 to about 24 carbon atoms, most preferably 1 to about 12 carbon atoms, including branched or unbranched, saturated or unsaturated species, such as alkyl groups, alkenyl groups, aryl groups, and the like. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom.

The term "alkyl" is used herein to refer to a branched or unbranched, saturated or unsaturated acyclic hydrocarbon radical. Suitable alkyl radicals include, for example, methyl, ethyl, n-propyl, i-propyl, 2-propenyl (or allyl), vinyl, n-butyl, t-butyl, i-butyl (or 2-methylpropyl), etc. In particular embodiments, alkyls have between 1 and 200 carbon atoms, between 1 and 50 carbon atoms or between 1 and 20 carbon atoms.

"Substituted alkyl" refers to an alkyl as just described in which one or more hydrogen atom bound to any carbon of the alkyl is replaced by another group such as a halogen, aryl, substituted aryl, cycloalkyl, substituted cycloalkyl, heterocycloalkyl, substituted heterocycloalkyl, halogen, alkylhalos (e.g., $CF_3$), hydroxy, amino, phosphido, alkoxy, amino, thio, nitro, and combinations thereof. Suitable substituted alkyls include, for example, benzyl, trifluoromethyl and the like.

The term "heteroalkyl" refers to an alkyl as described above in which one or more hydrogen atoms to any carbon of the alkyl is replaced by a heteroatom selected from the group consisting of N, O, P, B, S, Si, Sb, Al, Sn, As, Se and Ge. This same list of heteroatoms is useful throughout this specification. The bond between the carbon atom and the heteroatom may be saturated or unsaturated. Thus, an alkyl substituted with a heterocycloalkyl, substituted heterocycloalkyl, heteroaryl, substituted heteroaryl, alkoxy, aryloxy, boryl, phosphino, amino, silyl, thio, or seleno is within the scope of the term heteroalkyl. Suitable heteroalkyls include cyano, benzoyl, 2-pyridyl, 2-furyl and the like.

The term "cycloalkyl" is used herein to refer to a saturated or unsaturated cyclic non-aromatic hydrocarbon radical having a single ring or multiple condensed rings. Suitable cycloalkyl radicals include, for example, cyclopentyl, cyclohexyl, cyclooctenyl, bicyclooctyl, etc. In particular embodiments, cycloalkyls have between 3 and 200 carbon atoms, between 3 and 50 carbon atoms or between 3 and 20 carbon atoms.

"Substituted cycloalkyl" refers to cycloalkyl as just described including in which one or more hydrogen atom to any carbon of the cycloalkyl is replaced by another group such as a halogen, alkyl, substituted alkyl, aryl, substituted aryl, cycloalkyl, substituted cycloalkyl, heterocycloalkyl, substituted heterocycloalkyl, heteroaryl, substituted heteroaryl, alkoxy, aryloxy, boryl, phosphino, amino, silyl, thio, seleno and combinations thereof. Suitable substituted cycloalkyl radicals include, for example, 4-dimethyl-aminocyclohexyl, 4,5-dibromocyclohept-4-enyl, and the like.

The term "heterocycloalkyl" is used herein to refer to a cycloalkyl radical as described, but in which one or more or all carbon atoms of the saturated or unsaturated cyclic radical are replaced by a heteroatom such as nitrogen, phosphorous, oxygen, sulfur, silicon, germanium, selenium, or boron. Suitable heterocycloalkyls include, for example, piperazinyl, morpholinyl, tetrahydropyranyl, tetrahydrofuranyl, piperidinyl, pyrrolidinyl, oxazolinyl and the like.

"Substituted heterocycloalkyl" refers to heterocycloalkyl as just described including in which one or more hydrogen atom to any atom of the heterocycloalkyl is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Suitable substituted heterocycloalkyl radicals include, for example, N-methylpiperazinyl, 3-dimethylaminomorpholinyl and the like.

The term "aryl" is used herein to refer to an aromatic substituent which may be a single aromatic ring or multiple aromatic rings which are fused together, linked covalently, or linked to a common group such as a methylene or ethylene moiety. The aromatic ring(s) may include phenyl, naphthyl, anthracenyl, and biphenyl, among others. In particular embodiments, aryls have between 1 and 200 carbon atoms, between 1 and 50 carbon atoms or between 1 and 20 carbon atoms.

"Substituted aryl" refers to aryl as just described in which one or more hydrogen atom bound to any carbon is replaced by one or more functional groups such as alkyl, substituted alkyl, cycloalkyl, substituted cycloalkyl, heterocycloalkyl, substituted heterocycloalkyl, halogen, alkylhalos (e.g., $CF_3$), hydroxy, amino, phosphido, alkoxy, amino, thio, nitro, and both saturated and unsaturated cyclic hydrocarbons which are fused to the aromatic ring(s), linked covalently or linked to a common group such as a methylene or ethylene moiety. The common linking group may also be a carbonyl as in benzophenone or oxygen as in diphenylether or nitrogen in diphenylamine.

The term "heteroaryl" as used herein refers to aromatic or unsaturated rings in which one or more carbon atoms of the aromatic ring(s) are replaced by a heteroatom(s) such as nitrogen, oxygen, boron, selenium, phosphorus, silicon or sulfur. Heteroaryl refers to structures that may be a single aromatic ring, multiple aromatic ring(s), or one or more aromatic rings coupled to one or more non-aromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, pyrazole, pyrrole, furan, etc. or benzo-fused analogues of these rings are defined by the term "heteroaryl."

"Substituted heteroaryl" refers to heteroaryl as just described including in which one or more hydrogen atoms bound to any atom of the heteroaryl moiety is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Suitable substituted heteroaryl radicals include, for example, 4-N,N-dimethylaminopyridine.

The term "alkoxy" is used herein to refer to the —OZ$^1$ radical, where Z$^1$ is selected from the group consisting of alkyl, substituted alkyl, cycloalkyl, substituted cycloalkyl, heterocylcoalkyl, substituted heterocycloalkyl, silyl groups and combinations thereof as described herein. Suitable alkoxy radicals include, for example, methoxy, ethoxy, benzyloxy, t-butoxy, etc. A related term is "aryloxy" where Z$^1$ is selected from the group consisting of aryl, substituted aryl, heteroaryl, substituted heteroaryl, and combinations thereof. Examples of suitable aryloxy radicals include phenoxy, substituted phenoxy, 2-pyridinoxy, 8-quinalinoxy and the like.

As used herein the term "silyl" refers to the —SiZ$^1$Z$^2$Z$^3$ radical, where each of Z$^1$, Z$^2$, and Z$^3$ is independently selected from the group consisting of hydrogen, alkyl, substituted alkyl, cycloalkyl, heterocycloalkyl, heterocyclic, aryl, substituted aryl, heteroaryl, substituted heteroaryl, alkoxy, aryloxy, amino, silyl and combinations thereof.

As used herein the term "boryl" refers to the —BZ$^1$Z$^2$ group, where each of Z$^1$ and Z$^2$ is independently selected from the group consisting of hydrogen, alkyl, substituted alkyl, cycloalkyl, heterocycloalkyl, heterocyclic, aryl, substituted aryl, heteroaryl, substituted heteroaryl, alkoxy, aryloxy, amino, silyl and combinations thereof.

As used herein, the term "phosphino" refers to the group —PZ$^1$Z$^2$, where each of Z$^1$ and Z$^2$ is independently selected from the group consisting of hydrogen, substituted or unsubstituted alkyl, cycloalkyl, heterocycloalkyl, heterocyclic, aryl, substituted aryl, heteroaryl, silyl, alkoxy, aryloxy, amino and combinations thereof.

As used herein, the term "phosphine" refers to the group: PZ$^1$Z$^2$Z$^3$, where each of Z$^1$, Z$^3$ and Z$^2$ is independently selected from the group consisting of hydrogen, substituted or unsubstituted alkyl, cycloalkyl, heterocycloalkyl, heterocyclic, aryl, substituted aryl, heteroaryl, silyl, alkoxy, aryloxy, amino and combinations thereof.

The term "amino" is used herein to refer to the group —NZ$^1$Z$^2$, where each of Z$^1$ and Z$^2$ is independently selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "amine" is used herein to refer to the group: NZ$^1$Z$^2$Z$^3$, where each of Z$^1$, Z$^2$ and Z$^2$ is independently selected from the group consisting of hydrogen, alkyl, substituted alkyl, cycloalkyl, substituted cycloalkyl, heterocycloalkyl, substituted heterocycloalkyl, aryl (including pyridines), substituted aryl, heteroaryl, substituted heteroaryl, alkoxy, aryloxy, silyl and combinations thereof.

The term "thio" is used herein to refer to the group —SZ$^1$, where Z$^1$ is selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "seleno" is used herein to refer to the group —SeZ$^1$, where Z$^1$ is selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "saturated" refers to lack of double and triple bonds between atoms of a radical group such as ethyl, cyclohexyl, pyrrolidinyl, and the like.

The term "unsaturated" refers to the presence one or more double and/or triple bonds between atoms of a radical group such as vinyl, acetylide, oxazolinyl, cyclohexenyl, acetyl and the like.

Ligands

Suitable ligands useful in the catalysts used in the practice of this invention can be characterized broadly as monoanionic ligands having an amine and a heteroaryl or substituted heteroaryl group. The ligands of the catalysts used in the practice of this invention are referred to, for the purposes of this invention, as nonmetallocene ligands, and may be characterized by the following general formula:

(I)

wherein R$^1$ is very generally selected from the group consisting of alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl and combinations thereof. In many embodiments, R$^1$ is a ring having from 4–8 atoms in the ring generally selected from the group consisting of substituted cycloalkyl, substituted heterocycloalkyl, substituted aryl and substituted heteroaryl, such that R$^1$ may be characterized by the general formula:

(A)

where Q$^1$ and Q$^5$ are substituents on the ring ortho to atom E, with E being selected from the group consisting of carbon and nitrogen and with at least one of Q$^1$ or Q$^5$ being bulky (defined as having at least 2 atoms). Q$^1$ and Q$^5$ are independently selected from the group consisting of alkyl, substituted alkyl, cycloalkyl, substituted cycloalkyl, aryl, substituted aryl and silyl, but provided that Q$^1$ and Q$^5$ are not both methyl. Q"$_q$ represents additional possible substituents on the ring, with q being 1, 2, 3, 4 or 5 and Q" being selected from the group consisting of hydrogen, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxyl, aryloxyl, silyl, boryl, phosphino, amino, thio, seleno, halide, nitro, and combinations thereof. T is a bridging group selected group consisting of —CR$^2$R$^3$— and —SiR$^2$R$^3$— with R$^2$ and R$^3$ being independently selected from the group consisting of hydrogen, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxyl, aryloxyl, silyl, boryl, phosphino, amino, thio, seleno, halide, nitro, and combinations thereof. J" is generally selected from the group consisting of heteroaryl and substituted heteroaryl, with particular embodiments for particular reactions being described herein.

In a more specific embodiment, suitable nonmetallocene ligands useful in this invention may be characterized by the following general formula:

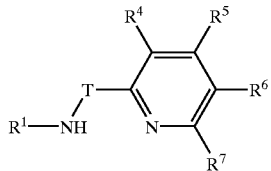

(II)

wherein $R^1$ and T are as defined above and each of $R^4$, $R^5$, $R^6$ and $R^7$ is independently selected from the group consisting of hydrogen, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxyl, aryloxyl, silyl, boryl, phosphino, amino, thio, seleno, halide, nitro, and combinations thereof. Optionally, any combination of $R^1$, $R^2$, $R^3$ and $R^4$ may be joined together in a ring structure.

In certain more specific embodiments, the ligands in this invention may be characterized by the following general formula:

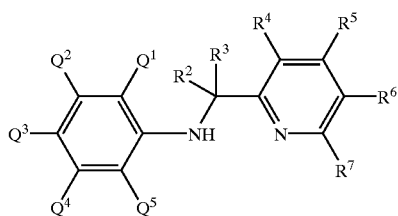

(III)

wherein $Q^1$, $Q^5$, $R^2$, $R^3$, $R^4$, $R^5$, $R^6$ and $R^7$ are as defined above. $Q^2$, $Q^3$ and $Q^4$ are independently selected from the group consisting of hydrogen, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxyl, aryloxyl, silyl, boryl, phosphino, amino, thio, seleno, nitro, and combinations thereof.

In other more specific embodiments, the ligands of this invention and suitable herein may be characterized by the following general formula:

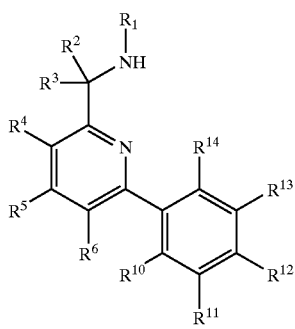

(IV)

wherein $R^1$, $R^2$, $R^3$, $R^4$, $R^5$, and $R^6$ are as defined above. In this embodiment the $R^7$ substituent has been replaced with an aryl or substituted aryl group, with $R^{10}$, $R^{11}$, $R^{12}$ and $R^{13}$ being independently selected from the group consisting of hydrogen, halo, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxy, aryloxy, silyl, boryl, phosphino, amino, thio, seleno, nitro, and combinations thereof; optionally, two or more $R^{10}$, $R^{11}$, $R^{12}$ and $R^{13}$ groups may be joined to form a fused ring system having from 3–50 non-hydrogen atoms. $R^{14}$ is selected from the group consisting of hydrogen, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxy, aryloxy, silyl, boryl, phosphino, amino, thio, seleno, halide, nitro, and combinations thereof.

In still more specific embodiments, the ligands in this invention may be characterized by the general formula:

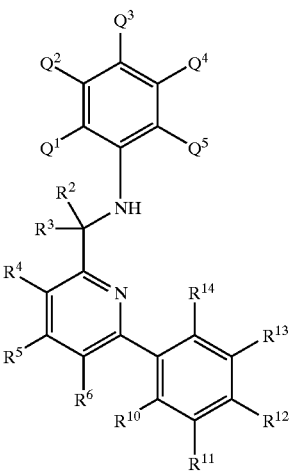

(V)

wherein $R^2$–$R^6$, $R^{10}$–$R^{14}$ and $Q^1$–$Q^5$ are all as defined above.

In certain embodiments, $R^2$ is preferably hydrogen. Also preferably, each of $R^4$ and $R^5$ is hydrogen and $R^6$ is either hydrogen or is joined to $R^7$ to form a fused ring system. Also preferred is where $R^3$ is selected from the group consisting of benzyl, phenyl, 2-biphenyl, t-butyl, 2-dimethylaminophenyl (2-(NMe$_2$)-C$_6$H$_4$—),2-methoxyphenyl (2-MeO—C$_6$H$_4$—), anthracenyl, mesityl, 2-pyridyl, 3,5-dimethylphenyl, o-tolyl, 9phenanthrenyl. Also preferred is where $R^1$ is selected from the group consisting of mesityl, 4-isopropylphenyl (4-Pr$^i$—C$_6$H$_4$—), napthyl, 3,5-(CF$_3$)$_2$—C$_6$H$_3$—, 2-Me-napthyl, 2,6-(Pr$^i$)$_2$—C$_6$H$_3$—, 2-biphenyl, 2-biphenyl, 2-Me-4-MeO-C$_6$H$_3$—; 2Bu$^t$-C$_6$H$_4$—, 2,5-(Bu$^t$)$_2$-C$_6$H$_3$—, 2-Pr$^i$-6-Me-C$_6$H$_3$—; 2-Bu$^t$-6-Me-C$_6$H$_3$—, 2,6-Et$_2$-C$_6$H$_3$—, 2-sec-butyl-6-Et-C$_6$H$_3$— Also preferred is where $R^7$ is selected from the group consisting of hydrogen, phenyl, napthyl, methyl, anthracenyl, 9-phenanthrenyl, mesityl, 3,5-(CF$_3$)$_2$—C$_6$H$_3$—, 2-CF$_3$—C$_6$H$_4$—, 4-CF$_3$—C$_6$H$_4$—, 3,5-F$_2$—C$_6$H$_3$—, 4-F—C$_6$H$_4$—, 2,4-F$_2$—C$_6$H$_3$—, 4-(NMe$_2$)-C$_6$H$_4$—, 3-MeO—C$_6$H$_4$—, 4-MeO—C$_6$H$_4$—, 3,5-Me$_2$-C$_6$H$_3$—, o-tolyl, 2,6-F$_2$—C$_6$H$_3$— or where $R^7$ is joined together with $R^6$ to form a fused ring system, e.g., quinoline.

Also optionally, two or more $R^4$, $R^5$, $R^6$, $R^7$ groups may be joined to form a fused ring system having from 3–50 non-hydrogen atoms in addition to the pyridine ring, e.g. generating a quinoline group. In these embodiments, $R^3$ is selected from the group consisting of aryl, substituted aryl, heteroaryl, substituted heteroaryl, primary and secondary alkyl groups, and —$PY_2$ where Y is selected from the group consisting of aryl, substituted aryl, heteroaryl, and substituted heteroaryl.

Optionally within above formulas IV and V, $R^6$ and $R^{10}$ may be joined to form a ring system having from 5–50 non-hydrogen atoms. For example, if $R^6$ and $R^{10}$ together form a methylene, the ring will have 5 atoms in the backbone of the ring, which may or may not be substituted with other atoms. Also for example, if $R^6$ and $R^{10}$ together form an ethylene, the ring will have 6 atoms in the backbone of the ring, which may or may not be substituted with other atoms. Substituents from the ring can be selected from the group consisting of halo, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxy, aryloxy, silyl, boryl, phosphino, amino, thio, seleno, nitro, and combinations thereof.

In certain embodiments, the ligands are novel compounds and those of skill in the art will be able to identify such compounds from the above. One example of the novel ligand compounds, includes those compounds generally characterized by formula (III), above where $R^2$ is selected from the group consisting of hydrogen, alkyl, substituted alkyl, cycloalkyl, substituted cycloalkyl, aryl, and substituted aryl; and $R^3$ is a phosphino characterized by the formula —$PZ^1Z^2$, where each of $Z^1$ and $Z^2$ is independently selected from the group consisting of hydrogen, substituted or unsubstituted alkyl, cycloalkyl, heterocycloalkyl, heterocyclic, aryl, substituted aryl, heteroaryl, silyl, alkoxy, aryloxy, amino and combinations thereof. Particularly preferred embodiments of these compounds include those where $Z^1$ and $Z^2$ are each independently selected from the group consisting of alkyl, substituted alkyl, cycloalkyl, heterocycloalkyl, aryl, and substituted aryl; and more specifically phenyl; where $Q^1$, $Q^3$, and $Q^5$ are each selected from the group consisting of alkyl and substituted alkyl and each of $Q^2$ and $Q^4$ is hydrogen; and where $R^4$, $R^5$, $R^6$ and $R^7$ are each hydrogen.

The ligands of the catalysts of this invention may be prepared using known procedures. See, for example, Advanced Organic Chemistry, March, Wiley, New York 1992 (4$^{th}$ Ed.). Specifically, the ligands of the invention may be prepared using the two step procedure outlined in Scheme 1.

Scheme 1

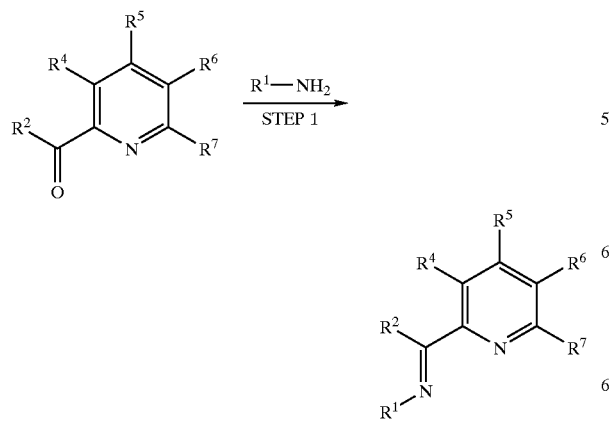

In Scheme 1, the * represents a chiral center when $R^2$ and $R^3$ are not identical; also, the R groups have the same definitions as above. Generally, $R^3M^2$ is a nucleophile such as an alkylating or arylating or hydrogenating reagent and $M^2$ is a metal such as a main group metal, or a metalloid such as boron. The alkylating, arylating or hydrogenating reagent may be a Grignard, alkyl, aryl-lithium or borohydride reagent. Scheme 1, step 2 first employs the use of complexing reagent. Preferably, as in the case of Scheme 1, magnesium bromide is used as the complexing reagent. The role of the complexing reagent is to direct the nucleophile, $R^3M^2$, selectively to the imine carbon. Where the presence of functional groups impede this synthetic approach, alternative synthetic strategies may be employed. For instance, ligands where $R^3$=phosphino can be prepared in accordance with the teachings of U.S. Pat. No. 6,034,240 and U.S. Pat. No. 6,043,363. In addition, tetra-alkylhafnium compounds or tetra-substituted alkylhafnium compounds or tetra-arylhafnium compounds or tetra-substituted arylhafnium compounds may be employed in step 2, in accordance with the teachings of U.S. Pat. No. 6,103,657. Scheme 2 further describes a synthesis process:

Scheme 2

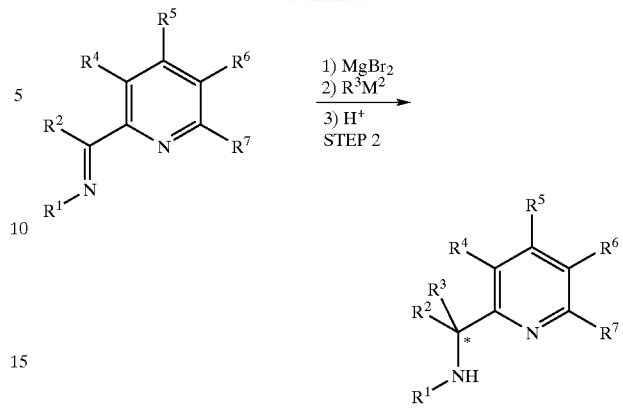

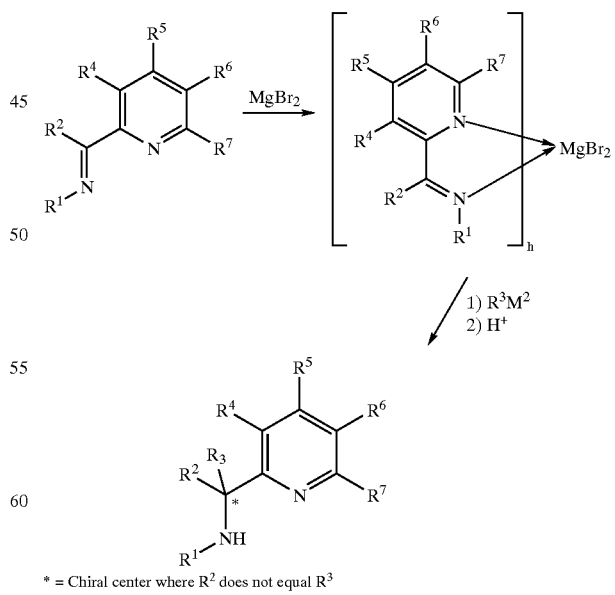

* = Chiral center where $R^2$ does not equal $R^3$

In scheme 2, h=1 or 2 and the bromine ions may or may not be bound to the magnesium. The effect of the complexation is to guide the subsequent nucleophilic attack by $R^3M^2$ to the imine carbon. Thus complexation may lead to a more selective reaction that may increase the yield of the desired ancillary ligands. Using this technique, selectivity is generally greater than about 50%, more preferably greater than about 70% and even more preferably greater than about 80%. Complexation may be particularly useful for the preparation of arrays of ancillary ligands of the type disclosed in the invention, where $R^3$ is a variable in the preparation of the ancillary ligand array. As shown in Scheme 2 by the *, where $R^2$ and $R^3$ are different, this approach also leads to the formation of a chiral center on the ancillary ligands of the invention. Under some circumstances $R^3M^2$ may be successfully added to the imine in the absence the complexing reagent. Ancillary ligands that possess chirality may be important in certain olefin polymerization reactions, particularly those that lead to a stereospecific polymer, see "Stereospecific Olefin Polymerization with Chiral Metallocene Catalysts", Brintzinger, et al., *Angew. Chem. Int. Ed. Engl.,* 1995, Vol. 34, pp. 1143–1170, and the references therein; Bercaw et al., *J. Am. Chem. Soc.,* 1999, Vol. 121, 564–573; and Bercaw et al., *J. Am. Chem. Soc.,* 1996, Vol. 118, 11988–11989.

In the practice of high throughput methods or combinatorial materials science, introduction of diversity may be important in designing libraries or arrays. The synthetic schemes discussed herein will allow those of skill in the art to introduce diversity on the ligands, which may assist in optimizing the selection of a particular ligand for a particular polymerization reaction. Step 1 (see Scheme 1) may be conducted with, for example, any combination of pyridines and anilines shown herein.

Compositions

Once the desired ligand is formed, it may be combined with a metal atom, ion, compound or other metal precursor compound. In some applications, the ligands of this invention will be combined with a metal compound or precursor and the product of such combination is not determined, if a product forms. For example, the ligand may be added to a reaction vessel at the same time as the metal or metal precursor compound along with the reactants, activators, scavengers, etc. Additionally, the ligand can be modified prior to addition to or after the addition of the metal precursor, e.g. through a deprotonation reaction or some other modification.

For formulas I, II, III, IV and V, the metal precursor compounds may be characterized by the general formula $Hf(L)_n$ where L is independently selected from the group consisting of halide (F, Cl, Br, I), alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, carboxylates, thio, 1,3-dionates, oxalates, carbonates, nitrates, sulphates, and combinations thereof. n is 1, 2, 3, 4, 5, or 6. The hafnium precursors may be monomeric, dimeric or higher orders thereof. It is well known that hafnium metal typically contains some amount of impurity of zirconium. Thus, this invention uses as pure hafnium as is commercially reasonable. Specific examples of suitable hafnium precursors include, but are not limited to $HfCl_4$, $Hf(CH_2Ph)_4$, $Hf(CH_2CMe_3)_4$, $Hf(CH_2SiMe_3)_4$, $Hf(CH_2Ph)_3Cl$, $Hf(CH_2CMe_3)_3Cl$, $Hf(CH_2SiMe_3)_3Cl$, $Hf(CH_2Ph)_2Cl_2$, $Hf(CH_2CMe_3)_2Cl_2$, $Hf(CH_2SiMe_3)_2Cl_2$, $Hf(NMe_2)_4$, $Hf(NEt_2)_4$, and $Hf(N(SiMe_3)_2)_2Cl_2$. Lewis base adducts of these examples are also suitable as hafnium precursors, for example, ethers, amines, thioethers, phosphines and the like are suitable as Lewis bases.

For formulas IV and V, the metal precursor compounds may be characterized by the general formula $M(L)_n$ where M is hafnium or zirconium and each L is independently selected from the group consisting of halide (F, Cl, Br, I), alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, carboxylates, thio, 1,3-dionates, oxalates, carbonates, nitrates, sulphates, and combinations thereof. n is 4, typically. It is well known that hafnium metal typically contains some amount of impurity of zirconium. Thus, this invention uses as pure hafnium or zirconium as is commercially reasonable. Specific examples of suitable hafnium and zirconium precursors include, but are not limited to $HfCl_4$, $Hf(CH_2Ph)_4$, $Hf(CH_2CMe_3)_4$, $Hf(CH_2SiMe_3)_4$, $Hf(CH_2Ph)_3Cl$, $Hf(CH_2CMe_3)_3Cl$, $Hf(CH_2SiMe_3)_3Cl$, $Hf(CH_2Ph)_2Cl_2$, $Hf(CH_2CMe_3)_2Cl_2$, $Hf(CH_2SiMe_3)_2Cl_2$, $Hf(NMe_2)_4$, $Hf(NEt_2)_4$, and $Hf(N(SiMe_3)_2)_2Cl_2$; $ZrCl_4$, $Zr(CH_2Ph)_4$, $Zr(CH_2CMe_3)_4$, $Zr(CH_2SiMe_3)_4$, $Zr(CH_2Ph)_3Cl$, $Zr(CH_2CMe_3)_3Cl$, $Zr(CH_2SiMe_3)_3Cl$, $Zr(CH_2Ph)_2Cl_2$, $Zr(CH_2CMe_3)_2Cl_2$, $Zr(CH_2SiMe_3)_2Cl_2$, $Zr(NMe_2)_4$, $Zr(NEt_2)_4$, $Zr(NMe_2)_2Cl_2$, $Zr(NEt_2)_2Cl_2$, and $Zr(N(SiMe_3)_2)_2Cl_2$. Lewis base adducts of these examples are also suitable as hafnium precursors, for example, ethers, amines, thioethers, phosphines and the like are suitable as Lewis bases.

The ligand to metal precursor compound ratio is typically in the range of about 0.01:1 to about 100:1, more preferably in the range of about 0.1:1 to about 10:1.

Metal-Ligand Complexes

This invention, in part, relates to the use of nonmetallocene metal-ligand complexes. Generally, the ligand is mixed with a suitable metal precursor compound prior to or simultaneously with allowing the mixture to be contacted with the reactants (e.g., monomers). When the ligand is mixed with the metal precursor compound, a metal-ligand complex may be formed, which may be a catalyst or may need to be activated to be a catalyst. The metal-ligand complexes discussed herein are referred to as 2,1 complexes or 3,2 complexes, with the first number representing the number of coordinating atoms and second number representing the charge occupied on the metal. The 2,1-complexes therefore have two coordinating atoms and a single anionic charge. Other embodiments of this invention are those complexes that have a general 3,2 coordination scheme to a metal center, with 3,2 referring to a ligand that occupies three coordination sites on the metal and two of those sites being anionic and the remaining site being a neutral Lewis base type coordination.

Looking first at the 2,1-nonmetallocene metal-ligand complexes, the metal-ligand complexes may be characterized by the following general formula:

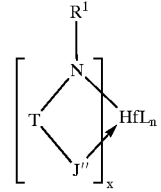

(VI)

wherein T, J", $R^1$, L and n are as defined previously; and x is 1 or 2. The J" heteroaryl may or may not datively bond, but is drawn as bonding. More specifically, the nonmetallocene-ligand complexes may be characterized by the formula:

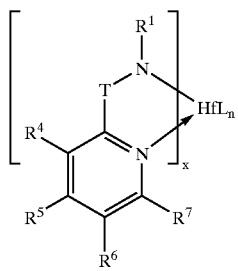

(VII)

wherein $R^1$, T, $R^4$, $R^5$, $R^6$, $R^7$, L and n are as defined previously; and x is 1 or 2. In one preferred embodiment x=1 and n=3. Additionally, Lewis base adducts of these metal-ligand complexes are also within the scope of the invention, for example, ethers, amines, thioethers, phosphines and the like are suitable as Lewis bases.

More specifically, the nonmetallocene metal-ligand complexes of this invention may be characterized by the general formula:

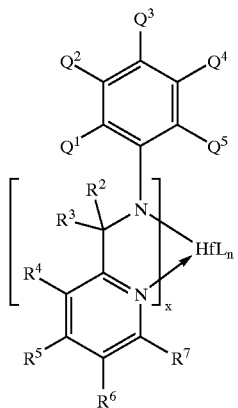

(VIII)

wherein the variables are generally defined above. Thus, e.g., $Q^2$, $Q^3$, $Q^4$, $R^2$, $R^3$, $R^4$, $R^5$, $R^6$ and $R^7$ are independently selected from the group consisting of hydrogen, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxyl, aryloxyl, silyl, boryl, phosphino, amino, thio, seleno, nitro, and combinations thereof, optionally, two or more $R^4$, $R^5$, $R^6$, $R^7$ groups may be joined to form a fused ring system having from 3–50 non-hydrogen atoms in addition to the pyridine ring, e.g. generating a quinoline group; also, optionally, any combination of $R^2$, $R^3$ and $R^4$ may be joined together in a ring structure; $Q^1$ and $Q^5$ are selected from the group consisting of alkyl, substituted alkyl, cycloalkyl, substituted cycloalkyl, aryl, substituted aryl, provided that $Q^1$ and $Q^5$ are not both methyl; and each L is independently selected from the group consisting of halide, alkyl, substituted alkyl, cycloalkyl, substituted cycloalkyl, heteroalkyl, substituted heteroalkyl heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, carboxylates, thio, 1,3-dionates, oxalates, carbonates, nitrates, sulphates and combinations thereof; n is 1,2,3,4,5, or 6; and x=1 or 2.

In other embodiments, the 2,1 metal-ligand complexes can be characterized by the general formula:

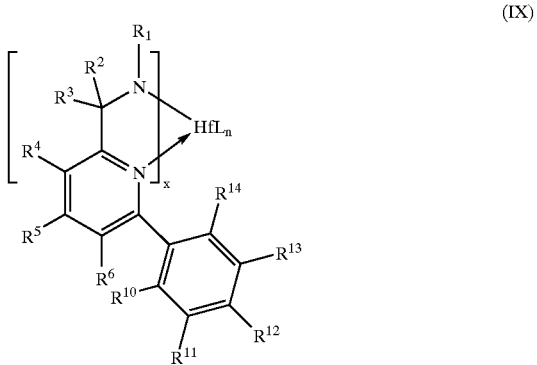

(IX)

wherein the variables are generally defined above.

In still other embodiments, the 2,1 metal-ligand complexes of this invention can be characterized by the general formula:

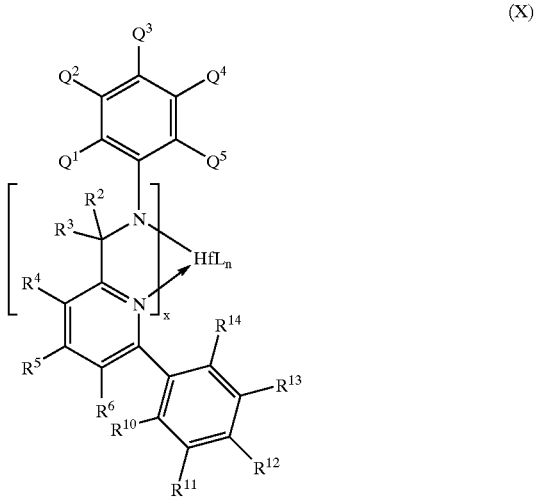

(X)

wherein the variables are generally defined above.

The more specific embodiments of the nonmetallocene metal-ligand complexes of formulas VI, VII, VIII, IX and X are explained above with regard to the specifics described for the ligands and metal precursors. Specific examples of 2,1 metal-ligand complexes include, but are not limited to:

-continued
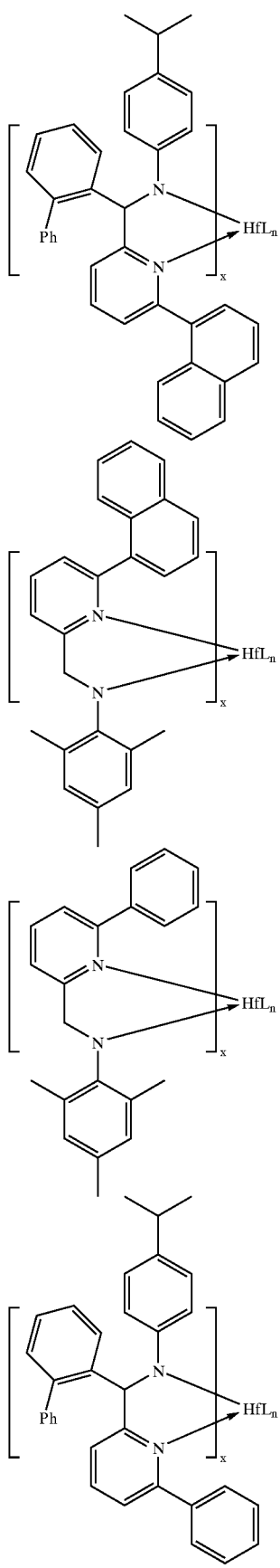
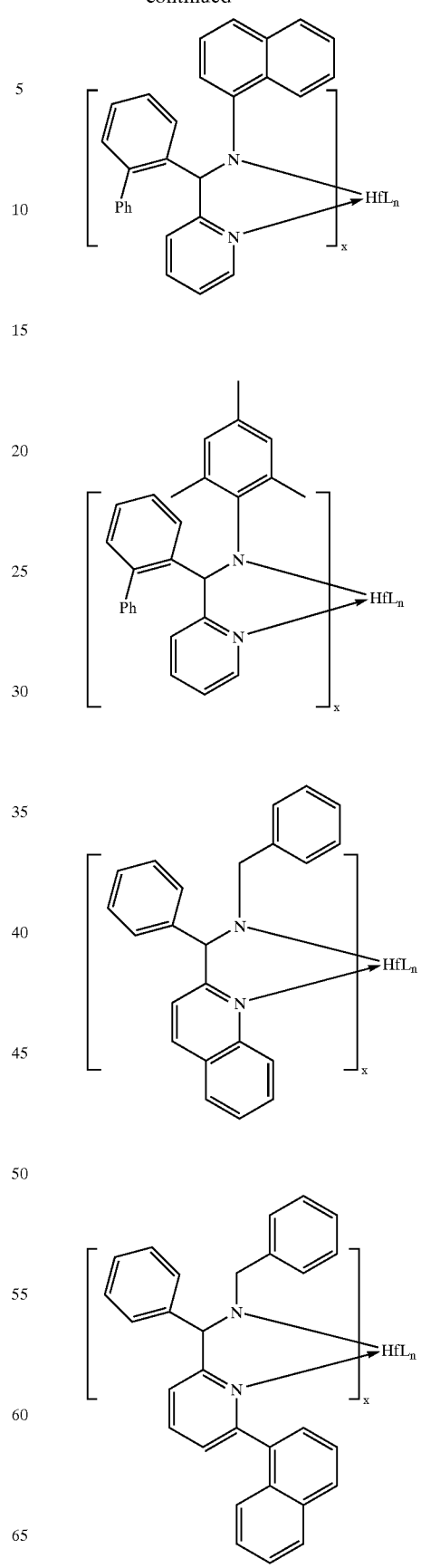

-continued

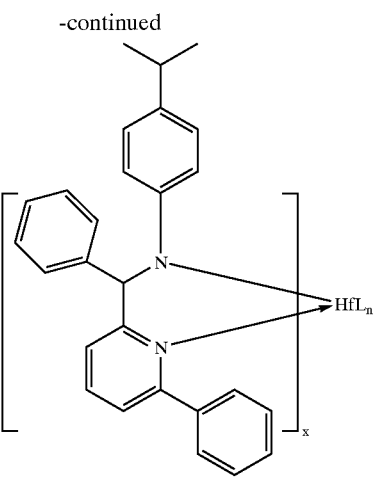

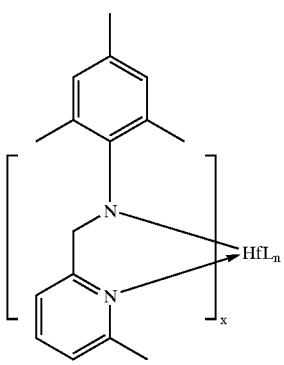

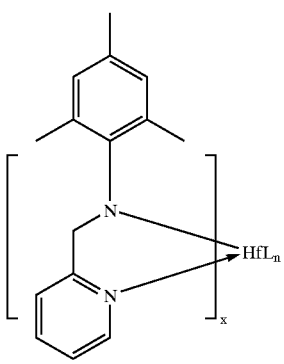

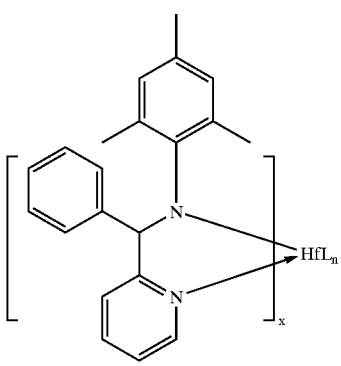

-continued

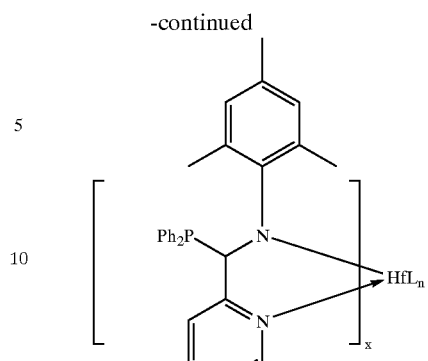

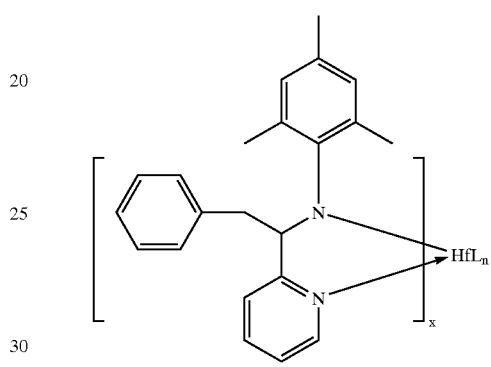

where L, n and x are defined as above (e.g., x=1 or 2) and Ph=phenyl. In preferred embodiments, x=1 and n=3. Furthermore in preferred embodiments, L is selected from the group consisting of alkyl, substituted alkyl, aryl, substituted aryl or amino.

Turning to the 3,2 metal-ligand nonmetallocene complexes used in the practice of this invention, the metal-ligand complexes may be characterized by the general formula:

(XI)

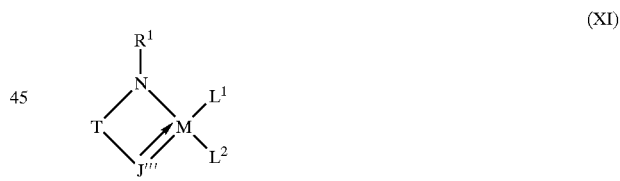

where M is zirconium or hafnium;

$R^1$ and T are defined above;

J''' being selected from the group of substituted heteroaryls with 2 atoms bonded to the metal M, at least one of those 2 atoms being a heteroatom, and with one atom of J''' is bonded to M via a dative bond, the other through a covalent bond; and $L^1$ and $L^2$ are independently selected from the group consisting of halide, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, carboxylates, thio, 1,3-dionates, oxalates, carbonates, nitrates, sulphates, and combinations thereof.

More specifically, the 3,2 metal-ligand nonmetallocene complexes of this invention may be characterized by the general formula:

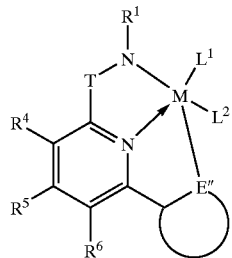

(XII)

where M is zirconium or hafnium;
T, $R^1$, $R^4$, $R^5$, $R^6$, $L^1$ and $L^2$ are defined above; and
E″ is either carbon or nitrogen and is part of an cyclic aryl, substituted aryl, heteroaryl, or substituted heteroaryl group.

Even more specifically, the 3,2 metal-ligand nonmetallocene complexes used in the practice of this invention may be characterized by the general formula:

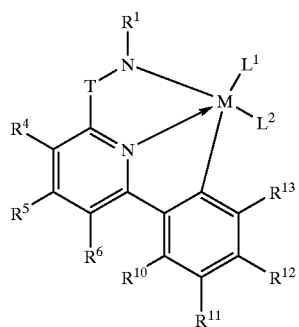

(XIII)

where M is zirconium or hafnium; and
T, $R^1$, $R^4$, $R^5$, $R^6$, $R^{10}$, $R^{11}$, $R^{12}$, $R^{13}$, $L^1$ and $L^2$ are defined above.

Still even more specifically, the 3,2 metal-ligand nonmetallocene complexes of this invention may be characterized by the general formula:

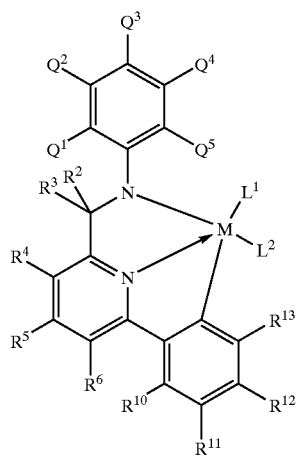

(XIV)

where M is zirconium or hafnium; and
T, $R^1$, $R^4$, $R^5$, $R^6$, $R^{10}$, $R^{11}$, $R^{12}$, $R^{13}$, $Q^1$, $Q^2$, $Q^3$, $Q^4$, $Q^5$, $L^1$ and $L^2$ are defined above.

The more specific embodiments of the metal-ligand complexes of formulas XI, XII, XIII and XIV are explained above with regard to the specifics described for the ligands and metal precursors.

In the above formulas, $R^{10}$, $R^{11}$, $R^{12}$ and $R^{13}$ are independently selected from the group consisting of hydrogen, halo, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxy, aryloxy, silyl, boryl, phosphino, amino, thio, seleno, nitro, and combinations thereof; optionally, two or more $R^{10}$, $R^{11}$, $R^{12}$ and $R^{13}$ groups may be joined to form a fused ring system having from 3–50 non-hydrogen atoms.

In addition, Lewis base adducts of the metal-ligand complexes in the above formulas are also suitable, for example, ethers, amines, thioethers, phosphines and the like are suitable as Lewis bases.

The metal-ligand complexes can be formed by techniques known to those of skill in the art. In some embodiments, $R^{14}$ is hydrogen and the metal-ligand complexes are formed by a metallation reaction (in situ or not) as shown below in scheme 3:

Scheme 3

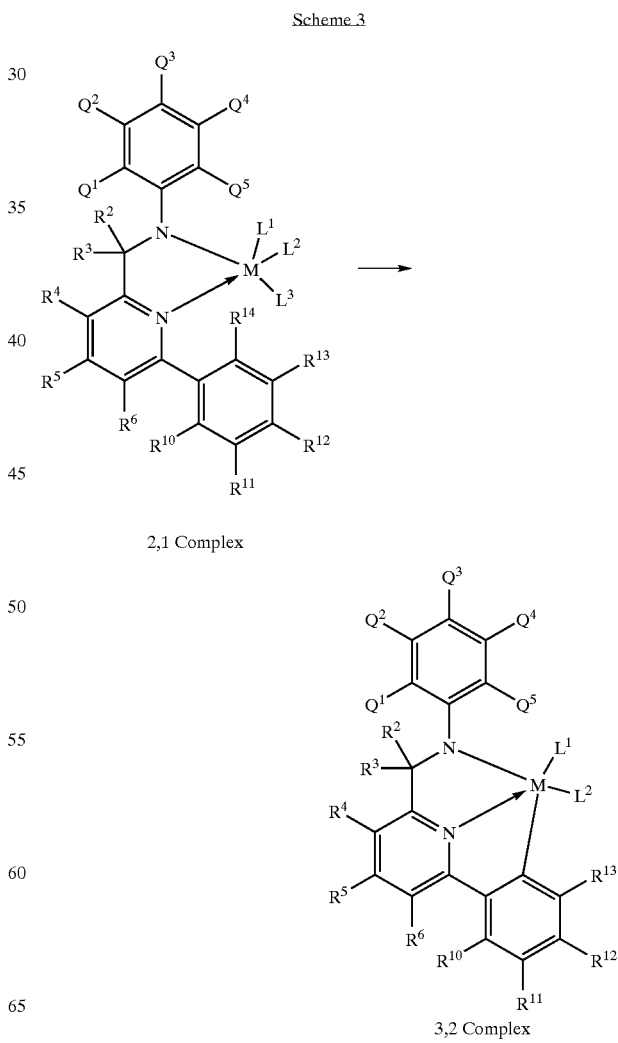

2,1 Complex 3,2 Complex

In scheme 3, $R^{14}$ is hydrogen (but see above for the full definition of R in other embodiments of this invention). The metallation reaction to convert the 2,1-complex on the left to the 3,2 complex on the right can occur via a number of mechanisms, likely depending on the substituents chosen for $L^1$, $L^2$ and $L^3$ and the other substituents such as $Q^1-Q^5$, $R^2-R^6$, $R^{10}$ to $R^{13}$. In one embodiment, when $L^1$, $L^2$ and $L^3$ are each $N(CH_3)_2$, the reaction can proceed by heating the 2,1 complex to a temperature above about 100° C. In this embodiment, it is believed that $L^1$ and $L^2$ remain $N(CH_3)_2$ in the 3,2 complex. In another embodiment where $L^1$, $L^2$ and $L^3$ are each $N(CH_3)_2$, the reaction can proceed by adding a group 13 reagent (as described below) to the 2,1 complex at a suitable temperature (such as room temperature). Preferably the group 13 reagent for this purpose is di-isobutyl aluminum hydride, tri-isobutyl aluminum or trimethyl aluminum. In this embodiment, $L^1$ and $L^2$ are typically converted to the ligand (e.g., alkyl or hydride) stemming from the group 13 reagent (e.g., from trimethyl aluminum, $L^1$ and $L^2$ are each $CH_3$ in the 3,2 complex). The 2,1 complex in scheme 3 is formed by the methods discussed above.

In an alternative embodiment possibly outside the scope of scheme 3, for isotactic polypropylene production, it is currently preferred that $R^{14}$ is either hydrogen or methyl.

Specific examples of 3,2 complexes of this invention include:

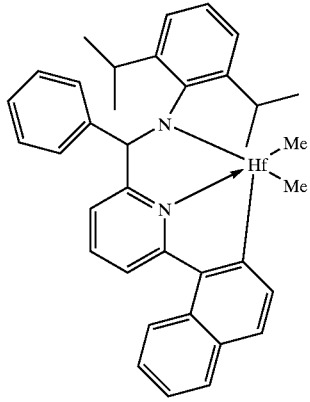

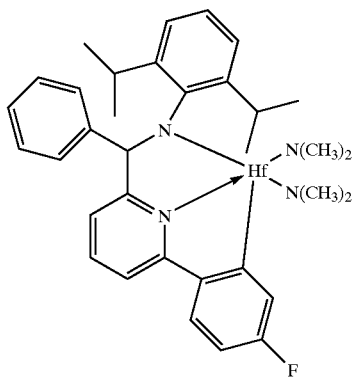

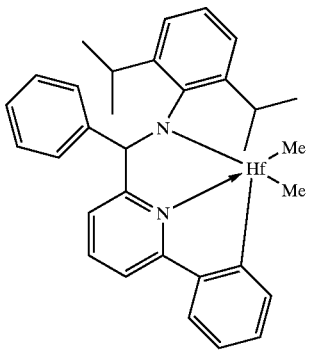

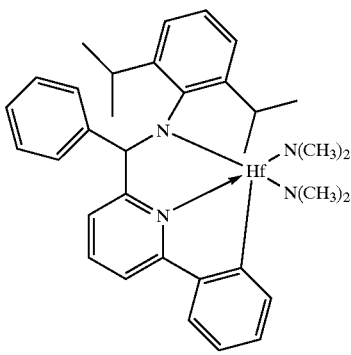

Various references disclose metal complexes that may appear to be similar; see for example, U.S. Pat. No. 6,103,657 and U.S. Pat. No. 5,637,660. However, certain embodiments of the invention herein provide unexpectedly improved polymerization performance (e.g., higher activity and/or higher polymerization temperatures and/or higher comonomer incorporation and/or crystalline polymers resulting from a high degree of stereoselectivity during polymerization) relative to the embodiments disclosed in those references. In particular, as shown in certain of the examples herein, the activity of the hafnium metal catalysts is far superior to that of the zirconium catalysts.

The ligands, complexes or catalysts may be supported on an organic or inorganic support. Suitable supports include silicas, aluminas, clays, zeolites, magnesium chloride, polyethyleneglycols, polystyrenes, polyesters, polyamides, peptides and the like. Polymeric supports may be cross-linked or not. Similarly, the ligands, complexes or catalysts may be supported on similar supports known to those of skill in the art. In addition, the catalysts of this invention may be combined with other catalysts in a single reactor and/or employed in a series of reactors (parallel or serial) in order to form blends of polymer products. Supported catalysts typically produce copolymers of this invention with an MWD larger than those produce from unsupported catalysts, although these MWDs are typically less about 6, preferably less than about 5 and more preferably less than about 4. While not wanting to be bound by any particular theory of operation, the unsupported catalysts typically produce P/E* polymers with a narrow MWD which suggests that the nonmetallocene, metal-centered, heteroaryl ligand catalysts used in the practice of this invention are "single-site" catalysts.

The metal complexes used in this invention are rendered catalytically active by combination with an activating cocatalyst or by use of an activating technique. Suitable activating cocatalysts for use herein include neutral Lewis acids such as alumoxane (modified and unmodified), $C_{1-30}$ hydrocarbyl substituted Group 13 compounds, especially tri(hydrocarbyl)aluminum- or tri(hydrocarbyl)boron compounds and halogenated (including perhalogenated) derivatives thereof, having from 1 to 10 carbons in each hydrocarbyl or halogenated hydrocarbyl group, more especially perfluorinated tri(aryl)boron compounds, and most especially tris(pentafluorophenyl)borane; nonpolymeric, compatible, noncoordinating, ion forming compounds (including the use of such compounds under oxidizing conditions), especially the use of ammonium-, phosphonium-, oxonium-, carbonium-, silylium- or sulfonium-salts of compatible, noncoordinating anions, or ferrocenium salts of compatible, noncoordinating anions; bulk electrolysis (explained in more detail hereinafter); and combinations of the foregoing activating cocatalysts and techniques. The foregoing activating cocatalysts and activating techniques have been previously taught with respect to different metal complexes in the following references: U.S. Pat. No. 5,153,157 and U.S. Pat. No. 5,064,802, EP-A-277,003, EP-A-468,651 (equivalent to U.S. Ser. No. 07/547,718), U.S. Pat. No. 5,721,185 and U.S. Pat. No. 5,350,723.

The alumoxane used as an activating cocatalyst in this invention is of the formula $(R^4{}_x(CH_3)_y AlO)_n$, in which $R^4$ is a linear, branched or cyclic $C_1$ to $C_6$ hydrocarbyl, x is from 0 to about 1, y is from about 1 to 0, and n is an integer from about 3 to about 25, inclusive. The preferred alumoxane components, referred to as modified methylaluminoxanes, are those wherein $R^4$ is a linear, branched or cyclic $C_3$ to $C_9$ hydrocarbyl, x is from about 0.15 to about 0.50, y is from about 0.85 to about 0.5 and n is an integer between 4 and 20, inclusive; still more preferably, $R^4$ is isobutyl, tertiary butyl or n-octyl, x is from about 0.2 to about 0.4, y is from about 0.8 to about 0.6 and n is an integer between 4 and 15, inclusive. Mixtures of the above alumoxanes may also be employed in the practice of the invention.

Most preferably, the alumoxane is of the formula $(R^4{}_x(CH_3)_y AlO)_n$, wherein $R^4$ is isobutyl or tertiary butyl, x is about 0.25, y is about 0.75 and n is from about 6 to about 8.

Particularly preferred alumoxanes are so-called modified alumoxanes, preferably modified methylalumoxanes (MMAO), that are completely soluble in alkane solvents, for example heptane, and may include very little, if any, trialkylaluminum. A technique for preparing such modified alumoxanes is disclosed in U.S. Pat. No. 5,041,584 (which is incorporated by reference). Alumoxanes useful as an activating cocatalyst in this invention may also be made as disclosed in U.S. Pat. Nos. 4,542,199; 4,544,762; 4,960,878; 5,015,749; 5,041,583 and 5,041,585. Various alumoxanes can be obtained from commercial sources, for example, Akzo-Nobel Corporation, and include MMAO-3A, MMAO-12, and PMAO-IP.

Combinations of neutral Lewis acids, especially the combination of a trialkyl aluminum compound having from 1 to 4 carbons in each alkyl group and a halogenated tri(hydrocarbyl)boron compound having from 1 to 10 carbons in each hydrocarbyl group, especially tris(pentafluorophenyl)borane, and combinations of neutral Lewis acids, especially tris(pentafluorophenyl)borane, with nonpolymeric, compatible noncoordinating ion-forming compounds are also useful activating cocatalysts.

Suitable ion forming compounds useful as cocatalysts in one embodiment of the present invention comprise a cation which is a Bronsted acid capable of donating a proton, and a compatible, noncoordinating anion, $A^-$. As used herein, the term "noncoordinating" means an anion or substance which either does not coordinate to the Group 4 metal containing precursor complex and the catalytic derivative derived therefrom, or which is only weakly coordinated to such complexes thereby remaining sufficiently labile to be displaced by a neutral Lewis base. A noncoordinating anion specifically refers to an anion which when functioning as a charge balancing anion in a cationic metal complex does not transfer an anionic substituent or fragment thereof to said cation thereby forming neutral complexes. "Compatible anions" are anions which are not degraded to neutrality when the initially formed complex decomposes and are noninterfering with desired subsequent polymerization or other uses of the complex.

Preferred anions are those containing a single coordination complex comprising a charge-bearing metal or metalloid core which anion is capable of balancing the charge of the active catalyst species (the metal cation) which may be formed when the two components are combined. Also, said anion should be sufficiently labile to be displaced by olefinic, diolefinic and acetylenically unsaturated compounds or other neutral Lewis bases such as ethers or nitrites. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

In one embodiment of this invention, the activating cocatalysts may be represented by the following general formula:

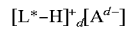

wherein:

L* is a neutral Lewis base;

[L*–H]$^+$ is a Bronsted acid;

$A^{d-}$ is a noncoordinating, compatible anion having a charge of d$^-$, and d is an integer from 1 to 3.

More preferably $A^{d-}$ corresponds to the formula: $[M'^{k+}Q_{n'}]^{d-}$ wherein:

k is an integer from 1 to 3;

n' is an integer from 2 to 6;

n'–k=d;

M' is an element selected from Group 13 of the Periodic Table of the Elements; and Q independently each occurrence is selected from hydride, dialkylamido, halide, hydrocarbyl, hydrocarbyloxy, halosubstituted-hydrocarbyl, halosubstituted hydrocarbyloxy, and halo substituted silylhydrocarbyl radicals (including perhalogenated hydrocarbyl-perhalogenated hydrocarbyloxy- and perhalogenated silylhydrocarbyl radicals), said Q having up to 20 carbons with the proviso that in not more than one occurrence is Q halide. Examples of suitable hydrocarbyloxide Q groups are disclosed in U.S. Pat. No. 5,296,433.

In a more preferred embodiment, d is one, i.e., the counter ion has a single negative charge and is $A^-$. Activating cocatalysts comprising boron which are particularly useful in the preparation of catalysts of this invention may be represented by the following general formula:

$$[L^*-H]^+[BQ_4]^-$$

wherein:

[L*–H]+ is as previously defined;

B is boron in an oxidation state of 3; and

Q is a hydrocarbyl-, hydrocarbyloxy-, fluorinated hydrocarbyl-, fluorinated hydrocarbyloxy- or fluorinated silylhydrocarbyl-group of up to 20 nonhydrogen atoms, with the proviso that in not more than one occasion is Q hydrocarbyl. Most preferably, Q is each occurrence a fluorinated aryl group, especially, a pentafluorophenyl group.

Illustrative, but not limiting, examples of boron compounds which may be used as an activating cocatalyst in the preparation of the catalysts of this invention are tri-substituted ammonium salts such as:

triethylammonium tetraphenylborate,
N,N-dimethylanilinium tetraphenylborate,
tripropylammonium tetrakis(pentafluorophenyl) borate,
N,N-dimethylanilinium n-butyltris(pentafluorophenyl) borate,
triethylammonium tetrakis(2,3,4,6-tetrafluorophenyl) borate,
N,N-diethylanilinium tetrakis(2,3,4,6-tetrafluorophenyl) borate, and
N,N-dimethyl-2,4,6-trimethylanilinium tetrakis(2,3,4,6-tetrafluorophenyl) borate;
dialkyl ammonium salts such as:
di-(i-propyl)ammonium tetrakis(pentafluorophenyl) borate, and
dicyclohexylammonium tetrakis(pentafluorophenyl) borate;
tri-substituted phosphonium salts such as:
triphenylphosphonium tetrakis(pentafluorophenyl) borate,
tri(o-tolyl)phosphonium tetrakis(pentafluorophenyl) borate, and
tri(2,6-dimethylphenyl)phosphonium tetrakis (pentafluorophenyl) borate;
di-substituted oxonium salts such as:
diphenyloxonium tetrakis(pentafluorophenyl) borate,
di(o-tolyl)oxonium tetrakis(pentafluorophenyl) borate, and
di(2,6-dimethylphenyl)oxonium tetrakis(pentafluorophenyl) borate;
di-substituted sulfonium salts such as:
diphenylsulfonium tetrakis(pentafluorophenyl) borate,
di(o-tolyl)sulfonium tetrakis(pentafluorophenyl) borate, and
di(2,6-dimethylphenyl)sulfonium tetrakis(pentafluorophenyl) borate.

Preferred [L*–H]+ cations are N,N-dimethylanilinium and tributylammonium.

Another suitable ion forming, activating cocatalyst comprises a salt of a cationic oxidizing agent and a noncoordinating, compatible anion represented by the formula:

$$(Ox^{e+})_d(A^{d-})_e$$

wherein:

$Ox^{e+}$ is a cationic oxidizing agent having a charge of $e^+$;

e is an integer from 1 to 3; and $A^{d-}$ and d are as previously defined.

Examples of cationic oxidizing agents include: ferrocenium, hydrocarbyl-substituted ferrocenium, $Ag^+$, or $Pb^{+2}$. Preferred embodiments of $A^{d-}$ are those anions previously defined with respect to the Bronsted acid containing activating cocatalysts, especially tetrakis(pentafluorophenyl) borate.

Another suitable ion forming, activating cocatalyst comprises a compound which is a salt of a carbenium ion and a noncoordinating, compatible anion represented by the formula:

$$©^+A^-$$

wherein:

©+ is a $C_{1-20}$ carbenium ion; and $A^-$ is as previously defined.

A preferred carbenium ion is the trityl cation, i.e., triphenylmethylium.

A further suitable ion forming, activating cocatalyst comprises a compound which is a salt of a silylium ion and a noncoordinating, compatible anion represented by the formula:

$$R_3Si(X')_q{}^+A^-$$

wherein:

R is $C_{1-10}$ hydrocarbyl, and X', q and $A^-$ are as previously defined.

Preferred silylium salt activating cocatalysts are trimethylsilylium tetrakis(pentafluorophenyl)borate, triethylsilylium (tetrakispentafluoro)phenylborate and ether substituted adducts thereof. Silylium salts have been previously generically disclosed in *J. Chem Soc. Chem. Comm.*, 1993, 383–384, as well as Lambert, J. B., et al., *Organometallics*, 1994, 13, 2430–2443.

Certain complexes of alcohols, mercaptans, silanols, and oximes with tris(pentafluorophenyl)borane are also effective catalyst activators and may be used according to the present invention. Such cocatalysts are disclosed in U.S. Pat. No. 5,296,433.

The technique of bulk electrolysis involves the electrochemical oxidation of the metal complex under electrolysis conditions in the presence of a supporting electrolyte comprising a noncoordinating, inert anion. In the technique, solvents, supporting electrolytes and electrolytic potentials for the electrolysis are used such that electrolysis byproducts that would render the metal complex catalytically inactive are not substantially formed during the reaction. More particularly, suitable solvents are materials that are: liquids under the conditions of the electrolysis (generally temperatures from 0 to 100 C.), capable of dissolving the supporting electrolyte, and inert. "Inert solvents" are those that are not reduced or oxidized under the reaction conditions employed for the electrolysis. It is generally possible in view of the desired electrolysis reaction to choose a solvent and a supporting electrolyte that are unaffected by the electrical potential used for the desired electrolysis. Preferred solvents include difluorobenzene (all isomers), dimethoxyethane (DME), and mixtures thereof.

The electrolysis may be conducted in a standard electrolytic cell containing an anode and cathode (also referred to as the working electrode and counter electrode respectively). Suitable materials of construction for the cell are glass, plastic, ceramic and glass coated metal. The electrodes are prepared from inert conductive materials, by which are meant conductive materials that are unaffected by the reaction mixture or reaction conditions. Platinum or palladium are preferred inert conductive materials. Normally an ion permeable membrane such as a fine glass frit separates the cell into separate compartments, the working electrode compartment and counter electrode compartment. The working electrode is immersed in a reaction medium comprising the metal complex to be activated, solvent, supporting electrolyte, and any other materials desired for moderating the electrolysis or stabilizing the resulting complex. The counter electrode is immersed in a mixture of the solvent and supporting electrolyte. The desired voltage may be determined by theoretical calculations or experimentally by sweeping the cell using a reference electrode such as a silver electrode immersed in the cell electrolyte. The background cell current, the current draw in the absence of the desired electrolysis, is also determined. The electrolysis is completed when the current drops from the desired level to the background level. In this manner, complete conversion of the initial metal complex can be easily detected.

Suitable supporting electrolytes are salts comprising a cation and a compatible, noncoordinating anion, $A^-$. Preferred supporting electrolytes are salts corresponding to the formula:

$$G^+ A^-$$

wherein:

G$^+$ is a cation which is nonreactive towards the starting and resulting complex, and A$^-$ is as previously defined.

Examples of cations, G$^+$, include tetrahydrocarbyl substituted ammonium or phosphonium cations having up to 40 nonhydrogen atoms. Preferred cations are the tetra-n-butylammonium- and tetraethylammonium-cations.

During activation of the complexes of the present invention by bulk electrolysis the cation of the supporting electrolyte passes to the counter electrode and A$^-$ migrates to the working electrode to become the anion of the resulting oxidized product. Either the solvent or the cation of the supporting electrolyte is reduced at the counter electrode in equal molar quantity with the amount of oxidized metal complex formed at the working electrode. Preferred supporting electrolytes are tetrahydrocarbylammonium salts of tetrakis(perfluoroaryl) borates having from 1 to 10 carbons in each hydrocarbyl or perfluoroaryl group, especially tetra-n-butylammonium tetrakis(pentafluorophenyl) borate.

A further discovered electrochemical technique for generation of activating cocatalysts is the electrolysis of a disilane compound in the presence of a source of a noncoordinating compatible anion. This technique is more fully disclosed and claimed in U.S. Pat. No. 5,625,087.

The foregoing activating techniques and ion forming cocatalysts are also preferably used in combination with a tri(hydrocarbyl)aluminum or tri(hydrocarbyl)borane compound having from 1 to 4 carbons in each hydrocarbyl group.

The molar ratio of catalyst/cocatalyst employed preferably ranges from 1:10,000 to 100:1, more preferably from 1:5000 to 10:1, most preferably from 1:100 to 1:1. In one embodiment of the invention the cocatalyst can be used in combination with a tri(hydrocarbyl)aluminum compound having from 1 to 10 carbons in each hydrocarbyl group. Mixtures of activating cocatalysts may also be employed. It is possible to employ these aluminum compounds for their beneficial ability to scavenge impurities such as oxygen, water, and aldehydes from the polymerization mixture. Preferred aluminum compounds include trialkyl aluminum compounds having from 1 to 6 carbons in each alkyl group, especially those wherein the alkyl groups are methyl, ethyl, propyl, isopropyl, n-butyl, isobutyl, pentyl, neopentyl or isopentyl. The molar ratio of metal complex to aluminum compound is preferably from 1:10,000 to 100:1, more preferably from 1:1000 to 10:1, most preferably from 1:500 to 1:1. A most preferred borane activating cocatalyst comprises a strong Lewis acid, especially tris (pentafluorophenyl)borane.

In some embodiments disclosed herein, two or more different catalysts, including the use of mixed catalysts can be employed. In addition to a nonmetallocene, metal-centered, heteroaryl ligand catalyst, when a plurality of catalysts are used, any catalyst which is capable of copolymerizing one or more olefin monomers to make an interpolymer or homopolymer may be used in embodiments of the invention in conjunction with a nonmetallocene, metal-centered, heteroaryl ligand catalyst. For certain embodiments, additional selection criteria, such as molecular weight capability and/or comonomer incorporation capability, preferably should be satisfied. Two or more nonmetallocene, metal-centered, heteroaryl ligand catalysts having different substituents can be used in the practice of certain of the embodiments disclosed herein. Suitable catalysts which may be used in conjunction with the nonmetallocene, metal-centered, heteroaryl ligand catalysts disclosed herein include, but are not limited to, metallocene catalysts and constrained geometry catalysts, multi-site catalysts (Ziegler-Natta catalysts), and variations therefrom. They include any known and presently unknown catalysts for olefin polymerization. It should be understood that the term "catalyst" as used herein refers to a metal-containing compound which is used, along with an activating cocatalyst, to form a catalyst system. The catalyst, as used herein, is usually catalytically inactive in the absence of a cocatalyst or other activating technique. However, not all suitable catalysts are catalytically inactive without a cocatalyst One suitable class of catalysts is the constrained geometry catalysts disclosed in U.S. Pat. No. 5,064,802, U.S. Pat. No. 5,132,380, U.S. Pat. No. 5,703,187, U.S. Pat. No. 6,034,021, EP 0 468 651, EP 0 514 828, WO 93/19104, and WO 95/00526, all of which are incorporated by references herein in their entirety. Another suitable class of catalysts is the metallocene catalysts disclosed in U.S. Pat. No. 5,044,438; U.S. Pat. No. 5,057,475; U.S. Pat. No. 5,096,867; and U.S. Pat. No. 5,324,800, all of which are incorporated by reference herein in their entirety. It is noted that constrained geometry catalysts may be considered as metallocene catalysts, and both are sometimes referred to in the art as single-site catalysts.

Another suitable class of catalysts is substituted indenyl containing metal complexes as disclosed in U.S. Pat. No. 5,965,756 and U.S. Pat. No. 6,015,868. Other catalysts are disclosed in U.S. Pat Nos. 6,268,444 and 6,515,155 and in U.S. Ser. Nos. 60/215,456, 60/170,175, and 60/393,862. The disclosures of all of the preceding patents and patent applications are incorporated by reference herein in their entirety. These catalysts tend to have a higher molecular weight capability.

Other catalysts, cocatalysts, catalyst systems, and activating techniques which may be used in the practice of the invention disclosed herein may include those disclosed in WO 96/23010, published on Aug. 1, 1996, the entire disclosure of which is hereby incorporated by reference; those disclosed in WO 99/14250, published Mar. 25, 1999, the entire disclosure of which is hereby incorporated by reference; those disclosed in WO 98/41529, published Sep. 24, 1998, the entire disclosure of which is hereby incorporated by reference; those disclosed in WO 97/42241, published Nov. 13, 1997, the entire disclosure of which is hereby incorporated by reference; those disclosed by Scollard, et al., in J. Am. Chem. Soc 1996, 118, 10008–10009, the entire disclosure of which is hereby incorporated by reference; those disclosed in EP 0 468 537 B1, published Nov. 13, 1996, the entire disclosure of which is hereby incorporated by reference; those disclosed in WO 97/22635, published Jun. 26, 1997, the entire disclosure of which is hereby incorporated by reference; those disclosed in EP 0 949 278 A2, published Oct. 13, 1999, the entire disclosure of which is hereby incorporated by reference; those disclosed in EP 0 949 279 A2, published Oct. 13, 1999, the entire disclosure of which is hereby incorporated by reference; those disclosed in EP 1 063 244 A2, published Dec. 27, 2000, the entire disclosure of which is hereby incorporated by reference; those disclosed in U.S. Pat. No. 5,408,017, the entire disclosure of which is hereby incorporated by reference; those disclosed in U.S. Pat. No. 5,767,208, the entire disclosure of which is hereby incorporated by reference; those disclosed in U.S. Pat. No. 5,907,021, the entire disclosure of which is hereby incorporated by reference; those disclosed in WO 88/05792, published Aug. 11, 1988, the entire disclosure of which is hereby incorporated by reference; those disclosed in WO88/05793, published Aug. 11, 1988, the entire disclosure of which is hereby incorporated by reference; those disclosed in WO 93/25590, published Dec. 23, 1993, the entire disclosure of which is hereby incorporated by reference; those disclosed in U.S. Pat. No. 5,599,761, the entire disclosure of which is hereby incorporated by reference; those disclosed in U.S. Pat. No. 5,218,071, the entire disclosure of which is hereby incorporated by reference; those disclosed in WO 90/07526, published Jul. 12, 1990, the entire disclosure of which is hereby incorporated by reference; those disclosed in U.S. Pat. No. 5,972,822, the entire disclosure of which is hereby incorporated by reference; those disclosed in U.S. Pat. No. 6,074,977, the entire disclosure of which is hereby incorporated by reference; those disclosed in U.S. Pat. No. 6,013,819, the entire disclosure of which is hereby incorporated by reference; those disclosed in U.S. Pat. No. 5,296,433, the entire disclosure of which is hereby incorporated by reference; those disclosed in U.S. Pat. No. 4,874,880, the entire disclosure of which is hereby incorporated by reference; those disclosed in U.S. Pat. No. 5,198,401, the entire disclosure of which is hereby incorporated by reference; those disclosed in U.S. Pat. No. 5,621,127, the entire disclosure of which is hereby incorporated by reference; those disclosed in U.S. Pat. No. 5,703,257, the entire disclosure of which is hereby incorporated by reference; those disclosed in U.S. Pat. No. 5,728,855, the entire disclosure of which is hereby incorporated by reference; those disclosed in U.S. Pat. No. 5,731,253, the entire disclosure of which is hereby incorporated by reference; those disclosed in U.S. Pat. No. 5,710,224, the entire disclosure of which is hereby incorporated by reference; those disclosed in U.S. Pat. No. 5,883,204, the entire disclosure of which is hereby incorporated by reference; those disclosed in U.S. Pat. No. 5,504,049, the entire disclosure of which is hereby incorporated by reference; those disclosed in U.S. Pat. No. 5,962,714, the entire disclosure of which is hereby incorporated by reference; those disclosed in U.S. Pat. No. 5,965,677, the entire disclosure of which is hereby incorporated by reference; those disclosed in U.S. Pat. No. 5,427,991, the entire disclosure of which is hereby incorporated by reference; those disclosed in WO 93/21238, published Oct. 28, 1993, the entire disclosure of which is hereby incorporated by reference; those disclosed in WO 94/03506, published Feb. 17, 1994, the entire disclosure of which is hereby incorporated by reference; those disclosed in WO 93/21242, published Oct. 28, 1993, the entire disclosure of which is hereby incorporated by reference; those disclosed in WO 94/00500, published Jan. 6, 1994, the entire disclosure of which is hereby incorporated by reference; those disclosed in WO 96/00244, published Jan. 4, 1996, the entire disclosure of which is hereby incorporated by reference; those disclosed in WO 98/50392, published Nov. 12, 1998, the entire disclosure of which is hereby incorporated by reference; those disclosed in Wang, et al., Organometallics 1998, 17, 3149–3151, the entire disclosure of which is hereby incorporated by reference; those disclosed in Younkin, et al., Science 2000, 287, 460–462, the entire disclosure of which is hereby incorporated by reference; those disclosed by Chen and Marks, Chem. Rev. 2000, 100, 1391–1434, the entire disclosure of which is hereby incorporated by reference; those disclosed by Alt and Koppl, Chem. Rev. 2000, 100, 1205–1221, the entire disclosure of which is hereby incorporated by reference; those disclosed by Resconi, et al., Chem. Rev. 2000, 100, 1253–1345, the entire disclosure of which is hereby incorporated by reference; those disclosed by Ittel, et al., ChemRev. 2000, 100, 1169–1203, the entire disclosure of which is hereby incorporated by reference; those disclosed by Coates, Chem. Rev., 2000, 100, 1223–1251, the entire disclosure of which is hereby incorporated by reference; those disclosed by Brady, III, et al., U.S. Pat. No. 5,093,415, the entire disclosure of which is hereby incorporated by reference, those disclosed by Murray, et al., U.S. Pat. No. 6,303,719, the entire disclosure of which is hereby incorporated by reference, those disclosed by Saito, et al., U.S. Pat. No. 5,874,505, the entire disclosure of which is hereby incorporated by reference; and those disclosed in WO 96/13530, published May 9, 1996, the entire disclosure of which is hereby incorporated by reference. Also useful are those catalysts, cocatalysts, and catalyst systems disclosed in U.S. Ser. No. 09/230,185, filed Jan. 15, 1999; U.S. Pat. No. 5,965,756; U.S. Pat. No. 6,150,297; U.S. Ser. No. 09/715,380, filed Nov. 17, 2000.

Process Descriptions

In one embodiment, the process reagents, i.e., (i) propylene, (ii) ethylene and/or one or more unsaturated comonomers, (iii) catalyst, and, (iv) optionally, solvent and/or a molecular weight regulator (e.g., hydrogen), are fed to a single reaction vessel of any suitable design, e.g., stirred tank, loop, fluidized-bed, etc. The process reagents are contacted within the reaction vessel under appropriate conditions (e.g., solution, slurry, gas phase, suspension, high pressure) to form the desired polymer, and then the output of the reactor is recovered for post-reaction processing. All of the output from the reactor can be recovered at one time (as in the case of a single pass or batch reactor), or it can be recovered in the form of a bleed stream which forms only a part, typically a minor part, of the reaction mass (as in the case of a continuous process reactor in which an output stream is bled from the reactor at the same rate at which reagents are added to maintain the polymerization at steady-state conditions). "Reaction mass" means the contents within a reactor, typically during or subsequent to polymerization. The reaction mass includes reactants, solvent (if any), catalyst, and products and by-products. The recovered solvent and unreacted monomers can be recycled back to the reaction vessel.

The polymerization conditions at which the reactor is operated are similar to those for the polymerization of propylene using a known, conventional Ziegler-Natta catalyst. Typically, solution polymerization of propylene is performed at a polymerization temperature between about −50 to about 200, preferably between about −10 and about 150, C., and more preferably between about 20 to about 150 C. and most preferably between about 80 and 150 C., and the polymerization pressure is typically between about atmospheric to about 7, preferably between about 0.2 and about 5, Mpa. If hydrogen is present, then it is usually present at a partial pressure (as measured in the gas phase portion of the polymerization) of about 0.1 kPa to about 5 Mpa, preferably between about 1 kPa to about 3 Mpa. Gas phase, suspension and other polymerization schemes will use conditions conventional for those schemes. For gas-phase or slurry-phase polymerization processes, it is desirable to perform the polymerization at a temperature below the melting point of the polymer.

For the propylene/ethylene copolymer processes described herein, optionally containing additional unsaturated monomer, the weight ratio of propylene to ethylene in the feed to the reactors is preferably in the range of 10,000:1 to 1;10, more preferably 1,000:1 to 1:1, still more preferably 500:1 to 3:1. For the propylene/$C_{4-20}$ α-olefin copolymer processes of the present invention, the weight ratio of propylene to $C_{4-20}$ α-olefin in the feed preferably is in the range of 110,000:1 to 1:20, more preferably 1,000:1 to 1:1, still more preferably 1,000:1 to 3:1.

The post-reactor processing of the recover reaction mass from the polymerization vessel typically includes the deactivation of the catalyst, removal of catalyst residue, drying of the product, and the like. The recovered polymer is then ready for storage and/or use.

The propylene copolymer produced in a single reaction vessel in accordance with this invention will have the desired MFR, narrow MWD, $^{13}C$ NMR peaks at 14.6 and 15.7 ppm (the peaks of approximately equal intensity), a high B-value, and its other defining characteristics. If, however, a broader MWD is desired, e.g., a MWD of between about 2.5 and about 3.5 or even higher, without any substantial change to the other defining characteristics of the propylene copolymer, then the copolymer is preferably made in a multiple reactor system. In multiple reactor systems, MWD as broad as 15, more preferably 10, most preferably 4–8, can be prepared.

Preferably, to obtain a broad MWD, at least two of the catalysts used in a single reactor have a high weight-average molecular weight ($M_{wH}$)/low weight average molecular weight ($M_{wL}$) ratio ($M_{wH}/M_{wL}$, as defined later) in the range from about 1.5 to about 10, and the process used is a gas phase, slurry, or solution process. More preferably, at least two of the catalysts used in a single reactor have $M_{wH}/M_{wL}$ in the range from about 1.5 to about 10, and the process used is a continuous solution process, especially a continuous solution process wherein the polymer concentration in the reactor at steady state is at least 15% by weight of the reactor contents. Still more preferably, at least two of the catalysts used in a single reactor have $M_{wH}/M_{wL}$ in the range from about 1.5 to about 10, and the process used is a continuous solution process wherein the polymer concentration in the reactor at steady state is at least 18% by weight of the reactor contents. Most preferably, at least two of the catalysts used in a single reactor have $M_{wH}/M_{wL}$ in the range from about 1.5 to about 10, and the process used is a continuous solution process wherein the polymer concentration in the reactor at steady state is at least 20% by weight of the reactor contents.

In one embodiment, the monomers comprise propylene and at least one olefin selected from the group consisting of $C_4$–$C_{10}$ α-olefins, especially 1-butene, 1-hexene, and 1-octene, and the melt flow rate (MFR) of the interpolymer is preferably in the range of about 0.1 to about 500, more preferably in the range from about 0.1 to about 100, further more preferably about 0.2 to 80, most preferably in the range of 0.3–50. In some embodiments, the nonmetallocene, catalysts used in the practice of the invention described herein may be utilized in combination with at least one additional homogeneous or heterogeneous polymerization catalyst in separate reactors connected in series or in parallel to prepare polymer blends having desirable properties. An example of such a process is disclosed in WO 94/00500, equivalent to U.S. Ser. No. 07/904,770, as well as U.S. Ser. No. 08/10958, filed Jan. 29, 1993. Included in these embodiments is the use of two different nonmetallocene, metal-centered, heteroaryl ligand catalysts.

The catalyst system may be prepared as a homogeneous catalyst by addition of the requisite components to a solvent in which polymerization will be carried out by solution polymerization procedures. The catalyst system may also be prepared and employed as a heterogeneous catalyst by adsorbing the requisite components on a catalyst support material such as silica gel, alumina or other suitable inorganic support material. When prepared in heterogeneous or supported form, it is preferred to use silica as the support material. The heterogeneous form of the catalyst system may be employed in a slurry or gas phase polymerization. As a practical limitation, slurry polymerization takes place in liquid diluents in which the polymer product is substantially insoluble. Preferably, the diluent for slurry polymerization is one or more hydrocarbons with less than 5 carbon atoms. If desired, saturated hydrocarbons such as ethane, propane or butane may be used in whole or part as the diluent. Likewise the α-olefin comonomer or a mixture of different α-olefin comonomers may be used in whole or part as the diluent. Most preferably, the major part of the diluent comprises at least the α-olefin monomer or monomers to be polymerized.

Solution polymerization conditions utilize a solvent for the respective components of the reaction. Preferred solvents include, but are not limited to, mineral oils and the various hydrocarbons which are liquid at reaction temperatures and pressures. Illustrative examples of useful solvents include, but are not limited to, alkanes such as pentane, iso-pentane, hexane, heptane, octane and nonane, as well as mixtures of alkanes including kerosene and Isopar E™, available from Exxon Chemicals Inc.; cycloalkanes such as cyclopentane, cyclohexane, and methylcyclohexane; and aromatics such as benzene, toluene, xylenes, ethylbenzene and diethylbenzene.

At all times, the individual ingredients, as well as the catalyst components, should be protected from oxygen and moisture. Therefore, the catalyst components and catalysts should be prepared and recovered in an oxygen and moisture free atmosphere. Preferably, therefore, the reactions are performed in the presence of a dry, inert gas such as, for example, nitrogen or argon.

The polymerization may be carried out as a batch or a continuous polymerization process. A continuous process is preferred, in which event catalysts, solvent or diluent (if employed), and comonomers (or monomer) are continuously supplied to the reaction zone and polymer product continuously removed therefrom. The polymerization conditions for manufacturing the interpolymers according to embodiments of the invention are generally those useful in the solution polymerization process, although the application is not limited thereto. Gas phase and slurry polymerization processes are also believed to be useful, provided the proper catalysts and polymerization conditions are employed.

In some embodiments, the polymerization is conducted in a continuous solution polymerization system comprising two or more reactors connected in series or parallel. A catalyst solution comprising a nonmetallocene, metal-centered, heteroaryl ligand catalyst as described previously is used to polymerize propylene and optionally additional olefin monomers in at least one reactor. In one reactor, a relatively high molecular weight product ($M_w$ from 100,000 to over 1,000,000, more preferably 200,000 to 500,000) is formed while in the second or subsequent reactor(s) a product of a relatively low molecular weight ($M_w$ 2,000 to 300,000) is formed. The final product is a mixture of the two reactor effluents which are combined prior to devolatilization to result in a uniform mixing of the two polymer products. Such a dual reactor/dual catalyst process allows for the preparation of products with tailored properties.

In one embodiment, the reactors are connected in series, that is the effluent from the first reactor is charged to the second reactor and fresh monomer(s), solvent and hydrogen is added to the second reactor. Reactor conditions are adjusted such that the weight ratio of polymer produced in the first reactor to that produced in the second reactor typically from about 20:80 to about 80:20. Preferably, the weight ratio of polymer produced in the first reactor to that produced in the second reactor is from about 25:75 to about 75:25, more preferably from about 30:70 to about 70:30.

One representative example of a series polymerization is the preparation of propylene copolymer in which in the first reactor, propylene, ethylene, solvent and catalyst are contacted under solution phase conditions such that the propylene and ethylene copolymerize to form propylene copolymer. The catalyst used in the practice of this invention, however, is highly active and under appropriate conditions, converts 50% or more of the propylene and virtually all of the ethylene to the copolymer. Consequently when the contents, i.e., reaction mass, of the first reactor is transferred to the second reactor, most, if not all, of the polymer made in the second reactor is propylene homopolymer due to the absence or near absence of ethylene comonomer to the second reactor. One skill in the art understands that many variations on this theme are possible by replacing ethylene with, or using in combination with ethylene, one or more unsaturated comonomers; using a second but related catalyst in the second reactor; etc.

In one embodiment, the second reactor in a series polymerization process contains a heterogeneous Ziegler-Natta catalyst or chrome catalyst known in the art. Examples of Ziegler-Natta catalysts include, but are not limited to, titanium-based catalysts supported on $MgCl_2$, and additionally comprise compounds of aluminum containing at least one aluminum-alkyl bond. Suitable Ziegler Natta catalysts and their preparation include, but are not limited to, those disclosed in U.S. Pat. Nos. 4,612,300, 4,330,646 and 5,869,575. In another embodiment of the present invention, the second reactor in a series polymerization process contains a constrained geometry or a bis-Cp metallocene catalyst.

In another embodiment of this invention, propylene/ethylene copolymers are prepared in high yield and productivity. The process employed to make these copolymers may be either a solution or slurry process both of which are known in the art. Kaminsky, *J. Poly. Sci.,* Vol. 23, pp. 2151–64 (1985) reported the use of a soluble bis (cyclopentadienyl) zirconium dimethyl-alumoxane catalyst system for solution polymerization of propylene/ethylene (PE) elastomers. U.S. Pat. No. 5,229,478 discloses a slurry polymerization process utilizing similar bis (cyclopentadienyl) zirconium based catalyst systems.

The following procedure may be carried out to obtain a P/E* copolymer: In a stirred-tank reactor propylene monomer is introduced continuously together with solvent, and ethylene monomer. The reactor contains a liquid phase composed substantially of ethylene and propylene monomers together with any solvent or additional diluent. If desired, a small amount of a "H"-branch inducing diene such as norbornadiene, 1,7-octadiene or 1,9-decadiene may also be added. A nonmetallocene, metal-centered, heteroaryl ligand catalyst and suitable cocatalyst are continuously introduced in the reactor liquid phase. The reactor temperature and pressure may be controlled by adjusting the solvent/monomer ratio, the catalyst addition rate, as well as by cooling or heating coils, jackets or both. The polymerization rate is controlled by the rate of catalyst addition. The ethylene content of the polymer product is determined by the ratio of ethylene to propylene in the reactor, which is controlled by manipulating the respective feed rates of these components to the reactor. The polymer product molecular weight is controlled, optionally, by controlling other polymerization variables such as the temperature, monomer concentration, or by a stream of hydrogen introduced to the reactor, as is known in the art. The reactor effluent is contacted with a catalyst kill agent, such as water. The polymer solution is optionally heated, and the polymer product is recovered by flashing off unreacted gaseous ethylene and propylene as well as residual solvent or diluent at reduced pressure, and, if necessary, conducting further devolatilization in equipment such as a devolatilizing extruder or other devolatilizing equipment operated at reduced pressure. For a solution polymerization process, especially a continuous solution polymerization, preferred ranges of propylene concentration at steady state are from about 0.05 weight percent of the total reactor contents to about 50 weight percent of the total reactor contents, more preferably from about 0.5 weight percent of the total reactor contents to about 30 weight percent of the total reactor contents, and most preferably from about 1 weight percent of the total reactor contents to about 25 weight percent of the total reactor contents. The preferred range of polymer concentration (otherwise known as % solids) is from about 3% of the reactor contents by weight to about 45% of the reactor contents or higher, more preferably from about 10% of the reactor contents to about 40% of the reactor contents, and most preferably from about 15% of the reactor contents to about 40% of the reactor contents.

In a continuous process, the mean residence time of the catalyst and polymer in the reactor generally is from 5 minutes to 8 hours, and preferably from 10 minutes to 6 hours, more preferably from 10 minutes to 1 hour.

In some embodiments, ethylene is added to the reaction vessel in an amount to maintain a differential pressure in excess of the combined vapor pressure of the propylene and diene monomers. The ethylene content of the polymer is determined by the ratio of ethylene differential pressure to the total reactor pressure. Generally the polymerization process is carried out with a pressure of ethylene of from 10 to 1000 psi (70 to 7000 kPa), most preferably from 40 to 800 psi (30 to 600 kPa). The polymerization is generally conducted at a temperature of from 25 to 250° C., preferably from 75 to 200° C., and most preferably from greater than 95 to 200° C.

In another embodiment of the invention, a process for producing a propylene homopolymer or interpolymer of propylene with at least one additional olefinic monomer selected from ethylene or $C_{4-20}$ α-olefins comprises the following steps: 1) providing controlled addition of a nonmetallocene, metal-centered, heteroaryl ligand catalyst to a reactor, including a cocatalyst and optionally a scavenger component; 2) continuously feeding propylene and optionally one or more additional olefinic monomers independently selected from ethylene or $C_{4-20}$ α-olefins into the reactor, optionally with a solvent or diluent, and optionally with a controlled amount of $H_2$; and 3) recovering the polymer product. Preferably, the process is a continuous solution process. The cocatalysts and optional scavenger components in the novel process can be independently mixed with the catalyst component before introduction into the reactor, or they may each independently be fed into the reactor using separate streams, resulting in "in reactor" activation. Scavenger components are known in the art and include, but are not limited to, alkyl aluminum compounds, including alumoxanes. Examples of scavengers include, but are not limited to, trimethyl aluminum, triethyl aluminum, triisobutyl aluminum, trioctyl aluminum, methylalumoxane (MAO), and other alumoxanes including, but not limited to, MMAO-3A, MMAO-7, PMAO-IP (all available from Akzo Nobel).

As previously note, the process described above may optionally use more than one reactor. The use of a second reactor is especially useful in those embodiments in which an additional catalyst, especially a Ziegler-Natta or chrome catalyst, or a metallocene catalyst, especially a CGC, is employed. The second reactor typically holds the additional catalyst.

By proper selection of process conditions, including catalyst selection, polymers with tailored properties can be produced. For a solution polymerization process, especially a continuous solution polymerization, preferred ranges of ethylene concentration at steady state are from less than about 0.02 weight percent of the total reactor contents to about 5 weight percent of the total reactor contents, and the preferred range of polymer concentration is from about 10% of the reactor contents by weight to about 45% of the reactor contents or higher.

In general, catalyst efficiency (expressed in terms of gram of polymer produced per gram of transition metal) decreases with increasing temperature and decreasing ethylene concentration. In addition, the molecular weight of the polymer product generally decreases with increasing reactor temperature and decreases with decreasing propylene and ethylene concentration. The molecular weight of the polyolefin can also be controlled with the addition of chain transfer compounds, especially through the addition of $H_2$.

When two or more different catalysts are used in certain embodiments disclosed herein, each catalyst may make a different molecular weight product. A high molecular weight catalyst is defined relative to a low molecular weight catalyst. A high weight molecular weight catalyst refers to a catalyst which by itself produces a polymer with a high weight-average molecular weight $M_{wH}$ from the comonomers of choice under a set of given polymerization conditions, whereas a low molecular weight catalyst refers to a catalyst which by itself produces a polymer with a low weight average molecular weight $M_{wL}$ from the same comonomers under substantially the same polymerization conditions. Moreover, the ratio of the high molecular weight to the low molecular weight, i.e., $M_{wH}/M_{wL}$ is greater than about 1.3. Generally, the ratio, $M_{wH}/M_{wL}$, is in the range from about 1.5 to about 60, preferably in the range from about 1.5 to about 40, and more preferably from about 1.5 to about 10. In some embodiments, the ratio is from about 3.0 to about 6.0. In other embodiments, the ratio $M_{wH}/M_{wL}$ can be greater than 60 (e.g., 70, 80, 90, or even 100), but it is generally less preferred.

Due to the intrinsic molecular weight differences in the polymer produced by the chosen high and low molecular weight catalysts, the polymer produced by the two catalysts in a single reactor has a high molecular weight fraction and a low molecular weight fraction. Such a phenomenon is referred to herein after as "polymer split." A polymer molecular weight split is defined as the weight fraction of the high molecular weight polymer component or fraction in a polymer with such split. The relative fraction of the high molecular weight component can be measured by deconvoluting a gel permeation chromatography ("GPC") peak. One characteristic of the process described herein is that the polymer molecular weight split may be varied from 0 to 100% by adjusting the ratio of the high molecular weight catalyst to the low molecular weight catalyst. Because any two catalysts may exhibit different catalytic efficiency at a given set of polymerization process conditions, the polymer molecular weight split may not correspond directly to the molar ratio of the two catalysts.

A high molecular weight catalyst and a low molecular weight catalyst are determined with reference to each other. One does not know whether a catalyst is a high molecular weight catalyst or a low molecular weight catalyst until after another catalyst is also selected. Therefore, the terms "high molecular weight" and "low molecular weight" used herein when referring to a catalyst are merely relative terms and do not encompass any absolute value with respect to the molecular weight of a polymer. After a pair of catalysts are selected, one can easily ascertain which one is the high molecular catalyst by the following procedure: 1) select at least one monomer which can be polymerized by the chosen catalysts; 2) make a polymer from the selected monomer(s) in a single reactor containing one of the selected catalysts under pre-selected polymerization conditions; 3) make another polymer from the same monomer(s) in a single reactor containing the other catalyst under substantially the same polymerization conditions; and 4) measure the MFR for the respective interpolymers. The catalyst that yields a lower MFR is the higher molecular weight catalyst. Conversely, the catalyst that yields a high MFR is the lower molecular weight catalyst. Using this methodology, it is possible to rank a plurality of catalysts based on the molecular weight of the polymers they can produce under substantially the same conditions. As such, one may select three, four, five, six, or more catalysts according their molecular weight capability and use these catalysts simultaneously in a single polymerization reactor to produce polymers with tailored structures and properties.

The nature of the polymer product of the instant invention depends on the characteristics of each catalyst as well as the specifics of the process in which the catalysts are used. By careful choice of each catalyst, the polymer product can be tailored to achieve specific properties. For example, in order to obtain a polymer with a broader molecular weight distribution, two (or more) catalysts preferably should be chosen so that the difference in molecular weight at the conditions of polymerization ($M_{wH}/M_{wL}$) is large, preferably greater than 4.0, more preferably greater than 6.0, even more preferably greater than 8.0. For a narrower MWD product, the catalysts preferably should be chosen so that $M_{wH}/M_{wL}$ is relatively low, preferably 4.0 or less, more preferably 3.0 or less, still more preferably 2.5 or less.

In one embodiment of the invention, a process for producing a propylene homopolymer or interpolymer of propylene with at least one additional olefinic monomer selected from ethylene or $C_{4-20}$ α-olefins comprises the following steps: 1) providing controlled addition of a nonmetallocene, metal-centered, pyridyl-amine catalyst to a reactor, including a cocatalyst and optionally a scavenger component; 2) continuously feeding propylene and optionally one or more additional olefinic monomers independently selected from ethylene or $C_{4-20}$ α-olefins into the reactor, optionally with a solvent or diluent, and optionally with a controlled amount of $H_2$, 3) feeding a second catalyst to the same reactor, including a cocatalyst and optionally a scavenger; and 4) recovering the polymer product. Preferably, the process is a continuous solution process. The cocatalysts and optional scavenger components in the novel process can be independently mixed with each catalyst component before introduction into the reactor, or they may each independently be fed into the reactor using separate streams, resulting in "in reactor" activation. The novel process described above may optionally use more than one reactor, especially where a second reactor is used wherein the second reactor comprises an additional catalyst, especially a Ziegler-Natta or chrome catalyst, a metallocene catalyst, especially a CGC.

Applications

The polymers made in accordance with embodiments of the invention have many useful applications. For example, fabricated articles made from the polymers may be prepared using all of the conventional polyolefin processing techniques. Useful articles include films (e.g., cast, blown, calendaring and extrusion coated), including multi-layer films, greenhouse films, shrink films including clarity shrink film, lamination film, biaxially-oriented film, extrusion coating, liners, clarity liners, overwrap film, agricultural film; fibers (e.g., staple fibers) including use of an interpolymer disclosed herein as at least one component comprising at least a portion of the fiber's surface), spunbond fibers or melt blown fibers (using, e.g., systems as disclosed in U.S. Pat. Nos. 4,430,563, 4,663,220, 4,668,566 or 4,322,027), and gel spun fibers (e.g., the system disclosed in U.S. Pat. No. 4,413,110); both woven and nonwoven fabrics (e.g., spunlaced fabrics disclosed in U.S. Pat. No. 3,485,706) or structures made from such fibers (including, e.g., blends of these fibers with other fibers such as PET or cotton), foams, and thermoform and molded articles (e.g., made using an injection molding process, a blow molding process or a rotomolding process). Monolayer and multilayer films may be made according to the film structures and fabrication methods described in U.S. Pat. No. 5,685,128.

Figure 10:
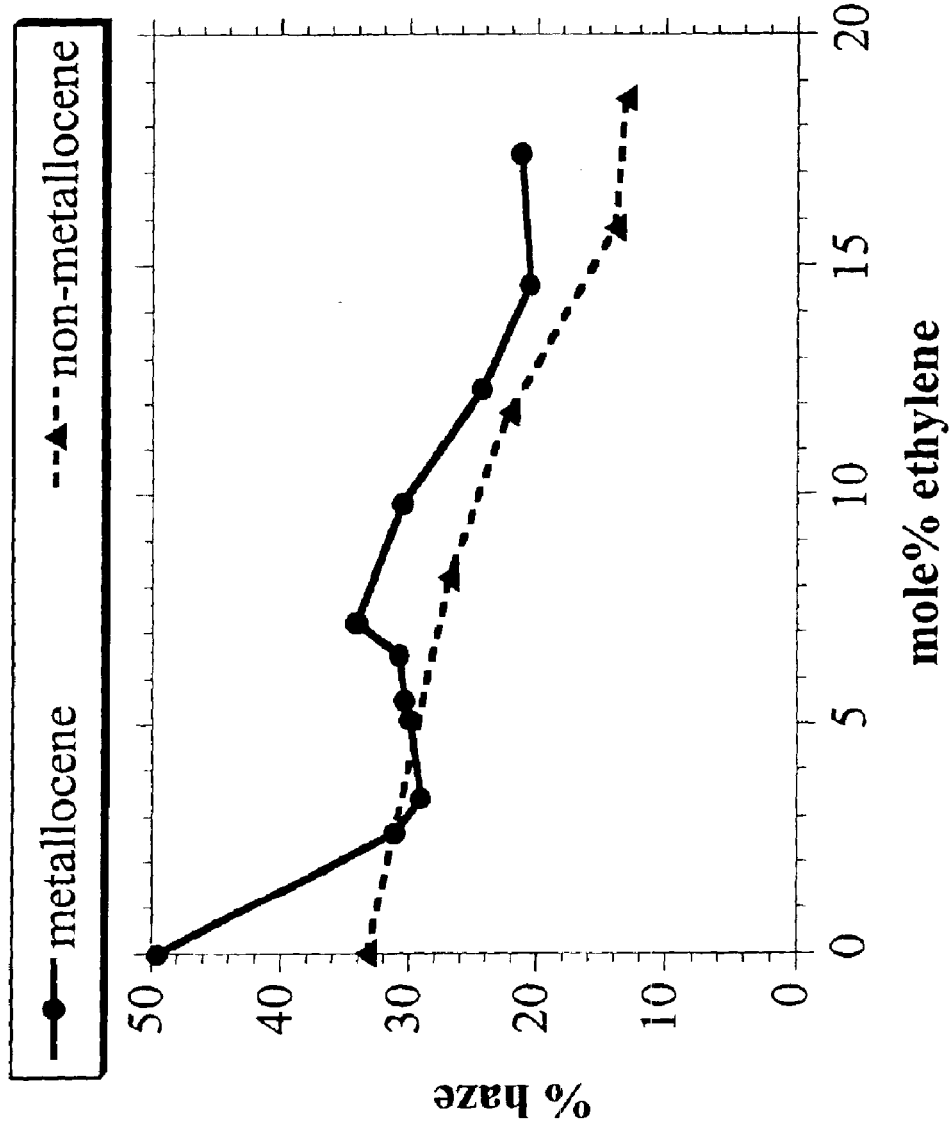
FIG. 10 shows a haze versus mole percent ethylene comparison of a conventional metallocene catalyzed P/E copolymer and a P/E* copolymer of this invention.
Figure 11:
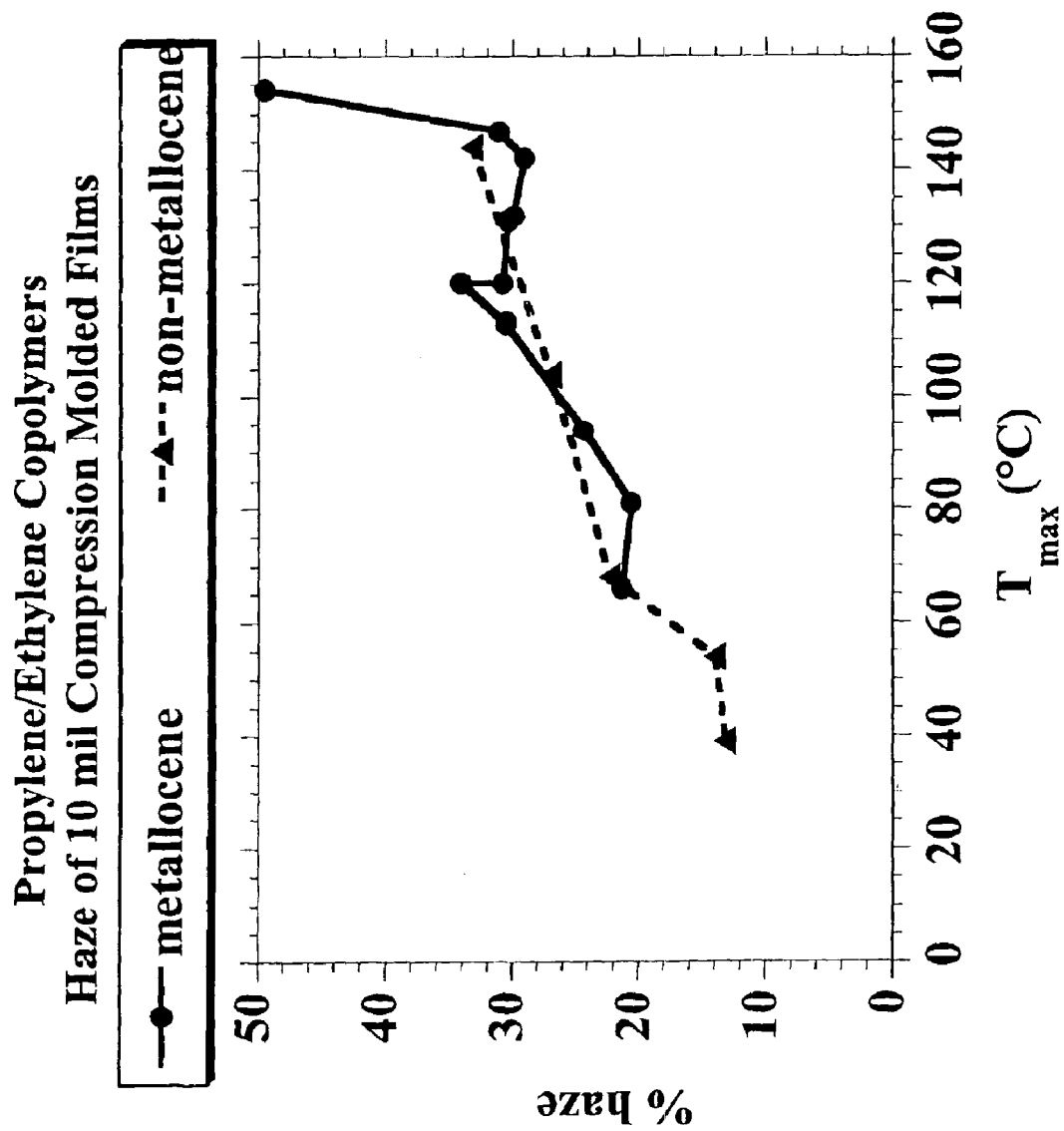
FIG. 11 shows a haze versus Tmax comparison of a conventional metallocene catalyzed P/E copolymer and a P/E* copolymer of this invention.
Figure 12:
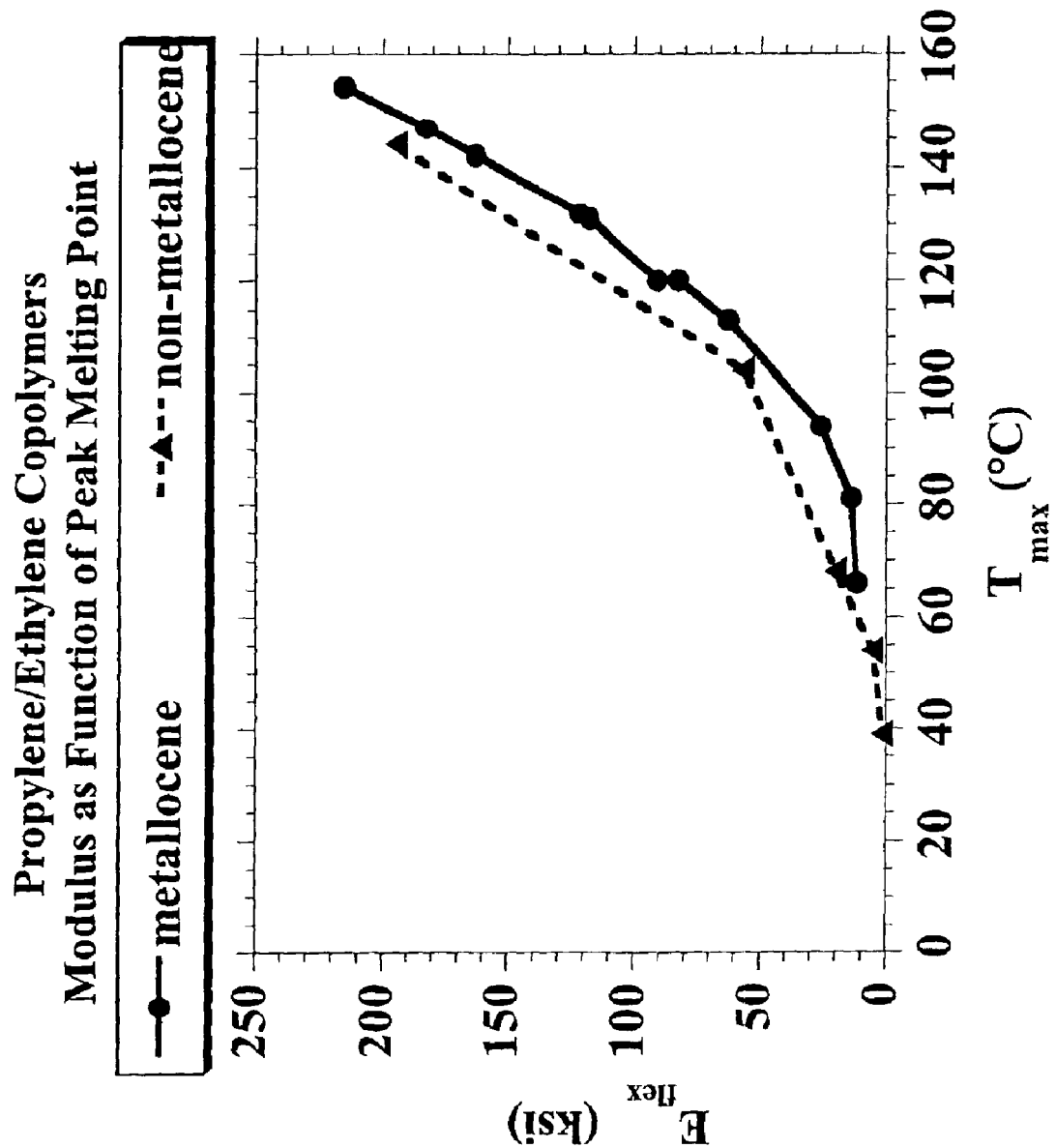
FIG. 12 shows an Eflex versus Tmax comparison of a conventional metallocene catalyzed P/E copolymer and a P/E* copolymer of this invention.
Figure 13:
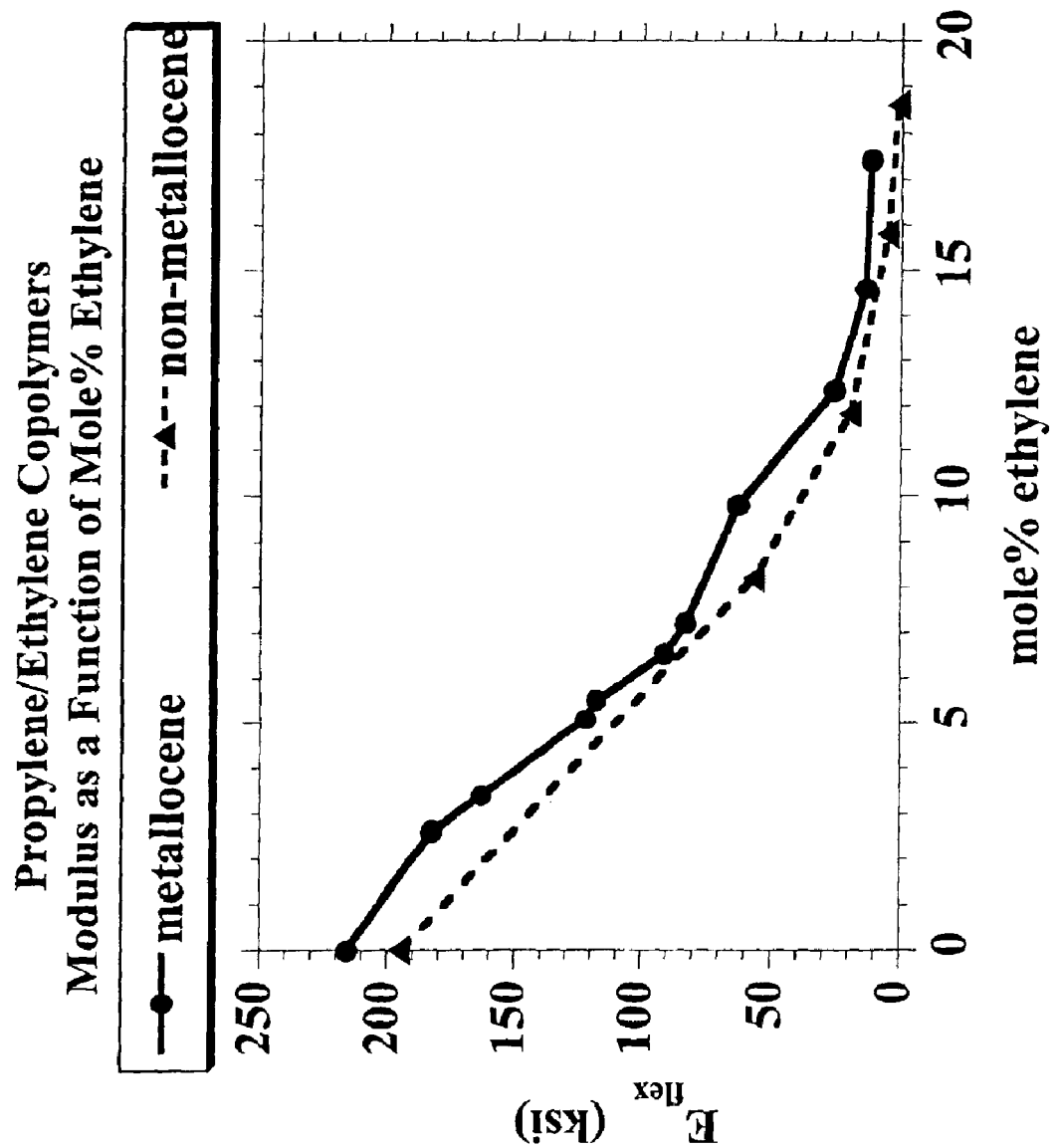
FIG. 13 shows an Eflex versus mole percent ethylene comparison of a conventional metallocene catalyzed P/E copolymer and a P/E* copolymer of this invention.

The inventive polymers exhibit excellent optics. FIG. 10 illustrates the improved haze values reported by compression molded films made from the inventive polymer versus a similar film made from a comparable metallocene catalyzed propylene polymer across various ethylene contents. Similar films also demonstrate comparable haze values measured across various Tmax (FIG. 11), and improved flexibility measured across both ethylene content and Tmax (FIGS. 12 and 13). The data behind these figures is reported in Example 21.

Figure 14:
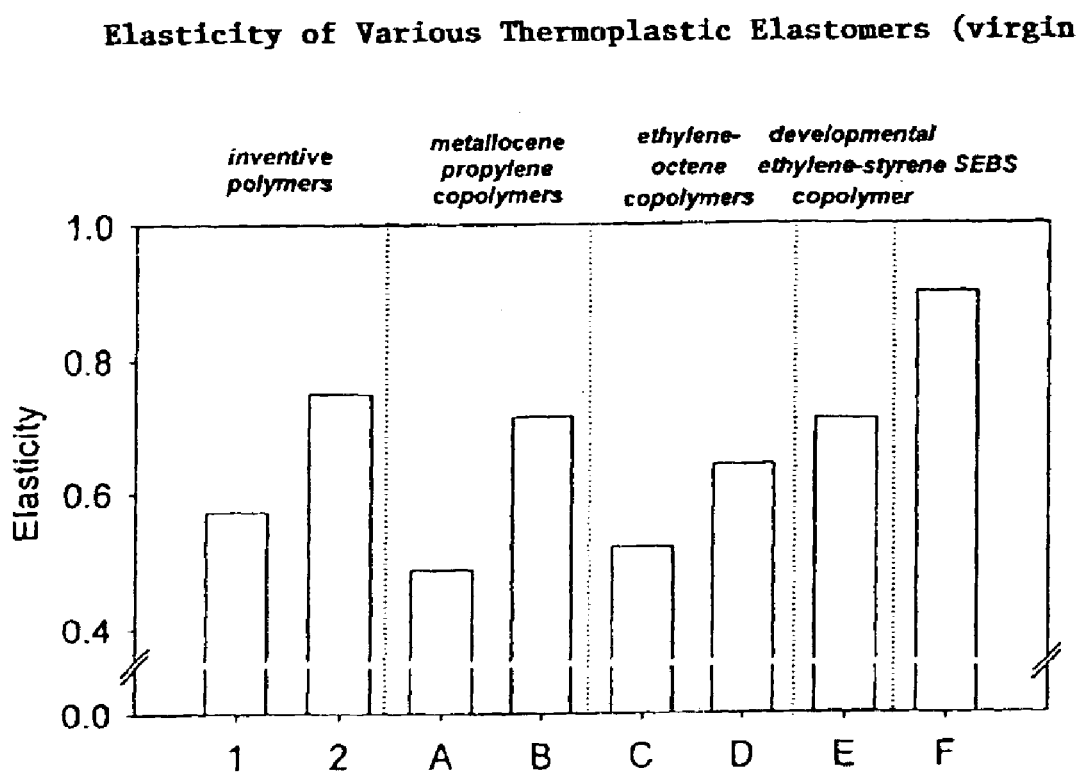
FIG. 14 is a bar graph comparing the elasticity of unstretched P/E* copolymers of this invention against various conventional unstretched thermoplastic elastomers.

The polymers of this invention also exhibit excellent elasticity. FIG. 14 reports the comparative results for elasticity of two copolymers of this invention at different ethylene contents versus a metallocene catalyzed propylene copolymer, a polyethylene elastomer, and ethylene-styrene elastomer and a hydgrogenated styrene-ethylene-butene-styrene block elastomer. Of even more interest, FIG. 15 reports the comparative results of these same elastomers after being stretched. The elasticity of the polymers of this invention not only increased markedly, but they now compared favorably even to the hydgrogenated styrene-ethylene-butene-styrene block elastomers. The data behind these figures is reported in Example 22. FIG. 32 reports an elasticity-modulus relationship for metallocene-catalyzed and nonmetallocene-catalyzed polymers. The data of these figures show that the nonmetallocene-catalyzed copolymers have higher modulus at the same elasicity, both pre- and post-stretched. This means that less material is needed of the nonmetallocene-catalyzed polymer than the metallocene-catalyzed polymer for the same elastic performance.

The elastomeric polymers of this invention can be used in a variety of different applications including fiber, film, sheeting and molded articles. Whether or not pre-stretching is desirable will depend upon the application. For example, the elastomeric polymers of this invention can replace the thermoplastic triblock elastomers as the filament layer in the stretch bonded laminate process of U.S. Pat. No. 6,323,389. The filament layer would be stretched, preferably only once, prior to being sandwiched between the two spunbond layers. In an alternative example, the elastomeric polymers of this invention can replace the elastic layer in the necked bonded laminate process of U.S. Pat. No. 5,910,224. Some pre-stretching of the propylene polymer may be preferred.

With respect to injection molding applications, the polymers of this invention exhibit a good balance between low haze values and toughness. For example, a comparison of samples 19-1-1 and 19-1-2 in Table 19-1 shows that at the same level of haze (e.g., a relatively low 11%) the inventive polymers exhibit an equivalent modulus and a better toughness than a comparable propylene-ethylene-octene polymer made with a metallocene catalyst. Moreover, at a similar level of haze the inventive polymers are almost an order of magnitude more flexible and much tougher than a comparable Ziegler-Natta catalyzed propylene-ethylene polymer. In comparison to ethylene-octene polymers, comparable inventive polymers display a higher flexural modulus and hardness at equivalent upper service temperatures, e.g., >70 C. These properties, in turn, mean that the inventive polymers are useful in various film and impact applications, e.g., packaging and facia.

With respect to blown film applications, the inventive polymers exhibit excellent optics, e.g., low haze and high gloss, and much better toughness (e.g., tear and dart) than traditional Ziegler-Natta catalyzed polypropylene at comparable ethylene contents. These are characteristics are shown in FIGS. 16–18. Moreover, blown films made from the inventive polymers exhibit excellent hot tack and heat seal properties (e.g., a broader temperature window for the former and a lower sealing temperature for the latter than comparable Ziegler-Natta catalyzed polypropylene, even when the latter has a higher ethylene content). FIGS. 19 and 20 illustrate these properties. The inventive polymers also exhibit superior toughness and haze and gloss at equivalent modulus than many traditional polyethylenes, e.g., linear low density polyethylene, and certain polyethylene blends, e.g., in-reactor blends of at least one metallocene catalyzed polyethylene and at least one Ziegler-Natta catalyzed polyethylene. The experimental details behind the data of these figures is reported in Example 20.

The polymers of this invention are also useful for wire and cable coating operations, wire and cable jacketing, including low, medium and high voltage cable jacketing, semi-conductive layers used in wire and cable power applications, wire and cable insulation, especially medium and high voltage cable insulation, telecommunications cable jackets, optical fiber jackets, as well as in sheet extrusion for vacuum forming operations. In addition, the novel polymers may be used in foams, including high strength foam, soft foam, rigid foam, cross-linked foam, high strength foam for cushioning applications, and sound insulation foam, blow molded bottles, frozen food packages; thermoforming, especially cups and plates, trays and containers; injection moulding; blow-moulding; pipe, including potable water pipe and high pressure pipe; and automotive parts. The skilled artisan will appreciate other uses for the novel polymers and compositions disclosed herein.

Useful compositions are also suitably prepared comprising the polymers according to embodiments of the invention and at least one other natural or synthetic polymer. Preferred other polymers include, but are not limited to, thermoplastics, such as styrene-butadiene block copolymers, polystyrene (including high impact polystyrene), ethylene vinyl alcohol copolymers, ethylene acrylic acid copolymers, other olefin copolymers (especially polyethylene copolymers) and homopolymers (e.g., those made using conventional heterogeneous catalysts). Examples include polymers made by the process of U.S. Pat. No. 4,076,698, other linear or substantially linear polymers as described in U.S. Pat. No. 5,272,236, and mixtures thereof. Other substantially linear polymers and conventional HDPE and/or LDPE may also be used in the thermoplastic compositions.

Melt Strength (measured in cN) and Melt Drawability (measured in mm/s) are measured by pulling strands of the molten polymers or blends at constant acceleration until breakage occurs. The experimental set-up consists of a capillary rheometer and a Rheotens apparatus as take-up device. The molten strand is drawn uniaxially to a set of accelerating nips located 100 mm below the die. The force required to uniaxially extend the strands is recorded as a function of the take-up velocity of the nip rolls. In the case of polymer melts exhibiting draw resonance (indicated by the onset of a periodic oscillation of increasing amplitude in the measured force profile), the maximum force and wheel velocity before the onset of draw resonance are taken as the melt strength and drawability, respectively. In the absence of draw resonance, the maximum force attained during test is defined as the melt strength and the velocity at which breakage occurs is defined as the melt drawability. These tests are run under the following conditions:

TABLE F

Melt Strength and Drawablility Test Conditions

Mass flow rate: 1.35 gram/min
Temperature: 190° C.
Equilibration Time at 190° C.: 10 minutes
Die: 20:1 with entrance angle of aproximately 45 degrees
Capillary length: 41.9 mm
Capillary diameter: 2.1 mm
Piston diameter: 9.54 mm
Piston velocity: 0.423 mm/s
Shear rate: 33.0 s$^{-1}$
Draw-down distance (die exit to take-up wheels): 100 mm
Cooling conditions: ambient air
Acceleration: 2.4 mm/s$^2$ For one aspect of the present invention, the novel polymers are useful to produce foams having improved properties. For foams, and other applications requiring melt strength, the MFR is preferably in the range of 0.1–10, more preferably 0.3–3, most preferably 0.5–2. The melt strength is preferably greater than 5 cN, more preferably >9 cN, most preferably >12 Cn. The drawability is preferably >15 mm/sec, more preferably >25 mm/sec, most preferably >35 mm/sec.

In one aspect of the present invention, the novel polymers disclosed in the present invention are useful for a wide range of applications where good optical properties are beneficial. Gloss is measured according to ASTM D-1746. Haze is measured according to ASTM D-1003, and Clarity is measured according to ASTM D-2457. In one aspect of the polymers disclosed herein, films having haze of less than 10% can be produced. In addition films having clarity of >91% are beneficially obtained.

The polymers of this invention, either alone or in combination with one or more other polymers (either polymers of the invention or polymers not of the invention) may be blended, if desired or necessary, with various additives such as antioxidants, ultraviolet absorbing agents, antistatic agents, nucleating agents, lubricants, flame retardants, antiblocking agents, colorants, inorganic or organic fillers or the like.

As noted above, the polymers of this invention are useful in the preparation of fibers and films. With respect to fibers, elastic fibers comprising polyolefins are known, e.g., U.S. Pat. Nos. 5,272,236, 5,278,272, 5,322,728, 5,380,810, 5,472,775, 5,645,542, 6,140,442 and 6,225,243. The polymers of this invention can be used in essentially the same manner as known polyolefins for the making and using of elastic fibers. In this regard, the polymers of this invention can include functional groups, such as a carbonyl, sulfide, silane radicals, etc., and can be crosslinked or uncrosslinked. If crosslinked, the polymers can be crosslinked in any known manner, e.g., peroxide, azo, electromagnetic radiation such as electron beam, UV, IR, visible light, and the like. The use of additives, promoters, etc., can be employed as desired.

The polypropylene polymers of this invention can be blended with other polymers to form, among other things, useful fibers. Suitable polymers for blending with the polypropylene polymers of this invention are commercially available from a variety of suppliers and include, but are not limited to, other polyolefins such as an ethylene polymer (e.g., low density polyethylene (LDPE), ULDPE, medium density polyethylene (MDPE), LLDPE, HDPE, homogeneously branched linear ethylene polymer, substantially linear ethylene polymer, graft-modified ethylene polymer ethylene-styrene interpolymers, ethylene vinyl acetate interpolymer, ethylene acrylic acid interpolymer, ethylene ethyl acetate interpolymer, ethylene methacrylic acid interpolymer, ethylene methacrylic acid ionomer, and the like), polycarbonate, polystyrene, conventional polypropylene (e.g., homopolymer polypropylene, polypropylene copolymer, random block polypropylene interpolymer and the like), thermoplastic polyurethane, polyamide, polylactic acid interpolymer, thermoplastic block polymer (e.g. styrene butadiene copolymer, styrene butadiene styrene triblock copolymer, styrene ethylene-butylene styrene triblock copolymer and the like), polyether block copolymer (e.g., PEBAX), copolyester polymer, polyester/polyether block polymers (e.g., HYTEL), ethylene carbon monoxide interpolymer (e.g., ethylene/carbon monoxide (ECO), copolymer, ethylene/acrylic acid/carbon monoxide (EAACO) terpolymer, ethylene/methacrylic acid/carbon monoxide (EMAACO) terpolymer, ethylene/vinyl acetate/carbon monoxide (EVACO) terpolymer and styrene/carbon monoxide (SCO)), polyethylene terephthalate (PET), chlorinated polyethylene, and the like and mixtures thereof. In other words, the polyolefin used in the practice of this invention can be a blend of two or more polyolefins, or a blend of one or more polyolefins with one or more polymers other than a polyolefin. If the polyolefin used in the practice of this invention is a blend of one or more polyolefins with one or more polymers other than a polyolefin, then the polyolefins comprise at least about 1, preferably at least about 50 and more preferably at least about 90, wt % of the total weight of the blend.

In one embodiment, one or more polypropylene polymers of this invention is blended with a conventional polypropylene polymer. Suitable conventional polypropylene polymers for use in the invention, including random propylene ethylene polymers, are available from a number of manufacturers, such as, for example, Montell Polyolefins and Exxon Chemical Company. Suitable conventional polypropylene polymers from Exxon are supplied under the designations ESCORENE and ACHIEVE.

Suitable graft-modified polymers for use in this invention are well known in the art, and include the various ethylene polymers bearing a maleic anhydride and/or another carbonyl-containing, ethylenically unsaturated organic radical. Representative graft-modified polymers are described in U.S. Pat. No. 5,883,188, such as a homogeneously branched ethylene polymer graft-modified with maleic anhydride.

Suitable polylactic acid (PLA) polymers for use in the invention are well known in the literature (e.g., see D. M. Bigg et al., "Effect of Copolymer Ratio on the Crystallinity and Properties of Polylactic Acid Copolymers", ANTEC '96, pp. 2028–2039; WO 90/01521; EP 0 515 203A and EP 0 748 846 A2. Suitable polylactic acid polymers are supplied commercially by Cargill Dow under the designation Eco-PLA.

Suitable thermoplastic polyurethane polymers for use in the invention are commercially available from The Dow Chemical Company under the designation PELLATHANE.

Suitable polyolefin carbon monoxide interpolymers can be manufactured using well known high pressure free-radical polymerization methods. However, they may also be manufactured with the use of so-called homogeneous catalyst systems such as those described and referenced above.

Suitable free-radical initiated high pressure carbonyl-containing ethylene polymers such as ethylene acrylic acid interpolymers can be manufactured by any technique known in the art including the methods taught by Thomson and Waples in U.S. Pat. Nos. 3,520,861, 4,988,781; 4,599,392 and 5,384,373.

Suitable ethylene vinyl acetate interpolymers for use in the invention are commercially available from various suppliers, including Exxon Chemical Company and Du Pont Chemical Company.

Suitable ethylene/alkyl acrylate interpolymers are commercially available from various suppliers. Suitable ethylene/acrylic acid interpolymers are commercially available from The Dow Chemical Company under the designation PRIMACOR. Suitable ethylene/methacrylic acid interpolymers are commercially available from Du Pont Chemical Company under the designation NUCREL.

Chlorinated polyethylene (CPE), especially chlorinated substantially linear ethylene polymers, can be prepared by chlorinating polyethylene in accordance with well known techniques. Preferably, chlorinated polyethylene comprises equal to or greater than 30 weight percent chlorine. Suitable chlorinated polyethylenes for use in the invention are commercially supplied by The Dow Chemical Company under the designation TYRIN.

The polypropylene polymer, if elastic, can also be shaped or fabricated into elastic films, coatings, sheets, strips, tapes, ribbons and the like. The elastic film, coating and sheet of the present invention may be fabricated by any method known in the art, including blown bubble processes (e.g., simple bubble as well as biaxial orientation techniques such as trapped bubble, double bubble and tenter framing), cast extrusion, injection molding processes, thermoforming processes, extrusion coating processes, profile extrusion, and sheet extrusion processes. Simple blown bubble film processes are described, for example, in The Encyclopedia of Chemical Technology, Kirk-Othmer, Third Edition, John Wiley & Sons, New York, 1981, Vol. 16, pp. 416–417 and Vol. 18, pp. 191–192. The cast extrusion method is described, for example, in Modem Plastics Mid-October 1989 Encyclopedia Issue, Volume 66, Number 11, pages 256 to 257. Injection molding, thermoforming, extrusion coating, profile extrusion, and sheet extrusion processes are described, for example, in Plastics Materials and Processes, Seymour S. Schwartz and Sidney H. Goodman, Van Nostrand Reinhold Company, New York, 1982, pp. 527–563, pp. 632–647, and pp. 596–602.

Not only can the polymers of this invention be blended with one or more other polymers, but they can also be blended with various additives such as nucleating, clarifying, stiffness and/or crystallization rate agents. These agents are used in a conventional matter and in conventional amounts.

The polymers of this invention can also be functionalized by adding one or more functional groups, e.g. through the use of a functionalized azide, to the polymer chain in a post-reaction operation. Optionally, the polymers of this invention can be subjected to post-reaction treatments, e.g. crosslinking, vis-breaking, and the like. Vis-breaking is particularly useful in reducing the viscosity of high molecular weight polymers. These post treatments are also used in their conventional manner.

Figure 21A:
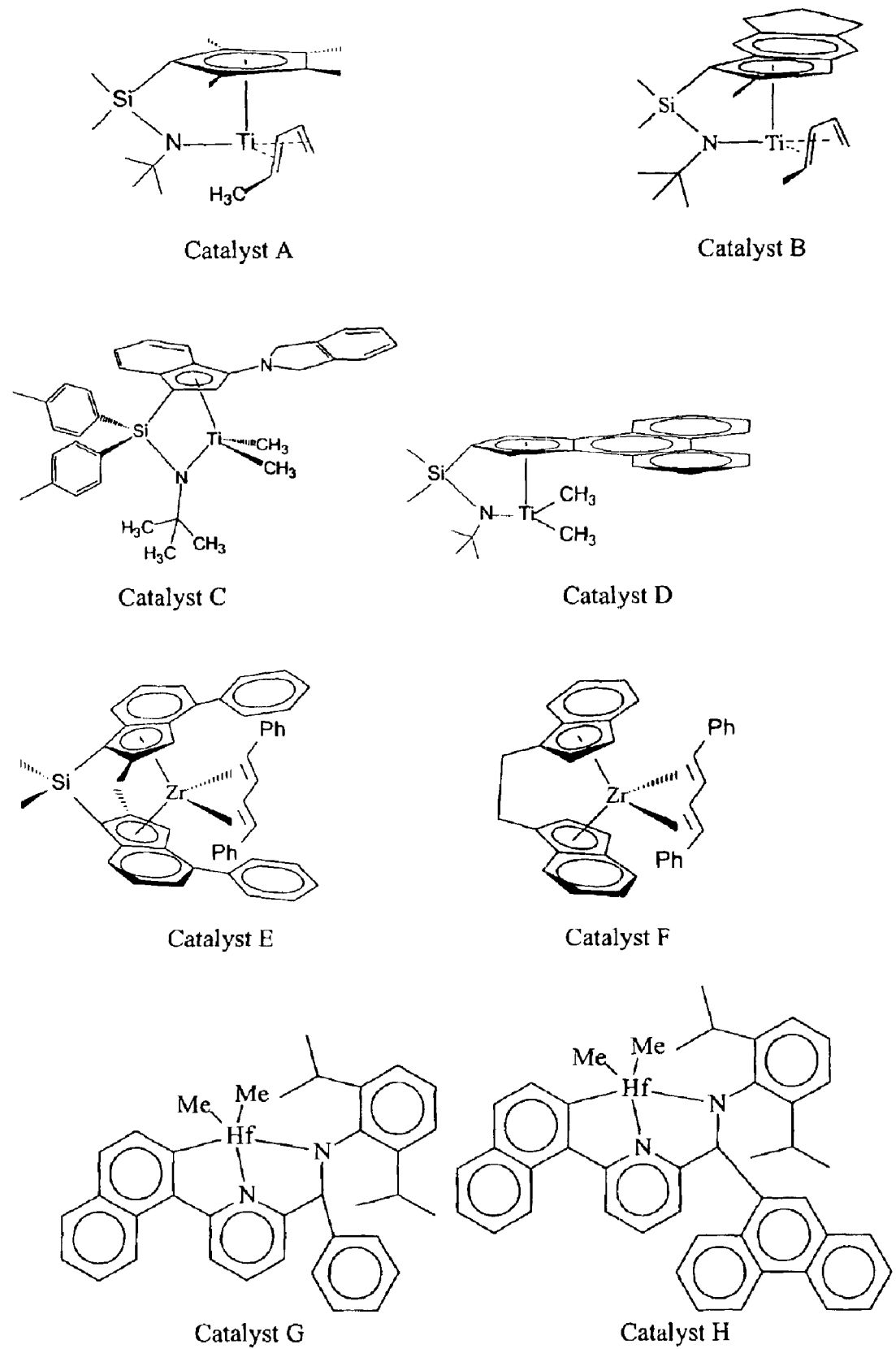

The following examples are given to illustrate various embodiments of the invention. They do not intend to limit the invention as otherwise described and claimed herein. All numerical values are approximate. When a numerical range is given, it should be understood that embodiments outside the range are still within the scope of the invention unless otherwise indicated. In the following examples, various polymers were characterized by a number of methods. Performance data of these polymers were also obtained. Most of the methods or tests were performed in accordance with an ASTM standard, if applicable, or known procedures. All parts and percentages are by weight unless otherwise indicated FIGS. 21A and 21B illustrate the chemical structures of various catalysts described in the following examples.

SPECIFIC EMBODIMENTS

Tetrahydrofuran (THF), diethyl ether, toluene, hexane, and ISOPAR E (obtainable from Exxon Chemicals) are used following purging with pure, dry nitrogen and passage through double columns charged with activated alumina and alumina supported mixed metal oxide catalyst (Q-5 catalyst, available from Engelhard Corp). All syntheses and handling of catalyst components are performed using rigorously dried and deoxygenated solvents under inert atmospheres of nitrogen or argon, using either glove box, high vacuum, or Schlenk techniques, unless otherwise noted. MMAO-3A, PMAO, and PMAO-IP can be purchased from Akzo-Nobel Corporation.

Synthesis of $(C_5Me_4SiMe_2N^tBu)Ti(\eta^4$-1,3-pentadiene) (Catalyst A)

Catalyst A can be synthesized according to Example 17 of U.S. Pat. No. 5,556,928.

Synthesis of dimethylsilyl(2-methyl-s-indacenyl)(t-butylamido) titanium 1,3-pentadiene (Catalyst B)

Catalyst B can be synthesized according to Example 23 of U.S. Pat. No. 5,965,756.

Synthesis of (N-(1,1-dimethylethyl)-1,1-di-p-tolyl-1-((1,2,3,3a,7a-η)-3-(1,3-dihydro-2H-isoindol-2-yl)-1H-inden-1-yl)silanaminato-(2-)-N-)dimethyltitanium (Catalyst C)

(1) Preparation of dichloro(N-(1,1-dimethylethyl)-1,1-di(p-tolyl)-1-((1,2,3,3a,7a-η)-3-(1,3-dihydro-2H-isoindol-2-yl)-1H-inden-1-yl)silanaminato-(2-)-N-)-titanium

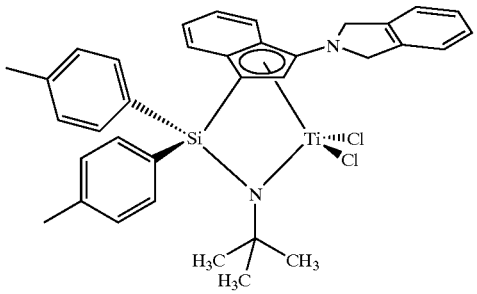

(A) Preparation of N-(tert-butyl)-N-(1,1-p-tolyl)-1-(3-(1,3-dihydro-2H-isoindol-2-yl)-1H-indenyl)silyl)amine:

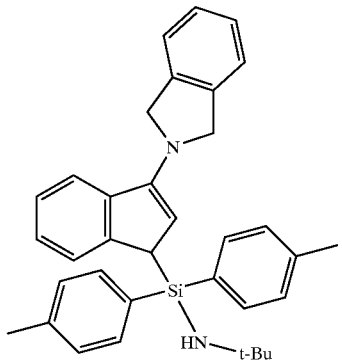

To a 1.70 g (5.35 mmol) of N-(tert-butyl)-N-(1-chloro-1,1-di(3-p-tolyl)silylamine dissolved in 20 mL of THF is added 1.279 g (5.35 mmol) of 1-(1H-3-indenyl)-1-(2,3-dihydro-1H-isoindolinyl) lithium salt dissolved in 20 mL of THF. After the addition, the reaction mixture is stirred for 9 hours and then solvent is removed under reduced pressure. The residue is extracted with 40 mL of hexane and filtered. Solvent is removed under reduced pressure giving 2.806 of product as a gray solid.

$^1$H (C$_6$D$_6$) δ: 1.10 (s, 9H), 2.01 (s, 3H), 2.08 (s, 3H), 4.12 (d, 1H, $^3J_{H-H}$=1.5 Hz), 4.39 (d, 1H, $^2J_{H-H}$=11.1 Hz), 4.57 (d, 1H, $^2J_{H-H}$=11.7 Hz), 5.55 (d, 1H, $^3J_{H-H}$=2.1 Hz), 6.9–7.22 (m, 10H), 7.56 (d, 1H, $^3J_{H-H}$=7.8 Hz), 7.62 (d, 1H, $^3J_{H-H}$=6.9 Hz), 7.67 (d, 1H, $^3J_{H-H}$=7.8 Hz), 7.83 (d, 1H, $^3J_{H-H}$=7.8 Hz). $^{13}$C{$^1$H} (C$_6$D$_6$) δ: 21.37, 21.43, 33.78, 41.09, 50.05, 56.56, 104.28, 120.98, 122.46, 123.84, 124.71, 124.84, 126.98, 128.29, 128.52, 129.05, 132.99, 133.68, 135.08, 135.90, 136.01, 138.89, 139.05, 139.09, 141.27, 146.39, 148.48.

(B) Preparation of N-(tert-butyl)-N-(1,1-p-tolyl)-1-(1,3-dihydro-2H-isoindol-2-yl)-1H-indenyl)silyl)amine, dilithium salt:

To a 50 mL hexane solution containing 2.726 g (5.61 mmol) of the N-(tert-butyl)-N-(1,1-p-tolyl)-1-(3-(1,3-dihydro-2H-isoindol-2-yl)-1H-indenyl)silyl)amine is added 7.4 mL of 1.6 M n-BuLi solution. During addition of the n-BuLi, a yellow precipitate appears. After stirring for 6 hours, the yellow precipitate is collected on a frit, washed with 2×25 mL of hexane, and dried under reduced pressure to give 2.262 g of the product as a yellow powder.

$^1$H(C$_6$D$_6$) δ: 1.17 (s, 9H), 2.30 (s, 6H), 4.51 (s, 4H), 6.21 (s, 1H), 6.47 (m, 2H), 6.97 (d, 4H, $^3J_{H-H}$=8.1 Hz), 7.15 (m, 2H), 7.23 (m, 2H), 7.50 (m, 1H), 7.81 (d, 4H, $^3J_{H-H}$=7.8 Hz), 8.07 (d, 1H, $^3J_{H-H}$=7.2 Hz). $^{13}$C{$^1$H} (C$_6$D$_6$) δ: 21.65, 38.83, 52.46, 59.82, 95.33, 112.93, 114.15, 115.78, 118.29, 122.05, 122.60, 124.16, 124.78, 126.94, 127.30, 133.06, 134.75, 137.30, 141.98, 148.17.

(C) Preparation of dichloro(N-(1,1-dimethylethyl)-1,1-di-p-tolyl-1-((1,2,3,3a,7a-η)-3-(1,3-dihydro-2H-isoindol-2-yl)-1H-inden-1-yl)silanaminato-(2-)-N-)titanium:

In the drybox 1.552 g (4.19 mmol) of TiCl$_3$(THF)$_3$ is suspended in 20 mL of THF. To this solution, 2.206 g (4.19 mmol) of N-(tert-butyl)-N-(1,1-p-tolyl)-1-(1,3-dihydro-2H-isoindol-2-yl)-1H-indenyl)silyl)amine, dilithium salt dissolved in 30 mL of THF is added within 1 minute. The solution is then stirred for 60 minutes. After this time, 0.76 g of PbCl$_2$ (2.75 mmol) is added and the solution is stirred for 60 minutes. The THF is then removed under reduced pressure. The residue is first extracted with 60 mL of methylene chloride and filtered. Solvent is removed under reduced pressure leaving a black crystalline solid. Hexane is added (30 mL) and the black suspension is stirred for 10 hour. The solids are collected on a frit, washed with 30 mL of hexane and dried under reduced pressure to give 2.23 g of the desired product as a deep purple solid.

$^1$H (THF-d$_8$) δ: 1.40 (s, 9H), 2.46 (s, 3H), 2.48 (s, 3H), 5.07 (d, 2H, $^2J_{H-H}$=12.3 Hz), 5.45 (d, 2H, $^2J_{H-H}$=12.6 Hz), 5.93 (s, 1H), 6.95 (d, 1H, $^3J_{H-H}$=9.0 Hz), 7.08 (d, 1H, $^3J_{H-H}$=7.8 Hz), 7.15–7.4 (m, 9H), 7.76 (d, 1H, $^3J_{H-H}$=7.8 Hz), 7.82 (d, 1H, $^3J_{H-H}$=7.5 Hz), 8.05 (d, 1H, $^3J_{H-H}$=8.7 Hz). $^{13}$C{$^1$H} (THF-d$_8$) δ: 21.71, 21.76, 33.38, 56.87, 61.41, 94.5, 107.95, 122.86, 125.77, 126.68, 127.84, 127.92, 128.40, 128.49, 129.36, 129.79, 131.23, 131.29, 135.79, 136.43, 136.73, 141.02, 141.22, 150.14.

(2) Preparation of (N-(1,1-dimethylethyl)-1,1-di-p-tolyl-1-((1,2,3,3a,7a-η)-3-(1,3-dihydro-2H-isoindol-2-yl)-1H-inden-1-yl)silanaminato-(2-)-N-)dimethyltitanium:

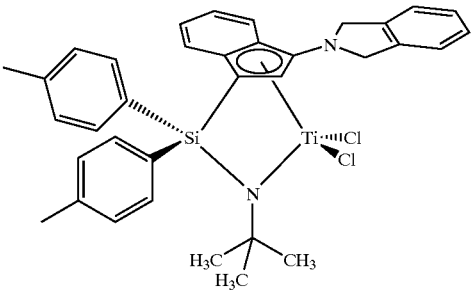

In the drybox 0.50 g of dichloro(N-(1,1-dimethylethyl)-1,1-di-p-tolyl-1-((1,2,3,3a,7a-η)-3-(1,3-dihydro-2H-isoindol-2-yl)-1H-inden-1-yl)silanaminato-(2-)-N-)titanium complex (0.79 mmol) is dissolved in 30 mL of diethyl ether. To this solution, 1.14 mL (1.6 mmol) of MeLi (1.6 M in ether) is added dropwise while stirring over a 1 minute period. After the addition of MeLi is completed, the solution is stirred for 1.5 hour. Diethyl ether is removed under reduced pressure and the residue extracted with 45 mL of hexane. Hexane is removed under reduced pressure giving a red crystalline material. This solid is dissolved in about 7 mL of toluene and 25 mL of hexane, filtered, and the solution was put into the freezer (−27° C.) for 2 days. The solvent is then decanted and the resulting crystals are washed with cold hexane and dried under reduced pressure to give 156 mg of product.

$^1$H (C$_6$D$_6$) δ: 0.25 (s, 3H), 0.99 (3H), 1.72 (s, 9H), 2.12 (s, 3H), 2.15 (s, 3H), 4.53 (d, 2H, $^2J_{H-H}$=11.7 Hz), 4.83 (d,

2H, $^2J_{H-H}$=11.7 Hz), 5.68 (s, 1H), 6.72 (dd, 1H, $^3J_{H-H}$=8.6 Hz, $^3J_{H-H}$=6.6 Hz), 6.9–7.2 (m, 11H), 7.30 (d, 1H, $^3J_{H-H}$=8.6 Hz).7.71 (d, 1H, $^3J_{H-H}$=8.5 Hz), 7.93 (d, 1H, $^3J_{H-H}$=7.8 Hz), 8.11 (d, 1H, $^3J_{H-H}$=7.8 Hz). $^{13}$C{$^1$H} (C$_6$D$_6$) δ: 21.45, 21.52, 35.30, 50.83, 56.03, 56.66, 57.65, 83.80, 105.64, 122.69, 124.51, 124.56, 125.06, 125.35, 127.33, 128.98, 129.06, 129.22, 133.51, 134.02, 134.62, 136.49, 136.84, 137.69, 139.72, 139.87, 143.84.

Synthesis of (1H-cyclopenta [1] phenanthrene-2-yl) dimethyl(t-butylamido)silane titanium dimethyl (Catalyst D)

Catalyst D can be synthesized according to Example 2 of U.S. Pat. No. 6,150,297.

Synthesis of rac-[dimethylsilylbis(1-(2-methyl-4-phenyl)indenyl)]zirconium (1,4-diphenyl-1,3-butadiene) (Catalyst E)

Catalyst E can be synthesized according to Example 15 of U.S. Pat. No. 5,616,664.

Synthesis of rac-[1,2-ethanediylbis(1-indenyl)]zirconium (1,4-diphenyl-1,3-butadiene) (Catalyst F)

Catalyst F can be synthesized according to Example 11 of U.S. Pat. No. 5,616,664.

Synthesis of Catalyst G

Hafnium tetrakisdimethylamine. The reaction is prepared inside of a dry box. A 500 mL round bottom flask containing a stir bar, is charged with 200 mL of toluene and LiNMe$_2$ (21 g, 95%, 0.39 mol). HfCl$_4$ (29.9 g, 0.093 mol) is added slowly over 2 h. The temperature reaches 55° C. The mixture is stirred overnight at ambient temperature. The LiCl is filtered off. The toluene is carefully distilled away from the product. Final purification is achieved by distillation with a vacuum transfer line attached to a cold (−78° C.) receiving flask. This process is performed outside the dry box on a Schlenk line. The material is distilled over at 110–120° C. at 300–600 microns. The 19.2 g of the white solid is collected.

2-formyl-6-naphthylpyridine. Inside of a dry box, naphthylboronic acid (9.12 g, 53.0 mmol) and Na$_2$CO$_3$ (11.64 g, 110 mmol) are dissolved in 290 mL of degassed 4:1 H$_2$O/MeOH. This solution is added to a solution of 8 g (43 mmol) of 2-bromo-6-formylpyridine and 810 mg (0.7 mmol) of Pd(PPh$_3$)$_4$ in 290 mL of degassed toluene. The charged reactor is removed from the dry box, while under a blanket of N$_2$ and is connected to the house N$_2$ line. The biphasic solution is vigorously stirred and heated to 70° C. for 4 h. On cooling to RT, the organic phase is separated. The aqueous layer is washed with 3×75 mL of Et$_2$O. The combined organic extracts are washed with 3×100 mL of H$_2$O and 1×100 mL of brine and dried over Na$_2$SO$_4$. After removing the volatiles in vacuo, the resultant light yellow oil is purified via trituration with hexanes. The isolated material is recrystallized from a hot hexane solution and ultimately yielded 8.75 g, 87% yield. mp 65–66° C.

$^1$H NMR (CDCl$_3$) δ 7.2–8.3 (m, 10H), 10.25 (s, 1 H) ppm. $^{13}$C NMR (CDCl$_3$) 120.3, 125.64, 125.8, 126.6, 127.26, 128.23, 129.00, 129.74, 130.00, 131.39, 134.42, 137.67, 137.97, 153.07, 160.33, 194.23 ppm.

6-naphthylpyridine-2-(2,6-diisopropylphenyl)imine: A dry, 500 mL 3-neck round bottom flask is charged with a solution of 5.57 g (23.9 mmol) of 2-formyl-6-naphthlypyridine and 4.81 g (27.1 mmol) of 2,6-diisopropylaniline in 238 mL of anhydrous THF containing 3 Å molecular sieves (6 g) and 80 mg of p-TsOH. The loading of the reactor is performed under N$_2$. The reactor is equipped with a condenser, an over head mechanical stirrer and a thermocouple well. The mixture is heated to reflux under N$_2$ for 12 h. After filtration and removal of the volatile in vacuo, the crude, brown oil is triturated with hexanes. The product is filtered off and rinsed with cold hexanes. The slightly off white solid weighes 6.42 g. No further purification is performed. mp 142–144° C.

$^1$H NMR (CDCl$_3$) δ 1.3 (d, 12 H), 3.14 (m, 2H), 7.26 (m, 3H), 7.5–7.6 (m, 5H), 7.75–7.8 (m, 3H), 8.02 (m 1H), 8.48 (m, 2H) ppm. $^{13}$C NMR (CDCl$_3$) 23.96, 28.5, 119.93, 123.50, 124.93, 125.88, 125.94, 126.49, 127.04, 127.24, 128.18, 128.94, 129.7, 131.58, 134.5, 137.56, 137.63, 138.34, 148.93, 154.83, 159.66, 163.86 ppm.

(6-naphthyl-2-pyridyl)-N-(2,6-diisopropylphenyl) benzylamine: A 250 mL 3-neck flask, equipped with mechanical stirrer and a N$_2$ sparge, is charged with 6-naphthylpyridine-2-(2,6-diisopropylphenyl)imine (6.19 mg, 15.8 mmol) and 80 mL of anhydrous, degassed Et$_2$O. The solution is cooled to −78 C. while a solution of phenyllithium (13.15 mL of 1.8 M in cyclohexane, 23.7 mmol) is added dropwise over 10 min. After warming to RT over 1 h. the solution is stirred at RT for 12 hours. The reaction is then quenched with ~50 mL of aq. NH$_4$Cl. The organic layer is separated, washed with brine and H$_2$O, then dried over Na$_2$SO$_4$. Using the Biotage Chromatography system (column # FK0-1107-19073, 5% THF/95% hexanes), the product is isolated as a colorless oil. The chromatography is performed by dissolving the crude oil in 50 mL of hexanes. The purification is performed in 2×~25 mL batches, using half of the hexane stock solution for each run. 7.0 g of the oil is isolated (93% yield).

$^1$H NMR (CDCl$_3$) δ 0.90 (d, 12 H), 3.0 (m, 2H), 4.86 (s, 1H), 5.16 (s, 1H), 7.00 (m, 3H), 7.1–7.6 (m, 12H), 7.8–7.88 (m, 2H), 7.91–7.99 (d, 1H) ppm. $^{13}$C NMR (CDCl$_3$) 24.58, 28.30, 70.02, 121.14, 123.62, 123.76, 123.95, 125.71, 126.32, 126.55, 126.74, 127.45, 128.04, 128.74, 129.47, 131.66, 134.49, 137.4, 138.95, 142.68, 143.02, 143.89, 159.36, 162.22 ppm.

Catalyst G-(Nme$_2$)$_3$: The reaction is performed inside of a dry box. A 100 mL round bottom flask is charged with Hf(Nme$_2$)$_4$ (2.5 g, 5.33 mmol), 30 mL of pentane and a stir bar. The amine 1 is dissolve in 40 mL of pentane then added to the stirring solution of Hf(Nme$_2$)$_4$. The mixture is stirred at ambient temperature for 16 h (overnight). The light yellow solid is filtered off and rinsed with cold pentane. The dry weight of the powder is 2.45 g. A second crop is collected from the filtrate weighing 0.63 g. The overall yield is 74%.

$^1$H NMR (C$_6$D$_6$) δ 0.39 (d, 3 H, J=6.77 Hz), 1.36 (d, 3H, J=6.9 Hz), 1.65 (d, 3H, J=6.68 Hz), 1.76 (d, 3H, J=6.78 Hz), 2.34 (br s, 6H), 2.80 (br s, 6H), 2.95 (br s, 6H), 3.42 (m, 1H, J=6.8 Hz), 3.78 (m, 1H, J=6.78 Hz), 6.06 (s, 1H), 6.78 (m, 2H), 6.94 (m, 1H), 7.1–7.4 (m, 13H), 7.8 (m, 2H) ppm.

Catalyst G: The reaction is performed inside of a dry box. A 100 mL round bottom flask is charged with 70 mL of pentane and 15 mL of a 2.0 M trimethyl aluminum in hexane solution. The solution is cooled to −40° C. The hafnium trisamide compound from the previous reaction (1.07, g 1.28 mmol) is added in small portions over 5–10 minutes. Upon the addition, a white gelatinous residue forms. After 45–60 min the reaction becomes yellow with a fine, yellow, powder precipitating from the mixture. After a total reaction time of 2.5 h the mixture is filtered and 615 mg of Catalyst G is isolated as a bright, yellow powder. No further purification is performed.

$^1$H NMR (C$_6$D$_6$) δ 0.51 (d, 3 H, J=6.73 Hz), 0.79 (s, 3H), 1.07 (s, 3H), 1.28 (d, 3H, J=6.73 Hz), 1.53(m, 6H), 3.37 (m, 1H, J=6.75 Hz), 3.96 (m, 1H, J=6.73 Hz), 6.05 (s, 1H), 6.50 (d, 1H, J=7.75 Hz), 6.92 (t, 1H, J=7.93 Hz), 7.1–7.59 (m, 12H), 7.6 (d, 1H), 7.8–8.0 (m, 2H), 8.3 (m, 1H), 8.69 (d, 1H, J=7.65 Hz) ppm.

Synthesis of Catalyst H

To a solution of 9-bromophenanthrene (10.36 mg, 41 mmol) in 132 mL of anhydrous, degassed $Et_2O$ cooled to −40 C. is added under $N_2$ 27 mL (43.2 mmol) of a 1.6 M solution of n-BuLi in hexanes. The solution is swirled to mix and allowed to react at −40 C. for 3 hours during which colorless crystals precipitated from solution. The 9-phenanthrenyllithium is added as a slurry to a well-mixed solution of 6-naphthylpyridine-2-(2,6-diisopropylphenyl) imine (10.6 g, 27.04 mmol) in 130 mL of $Et_2O$ cooled to −40 C. After warming to ambient temperature over 1 h, the solution is stirred at ambient temperature for 2 hours. The reaction is then quenched with aq. $NH_4Cl$, and subjected to an aqueous/organic work-up. The organic washes are combined and dried over $Na_2SO_4$. Upon removal of the volatiles with rotary evaporation, the product precipitates from solution. The isolated solids are rinsed with cold hexanes. The material is vacuum dried at 70° C. using the house vacuum over night. The dried material is isolated as a white solid, weighing 12.3 g for a yield of 80%. A second crop is isolated weighing 0.37 g. Mp 166–168° C.

$^1$H NMR ($C_6D_6$) δ 1.08 (dd, 12 H), 3.43 (m, 2H), 5.47 (m, 1H), 6.16 (d, 1H), 7.0–7.8 (m, 14H), 8.2 (d, 1H), 8.5–8.6 (m, 4H), ppm. $^{13}$C NMR ($CDCl_3$) 24.68, 28.22, 68.87, 120.56, 122.89, 123.63, 123.73, 124.07, 124.1, 125.5, 125.59, 126.24, 126.42, 126.52, 126.76, 126.83, 126.9, 127.05, 127.14, 128.0, 128.55, 129.49, 129.55, 130.67, 130.71, 131.52, 131.55, 132.24, 134.39, 137.57, 143.31, 159.1, 162 ppm.

Catalyst H-$(Nme_2)_3$: Inside of a dry box, six different teflon-screw capped, glass pressure tube reactors are each charged with $Hf(Nme_2)_4$ (1.55 g, 4.37 mmol, overall 9.3 g, 26.2 mmol), 10 mL of toluene and the ligand isolated from the previous procedure above (2.1 g, 3.68 mmol, overall 12.6 g, 22.1 mmol). The tightly sealed reactors are removed from the dry box and placed in a heater block with the temperature set at 125° C. The reactor tubes are heated overnight (~16 h). The cooled tubes are taken into the dry box and the contents of the reactor tubes are combined in a 500 mL round bottom flask. The flask is placed under vacuum to remove the dimethylamine and toluene. The light yellow/green solid which is left is rinsed with ~125 mL of cold pentane and filtered, yielding 13.6 g of a light yellow powder for a yield of 65%.

Catalyst H: The reaction is performed inside of a dry box. A 500 mL jar is charged with 250 mL of pentane and the hafnium amide isolated in the procedure outlined immediately above (13.6 g, 15.5 mmol). The mixture is cooled to −40° C. To the stirring mixture is slowly added 70 mL of a 2.0 M trimethyl aluminum (140 mmol) in hexane solution. After 3 h the reaction becomes yellow with a fine, powder precipitating from the mixture. The mixture is then cooled to −40° C. and filtered. The initially collected product is rinsed with 2×60 mL of cold pentane. 10.24 g Catalyst H is isolated (84% yield) with a purity of >99% by $^1$H NMR.

Synthesis of Armeenium Borate [methylbis (hydrogenatedtallowalkyl)ammonium tetrakis (pentafluoro phenyl) borate]

Armeenium borate can be prepared from ARMEEN® M2HT (available from Akzo-Nobel), HCl, and Li $[B(C_6F_5)_4]$ according to Example 2 of U.S. Pat. No. 5,919, 983.

General 1 Gallon Continuous Solution Propylene/ Ethylene Copolymerization Procedure Purified toluene solvent, ethylene, hydrogen, and propylene are supplied to a 1 gallon reactor equipped with a jacket for temperature control and an internal thermocouple. The solvent feed to the reactor is measured by a mass-flow controller. A variable speed diaphragm pump controls the solvent flow rate and increases the solvent pressure to the reactor. The propylene feed is measured by a mass flow meter and the flow is controlled by a variable speed diaphragm pump. At the discharge of the pump, a side stream is taken to provide flush flows for the catalyst injection line and the reactor agitator. The remaining solvent is combined with ethylene and hydrogen and delivered to the reactor. The ethylene stream is measured with a mass flow meter and controlled with a Research Control valve. A mass flow controller is used to deliver hydrogen into the ethylene stream at the outlet of the ethylene control valve. The temperature of the solvent/monomer is controlled by use of a heat exchanger before entering the reactor. This stream enters the bottom of the reactor. The catalyst component solutions are metered using pumps and mass flow meters, and are combined with the catalyst flush solvent. This stream enters the bottom of the reactor, but in a different port than the monomer stream. The reactor is run liquid-full at 500 psig with vigorous stirring. The process flow is in from the bottom and out of the top. All exit lines from the reactor are steam traced and insulated. Polymerization is stopped with the addition of a small amount of water, and other additives and stabilizers can be added at this point. The stream flows through a static mixer and a heat exchanger in order to heat the solvent/polymer mixture. The solvent and unreacted monomers are removed at reduced pressure, and the product is recovered by extrusion using a devolatilizing extruder. The extruded strand is cooled under water and chopped into pellets. The operation of the reactor is controlled with a process control computer.

EXAMPLE 1

Propylene/Ethylene Polymerization Using Metallocene Catalyst E (Comparative)

The general procedure for the 1 gallon continuous solution polymerization outlined above was employed. A catalyst solution containing 2.6 ppm Zr from Catalyst E was prepared and added to a 4 L catalyst storage tank. This solution was combined in a continuous stream with a continuous stream of a solution containing Armeenium tetrakis(pentafluorophenyl)borate in toluene and a continuous stream of a solution of PMAO-IP in toluene to give a ratio of total Ti:B:Al of 1:1.2:30. The activated catalyst solution was fed continuously into the reactor at a rate sufficient to maintain the reactor temperature at approximately 80° C. and a polymer production rate of approximately 3 pounds an hour. The polymer solution was continuously removed from the reactor exit and was contacted with a solution containing 100 ppm of water for each part of the polymer solution, and polymer stabilizers (i.e., 1000 ppm Irgaphos 168 and 1000 ppm Irganox 1010 per part of the polymer). The resulting exit stream was mixed, heated in a heat exchanger, and the mixture was introduced into a separator where the molten polymer was separated from the solvent and unreacted monomers. The resulting molten polymer was extruded and chopped into pellets after being cooled in a water bath. For this example, the propylene to ethylene ratio was 22.0. Product samples were collected over 1 hour time periods, after which time the melt flow rate was determined for each sample. FIG. 9 is a $^{13}$C NMR of Comparative Example 1, and it demonstrates the absence of regio-error peaks in the region around 15 ppm.

EXAMPLES 2–6

Examples 2–6 were conducted similar to Example 1 except as otherwise noted in Tables 2-6-1 and 2-6-2 below.

Catalyst E is listed for comparative purposes. FIG. 8 is the $^{13}C$ NMR sprectrum of the propylene/ethylene copolymer product of Example 2. FIGS. 2A and 2B show a comparison of the DSC heating traces of the propylene/ethylene copolymers of Comparative Example 1 and Example 2.

TABLE 2-6-1

Polymerization Conditions

| Example | Reactor TEMP DEG C. | SOLV FLOW LB/HR | C2 FLOW LB/HR | C3 FLOW LB/HR | H2 FLOW SCCM | POLY LBS/HR production rate |
|---|---|---|---|---|---|---|
| 1 (comparative) | 80.5 | 36.0 | 0.50 | 11.00 | 0 | 3.13 |
| 2 | 80.5 | 33.0 | 0.20 | 6.00 | 20.8 | 3.47 |
| 3 | 80.1 | 26.0 | 0.10 | 6.00 | 14.1 | 3.09 |
| 4 | 79.9 | 26.0 | 0.20 | 6.00 | 20.1 | 3.25 |
| 5 | 80.0 | 26.0 | 0.30 | 6.00 | 26.1 | 3.16 |
| 6 | 80.3 | 26.0 | 0.40 | 6.00 | 32.1 | 3.32 |

TABLE 2-6-2

Monomer conversion and activity

| Example | Catalyst | C3/C2 ratio | propylene conversion | ethylene conversion | catalyst concentration ppm(metal) | efficiency g metal per g polymer |
|---|---|---|---|---|---|---|
| 1 (comparative) | E | 22.00 | 25.7% | 64.8% | 2.6 | 6,145,944 |
| 2 | G | 30.17 | 53.1% | 99.1% | 25.6 | 235,823 |
| 3 | H | 61.07 | 48.7% | 98.4% | 55.0 | 225,666 |
| 4 | H | 30.34 | 49.7% | 99.0% | 55.0 | 259,545 |
| 5 | H | 20.17 | 46.8% | 98.6% | 55.0 | 259,282 |
| 6 | H | 15.00 | 48.0% | 98.7% | 55.0 | 278,579 |

TABLE 2-6-3

Summary of Polymer Analysis Data

| Example | MFR (g/10 min) | Density (kg/dm3) | Cryst. (%) from density | DSC Tg (° C.) | Tc, o (° C.) | Tc, p (° C.) |
|---|---|---|---|---|---|---|
| 1 | 72 | 0.8809 | 37.9 | −26.1 | 52.3 | 47.6 |
| 2 | 1.7 | 0.8740 | 29.6 | −24.8 | 59.0 | 49.3 |
| 3 | 2.2 | 0.8850 | 42.8 | −10.0 | 76.6 | 64.5 |
| 4 | 2.3 | 0.8741 | 29.7 | −23.2 | 50.8 | 41.6 |
| 5 | 2 | 0.8648 | 18.3 | −27.1 | 30.4 | 10.9 |
| 6 | 2.0 | 0.8581 | 9.9 | −29.6 | — | — |

TABLE 2-6-4

Summary of Polymer Analysis Data

| Example | ΔHc (J/g) | Cryst. (%) (from Hc) | Tm, p (° C.) | Tm, e (° C.) | ΔHf (J/g) | Cryst. (%) (from Hf) |
|---|---|---|---|---|---|---|
| 1 | 40.8 | 24.7 | 91.9 | 114.3 | 52.1 | 31.6 |
| 2 | 27.1 | 16.4 | 64.5 | 128.9 | 38.0 | 23.0 |
| 3 | 45.0 | 27.3 | 102.2 | 145.7 | 65.3 | 39.6 |
| 4 | 30.6 | 18.5 | 67.4 | 145.6 | 42.9 | 26.0 |
| 5 | 8.7 | 5.3 | 50.0 | 119.4 | 13.0 | 7.9 |
| 6 | — | — | — | — | — | — |

TABLE 2-6-5

Summary of Polymer Analysis Data

| Example | Ethylene (wt %)* | Ethylene (mol %)* | Regio-errors 14–16 ppm (mol %)* | Mn (kg/mol) | Mw (kg/mol) | MWD |
|---|---|---|---|---|---|---|
| 1 | 9.5 | 13.6 | 0.00 | 58.5 | 117.4 | 2.0 |
| 2 | 8.2 | 11.8 | 0.24 | 132.6 | 315.7 | 2.4 |
| 3 | 5.6 | 8.2 | 0.46 | 146.0 | 318.3 | 2.2 |
| 4 | 8.2 | 11.8 | 0.34 | 138.5 | 305.7 | 2.2 |
| 5 | 11.1 | 15.8 | 0.35 | | | |
| 6 | 13.2 | 18.6 | 0.37 | 127.5 | 306.8 | 2.4 |

*determined by NMR

TABLE 2-6-6

Summary of Polmer Analysis Data

| Example | % mm* | % mr* | % rr* |
|---|---|---|---|
| 1 | 98.55 | 0 | 1.45 |
| 2 | 93.28 | 1.09 | 5.68 |
| 3 | 94.3 | 2.21 | 3.43 |
| 4 | 96.37 | 0 | 3.63 |
| 5 | 95.3 | 0.0 | 4.66 |
| 6 | 95.17 | 0 | 4.83 |

*corrected PPE + EPE

EXAMPLE 7–8

Homopolymerization of Propylene using Catalyst B and C

Figure 23A:
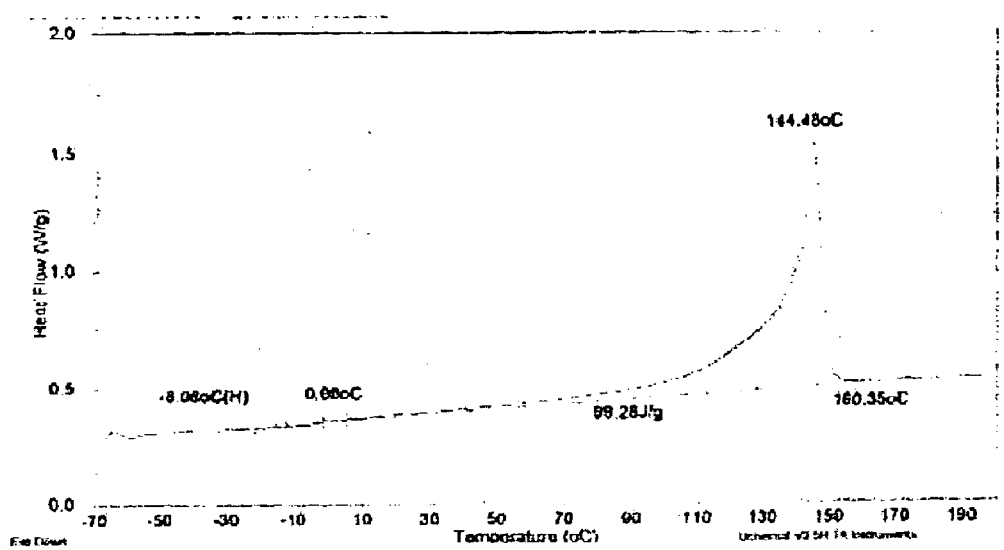
FIGS. 23A and 23B shows the DSC heating and cooling traces of the propylene homopolymer of Example 8, prepared using Catalyst H.
Figure 23B:
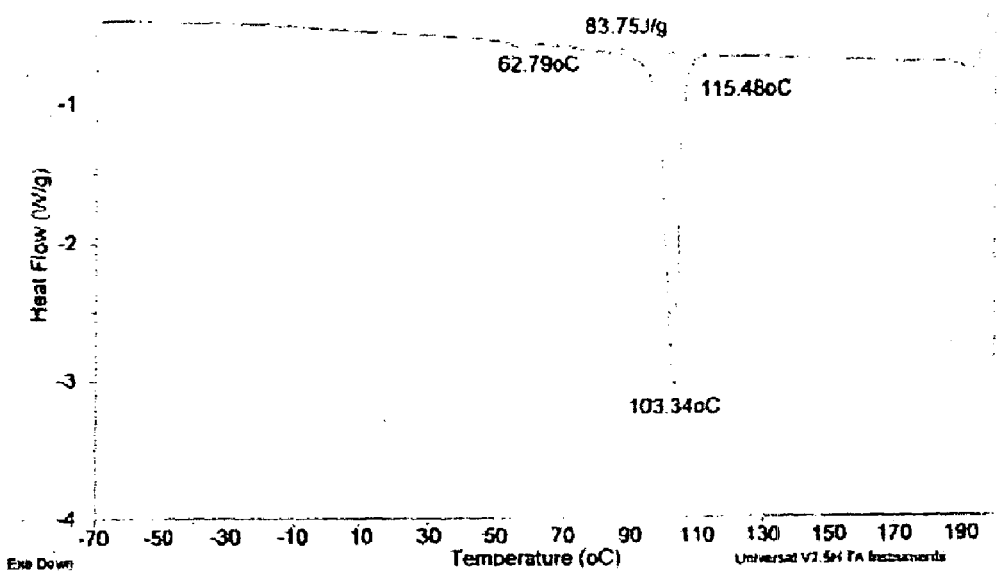

Examples 7–8 were conducted similar to Example 1 without ethylene. The procedure was similar to Example 1 with exceptions noted in Tables 7-8-1 and 7-8-2 below. FIG. 6 shows the $^{13}$C NMR spectrum of the propylene homopolymer product of Example 7 prepared using catalyst G. FIG. 7 shows the $^{13}$C NMR spectrum of the propylene homopolymer product of Example 8 prepared using catalyst H. Both spectra show a high degree of isotacticity, and the expanded Y-axis scale of FIG. 7 relative to FIG. 6 shows more clearly the regio-error peaks. FIGS. 23A and 23B show the DSC heating and cooling traces of the propylene homopolymer of Example 8.

TABLE 7-8-1

Reactor Conditions and Catalyst Activity

| Example | Reactor TEMP DEG C. | SOLV FLOW LB/HR | C3 FLOW LB/HR | H2 FLOW SCCM | POLY LBS/HR WEIGHED | Catalyst | propylene conversion | catalyst concentration ppm(metal) | efficiency g metal per g polymer |
|---|---|---|---|---|---|---|---|---|---|
| 7 | 99.8 | 33.1 | 6.00 | 1.9 | 2.30 | G | 38.3% | 25.6 | 111,607 |
| 8 | 100.3 | 26.0 | 6.00 | 2.6 | 2.57 | H | 42.8% | 32.5 | 100,987 |

TABLE 7-8-2

Polymer Analysis

| Example | MFR (g/10 min) | Density (kg/dm3) | Cryst. (%) from density | DSC Tg (° C.) | Tc, o (° C.) | Tc, p (° C.) | Mn (kg/mol) | Mw (kg/mol) | MWD |
|---|---|---|---|---|---|---|---|---|---|
| 7 | 1.9 | 0.8995 | 59.7 | −6.0 | 104.2 | 100.4 | 114.6 | 350.8 | 2.7 |
| 8 | 2.5 | 0.9021 | 62.7 | −8.1 | 105.7 | 103.3 | 125.5 | 334.0 | 2.7 |

TABLE 7-8-3

Polymer Analysis

| Example | ΔHc (J/g) | Cryst. (%) (from Hc) | Tm, p (° C.) | Tm, e (° C.) | ΔHf (J/g) | Cryst. (%) (from Hf) | Regio-errors 14–16 ppm(mol %)* | % mm | % mr | % rr |
|---|---|---|---|---|---|---|---|---|---|---|
| 7 | 76.9 | 46.6 | 139.7 | 153.5 | 93.7 | 56.8 | 2.69 | 92.12 | 5.79 | 2.08 |
| 8 | 83.6 | 50.7 | 144.5 | 158.2 | 100.6 | 61.0 | 2.36 | 93.93 | 4.45 | 1.62 |

*determined by NMR

EXAMPLE 9

This Example demonstrates a series dual-reactor continuous solution process with the use of a hafnium pyridyl amine catalyst (Catalyst H) in the first reactor to produce high molecular weight isotactic polypropylene and a constrained geometry catalyst (Catalyst B) in the second reactor to produce a lower molecular weight atactic propylene/ethylene copolymer, and recovery of the novel polymer.

Purified ISOPAR-E solvent, ethylene, hydrogen, and 1-octene are supplied to a 1-gallon jacketed reactor equipped with a jacket for temperature control and an internal thermocouple. The solvent feed to the reactor is measured by a mass-flow controller. A variable speed diaphragm pump controls the solvent flow rate and increases the solvent pressure to the reactor. The compressed, liquified propylene feed is measured by a mass flow meter and the flow is controlled by a variable speed diaphragm pump. At the discharge of the pump, a side stream is taken to provide flush flows for the catalyst injection line and the reactor agitator. The remaining solvent is combined with ethylene and hydrogen and delivered to the reactor. The ethylene stream is measured with a mass flow meter and controlled with a Research Control valve. A mass flow controller is used to deliver hydrogen into the ethylene stream at the outlet of the ethylene control valve. The temperature of the solvent/monomer is controlled by use of a heat exchanger before entering the reactor. This stream enters the bottom of the reactor. The catalyst component solutions are metered using pumps and mass flow meters, and are combined with the catalyst flush solvent. This stream enters the bottom of the reactor, but in a different port than the monomer stream. The reactor is run liquid-full at 500 psig with vigorous stirring. The process flow is in from the bottom and out of the top. All exit lines from the reactor are steam traced and insulated.

The exit of the first reactor is connected by insulated piping to a second 1 gallon reactor similarly equipped to the first, with a provision for independent catalyst and cocatalyst addition, and additional monomer, hydrogen, solvent addition and jacket temperature control. After the polymer solution stream exits the second reactor, polymerization is stopped with the addition of a small amount of water, and other additives and stabilizers can be added at this point. The stream flows through a static mixer and a heat exchanger in order to heat the solvent/polymer mixture. The solvent and unreacted monomers are removed at reduced pressure, and the product is recovered by extrusion using a devolatilizing extruder. The extruded strand is cooled under water and chopped into pellets. The operation of the dual-reactor system is controlled with a process control computer.

A 4-L catalyst tank is filled with an ISOPAR E solution of Catalyst H at a concentration of 50 ppm Hf. A second 4 L catalyst tank is filled with a solution of Catalyst B at a concentration of 5.0 ppm Ti. Additional tanks are provided with a solution of N,N-dioctadecylanilinium tetrakis (pentafluorophenyl)borate in ISOPAR E at a concentration of 100 ppm B, and MMAO-3A in ISOPAR E at a concentration of 100 ppm Al. ISOPAR E is continuously fed into the first reactor at 27.0 pounds per hour, and propylene at 6.0 pounds per hour. The Catalyst H solution, along with enough N,N-dioctadecylanilinium tetrakis(pentafluorophenyl) borate in ISOPAR E and MMAO-3A in ISOPAR E to maintain a Hf:B:Al molar ratio of 1:1.2:5 is added to the first reactor at a rate sufficient to maintain a 55% propylene conversion and a reaction temperature of 100° C. The flow rate of Catalyst H is adjusted to maintain a first-reactor product melt flow rate (MFR) of 2.0, while maintaining 55% propylene conversion and a reactor temperature of 100° C. by adjusting the temperature of the reactor jacket and through the addition of hydrogen as a molecular weight control agent. The molar ratio of aluminum can be adjusted in order to optimize the overall catalyst efficiency. The contents of the first reactor flow into the second reactor, where additional solvent (10 pounds/hr) and a mixture of propylene and ethylene (2.0 and 1.0 pounds/hour, respectively) is added at 20° C. The Catalyst B solution, along with enough N,N-dioctadecylanilinium tetrakis (pentafluorophenyl)borate in ISOPAR E and MMAO-3A in ISOPAR E to maintain a Ti:B:Al molar ratio of 1:1.2:5 is added to the second reactor at a rate sufficient to maintain a 80% ethylene conversion and a reaction temperature of 120° C. The flow rate of Catalyst B is adjusted to maintain an overall product melt flow rate (MFR) of 6.0 by adjusting the temperature of the reactor jacket and through the addition of hydrogen as a molecular weight control agent. The molar ratio of aluminum can be adjusted in order to optimize the overall catalyst efficiency. After the post-reactor deactivation of the catalyst, antioxidant is added, and the product is devolatilized and extruded to recover the solid product, which is useful for molding and extrusion, and has good processability and toughness.

EXAMPLE 10

This Example demonstrates a series dual-reactor continuous solution process with the use of a hafnium pyridyl amine catalyst (Catalyst H) in the first reactor to produce high molecular weight isotactic propylene/ethylene copolymer and a metallocene catalyst (Catalyst E) in the second reactor to produce a lower molecular weight isotactic polypropylene, and recovery of the novel polymer. This example demonstrates a high conversion of ethylene in the first reactor, which allows for a more crystalline product to be made in the second reactor.

The procedure of Example 9 is followed except that Catalyst H is added to the first reactor along with 26 pounds/hr of toluene, 6.0 pounds/hr of propylene, and 0.2 pounds/hr of ethylene. The Catalyst H solution, along with enough N,N-dioctadecylanilinium tetrakis (pentafluorophenyl)borate in toluene and PMAO-IP in TOLUENE to maintain a Hf:B:Al molar ratio of 1:1.2.30 is added to the first reactor at a rate sufficient to maintain a 52% propylene conversion and a reaction temperature of 80° C. The flow rate of Catalyst H is adjusted to maintain a first-reactor product melt flow rate (MFR) of 0.2, while maintaining 52% propylene conversion and a reactor temperature of 80° C. by adjusting the temperature of the reactor jacket and through the addition of hydrogen as a molecular weight control agent. At this propylene conversion, the ethylene conversion is about 99%. The molar ratio of aluminum can be adjusted in order to optimize the overall catalyst efficiency. The contents of the first reactor flow into the second reactor, where additional solvent (20 pounds/hr) and propylene (2.0 pounds/hr) is added at 20° C. The Catalyst E solution, along with enough N,N-dioctadecylanilinium tetrakis(pentafluorophenyl)borate in ISOPAR E and MMAO-3A in ISOPAR E to maintain a Zr:B:Al molar ratio of 1:1.2:5 is added to the second reactor at a rate sufficient to maintain the reactor temperature at 100° C. The flow rate of Catalyst E is adjusted to maintain the temperature at 100° C. and an overall product melt flow rate (MFR) of 20 by adjusting the temperature of the reactor jacket and through the addition of hydrogen as a molecular weight control agent as needed. The molar ratio of aluminum can be adjusted in order to optimize the overall catalyst efficiency. After the post-reactor deactivation of the catalyst, antioxidant is added, and the product is devolatilized and extruded to recover the novel solid product, which has a broad molecular weight distribution, and has good processability and toughness.

EXAMPLE 11

This Example demonstrates a series dual-reactor continuous solution process with the use of a hafnium pyridyl amine catalyst (Catalyst H) in the first reactor to produce high molecular weight isotactic polypropylene and a metallocene catalyst (Catalyst F) in the second reactor to produce a lower molecular weight isotactic polypropylene having a lower tacticity than the first reactor polymer, and recovery of the novel polymer.

The procedure of Example 10 is followed except that Catalyst H is added to the first reactor along with 26 pounds/hour of toluene, and 7.0 pounds/hr of propylene. The Catalyst H solution, along with enough N,N-dioctadecylanilinium tetrakis(pentafluorophenyl)borate in toluene and PMAO-IP in toluene to maintain a Hf:B:Al molar ratio of 1:1.2:30 is added to the first reactor at a rate sufficient to maintain a 52% propylene conversion and a reaction temperature of 90° C. The flow rate of Catalyst H is adjusted to maintain a first-reactor product melt flow rate (MFR) of 0.10, while maintaining 52% propylene conversion and a reactor temperature of 90° C. by adjusting the temperature of the reactor jacket and through the addition of hydrogen as a molecular weight control agent, as needed. The molar ratio of aluminum can be adjusted in order to optimize the overall catalyst efficiency. The contents of the first reactor flow into the second reactor, where additional solvent (20 pounds/hr) and propylene (2.0 pounds/hr) is added at 20° C. The Catalyst F solution, along with enough N,N-dioctadecylanilinium tetrakis(pentafluorophenyl) borate in toluene and PMAO-IP in toluene to maintain a Zr:B:Al molar ratio of 1:1.2:5 is added to the second reactor at a rate sufficient to maintain the reactor temperature at 120° C. The flow rate of Catalyst F is adjusted to maintain the temperature at 120° C. and an overall product melt flow rate (MFR) of 12 by adjusting the temperature of the reactor jacket and through the addition of hydrogen as a molecular weight control agent as needed. The molar ratio of aluminum can be adjusted in order to optimize the overall catalyst efficiency. After the post-reactor deactivation of the catalyst, antioxidant is added, and the product is devolatilized and extruded to recover the novel solid product, which has a very broad molecular weight distribution, and has good processability and is useful for molding applications, among others.

EXAMPLE 12

This Example demonstrates a series dual-reactor continuous solution process with the use of a hafnium pyridyl amine catalyst (Catalyst H) in the first reactor to produce high molecular weight isotactic propylene/ethylene copolymer and a constrained geometry catalyst (Catalyst C) in the second reactor to produce a high molecular weight atactic ethylene/propylene copolymer, and recovery of the novel polymer.

The procedure of Example 9 is followed except that Catalyst H is added to the first reactor along with 26 pounds/hr of ISOPAR-E, 6.0 pounds/hr of propylene, and 0.2 pounds/hr of ethylene. The Catalyst H solution, along with enough N,N-dioctadecylanilinium tetrakis (pentafluorophenyl)borate in ISOPAR E and MMAO-3A in ISOPAR E to maintain a Hf:B:Al molar ratio of 1:1.2:5 is added to the first reactor at a rate sufficient to maintain a 55% propylene conversion and a reaction temperature of 80° C. The flow rate of Catalyst H is adjusted to maintain a first-reactor product melt flow rate (MFR) of 6.0, while maintaining 55% propylene conversion and a reactor temperature of 80° C. by adjusting the temperature of the reactor jacket and through the addition of hydrogen as a molecular weight control agent. At this propylene conversion, the ethylene conversion is about 99%. The molar ratio of aluminum can be adjusted in order to optimize the overall catalyst efficiency. The contents of the first reactor flow into the second reactor, where additional solvent (22 pounds/hr) and ethylene (3.0 pounds/hr) is added at 20 degrees C. The Catalyst C solution, along with enough N,N-dioctadecylanilinium tetrakis(pentafluorophenyl)borate in ISOPAR E and MMAO-3A in ISOPAR E to maintain a Ti:B:Al molar ratio of 1:1.2:5 is added to the second reactor at a rate sufficient to maintain the reactor temperature at 160° C. The flow rate of Catalyst C is adjusted to maintain the temperature at 160° C. and an overall product melt flow rate (MFR) of 2.0 by adjusting the temperature of the reactor jacket and through the addition of hydrogen as a molecular weight control agent as needed. The molar ratio of aluminum can be adjusted in order to optimize the overall catalyst efficiency. After the post-reactor deactivation of the catalyst, antioxidant is added, and the product is devolatilized and extruded to recover the novel solid product, which has a broad molecular weight distribution, and has good processability and very good toughness.

EXAMPLE 13

This Example demonstrates a series dual-reactor continuous solution process with the use of a hafnium pyridyl amine catalyst (Catalyst H) in the first reactor to produce high molecular weight isotactic polypropylene and a constrained geometry catalyst (Catalyst A) in the second reactor to produce a lower molecular weight atactic polypropylene, and recovery of the novel polymer.

The procedure of Example 9 is followed except that Catalyst H is added to the first reactor along with 26 pounds/hr of ISOPAR-E, and 6.0 pounds/hour of propylene. The Catalyst H solution, along with enough N,N-dioctadecylanilinium tetrakis(pentafluorophenyl)borate in ISOPAR E and MMAO-3A in ISOPAR E to maintain a Hf:B:Al molar ratio of 1:1.2:5 is added to the first reactor at a rate sufficient to maintain a 50% propylene conversion and a reaction temperature of 90° C. The flow rate of Catalyst H is adjusted to maintain a first-reactor product melt flow rate (MFR) of 0.1, while maintaining 50% propylene conversion and a reactor temperature of 90° C. by adjusting the temperature of the reactor jacket and through the addition of hydrogen as a molecular weight control agent. The molar ratio of aluminum can be adjusted in order to optimize the overall catalyst efficiency. The contents of the first reactor flow into the second reactor, where additional solvent (22 pounds/hr) and propylene (3.0 pounds/hr) is added at 20° C. The Catalyst A solution, along with enough N,N-dioctadecylanilinium tetrakis(pentafluorophenyl)borate in ISOPAR E and MMAO-3A in ISOPAR E to maintain a Ti:B:Al molar ratio of 1:1.2:5 is added to the second reactor at a rate sufficient to maintain the reactor temperature at 120° C. The flow rate of Catalyst C is adjusted to maintain the temperature at 120° C. and an overall product melt flow rate (MFR) of 25 by adjusting the temperature of the reactor jacket and through the addition of hydrogen as a molecular weight control agent as needed. The molar ratio of aluminum can be adjusted in order to optimize the overall catalyst efficiency. After the post-reactor deactivation of the catalyst, antioxidant is added, and the product is devolatilized and extruded to recover the novel solid product, which has a very broad molecular weight distribution, and has good processability.

EXAMPLE 14

This Example demonstrates a series dual-reactor continuous solution process with the use of a hafnium pyridyl amine catalyst (Catalyst H) in the first reactor to produce high molecular weight isotactic propylene/ethylene copolymer and a constrained geometry catalyst (Catalyst D) in the second reactor to produce a lower molecular weight ethylene/styrene/propylene terpolymer, and recovery of the novel polymer.

The procedure of Example 10 is followed except that Catalyst H is added to the first reactor along with 26 pounds/hour of toluene, and 6.0 pounds/hour of propylene, and 0.3 pounds/hour of ethylene. The Catalyst H solution, along with enough N,N-dioctadecylanilinium tetrakis (pentafluorophenyl)borate in toluene and PMAO-IP in toluene to maintain a Hf:B:Al molar ratio of 1:1.2:30 is added to the first reactor at a rate sufficient to maintain a 50% propylene conversion and a reaction temperature of 80° C. The flow rate of Catalyst H is adjusted to maintain a first-reactor product melt flow rate (MFR) of 0.1, while maintaining 50% propylene conversion and a reactor temperature of 80° C. by adjusting the temperature of the reactor jacket and through the addition of hydrogen as a molecular weight control agent. The molar ratio of aluminum can be adjusted in order to optimize the overall catalyst efficiency. The contents of the first reactor flow into the second reactor, where additional solvent (22 pounds/hr) and styrene and ethylene (3.0 and 3.5 pounds/hr each, respectively) is added at 20° C. The Catalyst D solution, along with enough N,N-dioctadecylanilinium tetrakis(pentafluorophenyl) borate in toluene and PMAO-IP in toluene to maintain a Ti:B:Al molar ratio of 1:1.2:10 is added to the second reactor at a rate sufficient to maintain the reactor temperature at 120° C. The flow rate of Catalyst D is adjusted to maintain the temperature at 120° C. and an overall product melt flow rate (MFR) of 3.5 by adjusting the temperature of the reactor jacket and through the addition of hydrogen as a molecular weight control agent as needed. The molar ratio of aluminum can be adjusted in order to optimize the overall catalyst efficiency. After the post-reactor deactivation of the catalyst, antioxidant is added, and the product is devolatilized and extruded to recover the novel solid product, which is tough and can be used for a variety of molding and extrustion applications, and can be easily sulfonated with chlorosulfonic acid to produce a novel material, if desired.

EXAMPLE 15

This Example demonstrates a batch reactor polymerization using Catalyst H. This example provides a simple and convenient procedure for preparing small quantities of the polymers of this invention. Because the peak positions of $^{13}C$ chemical shifts may vary somewhat from instrument to instrument depending on the specifics of the solvent, temperature, and other experimental details, this example may be used to prepare a sample of polymer for the skilled artisan to precisely measure and identify the chemical shifts of the regioerror peaks which are found at about 14.6 and 15.7 ppm.

Preparation of Antioxidant/Stabilizer Additive solution: The additive solution was prepared by dissolving 6.66 g of Irgaphos 168 and 3.33 g of Irganox 1010 in 500 mL of toluene. The concentration of this solution is therefore 20 mg of total additive per 1 mL of solution.

General 1-Gallon Solution Semi-Batch Reactor Propylene/Ethylene Polymerization Procedure: Solution semi-batch reactor polymerization of propylene and ethylene are carried out in a 1 gallon metal autoclave reactor equipped with a mechanical stirrer, a jacket with circulating heat transfer fluid, which can be heated or cooled in order to control the internal reactor temperature, an internal thermocouple, pressure transducer, with a control computer and several inlet and output valves. Pressure and temperature are continuously monitored during the polymerization reaction. Measured amounts of propylene are added to the reactor containing about 1000 g Isopar E as solvent. The reactor is heated up to the reaction temperature with stirring (typically about 1,000 rpm or higher) and then the desired amount of ethylene is added through a mass flow meter. The active catalyst is prepared in a drybox by syringing together solutions of the appropriate catalyst, cocatalyst, and any scavenger (if desired) components with additional solvent to give a total volume which can be conveniently added to the reactor (typically 10–20 mL total). If desired, a portion of the scavenger (typically an aluminum alkyl, alumoxane, or other alkyl-aluminum compound) may be added to the reactor separately prior to the addition on the active catalyst solution. The active catalyst solution is then transferred by syringe to a catalyst addition loop and injected into the reactor over approximately 2.5 minutes using a flow of high pressure solvent. Immediately following the desired polymerization time, stirring and heating are stopped. The polymer solution is then dumped from the reactor using a bottom-valve through a heated transfer line into a nitrogen-purged glass kettle. An aliquot of the additive solution described above is added to this kettle and the solution stirred thoroughly (the amount of additive used is chosen based on the total polymer produced, and is typically targeted at a level of about 1000–2000 ppm). The polymer solution is dumped into a tray, air dried overnight, then thoroughly dried in a vacuum oven for two days. The weights of the polymers are recorded and the efficiency calculated as grams of polymer per gram of transition metal.

Homopolymerization of propylene using Catalyst H: Using the general solution semi-batch reactor polymerization procedure described above, 507 g of propylene was added along with 1402 g of ISOPAR-E. This was heated to 110° C. A catalyst solution was prepared by combining solutions of Catalyst H, Armeenium borate, and PMAO-IP to give 3 micromoles of Hf, 3 micromoles of Armeenium borate, and 600 micromoles of Al. The catalyst solution was added to the reactor as described in the general procedure. After 10 minutes reaction time, the bottom valve was opened and the reactor contents transferred to the glass kettle. The additive solution was added and the polymer solution was stirred to mix well. The contents were poured into a glass pan, cooled and allowed to stand in a hood overnight, and dried in a vacuum oven for 2 days. The isolated polymer yield was 50.1 grams. The Mw was 293,000 and the Mn was 100,000. The polymer melting point was 144.4° C.

EXAMPLE 16

This example demonstrates the calculation of B values for certain of the Examples disclosed herein. The polymer from Comparative Example 1 is analyzed as follows. The data was collected using a Varian UNITY Plus 400 MHz NMR spectrometer, corresponding to a $^{13}C$ resonance frequency of 100.4 MHz. Acquisition parameters were selected to ensure quantitative $^{13}C$ data acquisition in the presence of the relaxation agent. The data was acquired using gated $^1H$ decoupling, 4000 transients per data file, a 7 sec pulse repetition delay, spectral width of 24,200 Hz and a file size of 32K data points, with the probe head heated to 130° C. The sample was prepared by adding approximately 3 mL of a 50/50 mixture of tetrachloroethane-d2/orthodichlorobenzene that is 0.025M in chromium acetylacetonate (relaxation agent) to 0.4 g sample in a 10 mm NMR tube. The headspace of the tube was purged of oxygen by displacement with pure nitrogen. The sample was dissolved and homogenized by heating the tube and its contents to 150° C., with periodic refluxing initiated by heat gun.

Following data collection, the chemical shifts were internally referenced to the mmmm pentad at 21.90 ppm.

For propylene/ethylene copolymers, the following procedure is used to calculate the percent ethylene in the polymer. Integral regions are determined as follows:

TABLE 16-1

| Integral Regions for Calculating % Ethylene | | |
|---|---|---|
| Region designation | Ppm | Integral area |
| A | 44–49 | 259.7 |
| B | 36–39 | 73.8 |
| C | 32.8–34 | 7.72 |
| P | 31.0–30.8 | 64.78 |
| Q | Peak at 30.4 | 4.58 |
| R | Peak at 30 | 4.4 |
| F | 28.0–29.7 | 233.1 |
| G | 26–28.3 | 15.25 |
| H | 24–26 | 27.99 |
| I | 19–23 | 303.1 |

Region D is calculated as follows: D=P−(G−Q)/2.
Region E is calculated as follows: E=R+Q+(G−Q)/2.
The triads are calculated as follows:

TABLE 16-2

| Traid Calculation |
|---|
| PPP = (F + A − 0.5D)/2 |
| PPE = D |
| EPE = C |
| EEE = (E − 0.5G)/2 |
| PEE = G |
| PEP = H |
| Moles P = (B + 2A)/2 |
| Moles E = (E + G + 0.5B + H)/2 |

For this example, the mole % ethylene is calculated to be 13.6 mole %.

For this example, the triad mole fractions are calculated to be as follows:

TABLE 16-3

Triad Mole Calculation

PPP = 0.6706
PPE = 0.1722
EPE = 0.0224
EEE = 0.0097
PEE = 0.0442
EPE = 0.0811

From this, the B value is calculated to be (0.172+0.022+0.044+0.081)/2 (0.136×0.864)=1.36 In a similar manner, the B values for the following examples are calculated to be:

TABLE 16-4

B-Value Calculation

| Example | B Value |
|---|---|
| Comparative 1 | 1.36 |
| 2 | 1.68 |
| 3 | 1.7 |
| 4 | 1.78 |
| 6 | 1.7 |

EXAMPLE 17

Table 17 is a summary showing the skewness index, $S_{ix}$, for inventive and prior art samples. All of the samples were prepared and measured as described in Table C in the Description of the Preferred Embodiments and entitled Parameters Used for TREF. The copolymers of the invention have a skewness index greater than about (−1.2). The results from Table 17 are represented graphically in FIG. 22.

The inventive examples show unusual and unexpected results when examined by TREF. The distributions tend to cover a large elution temperature range while at the same time giving a prominent, narrow peak. In addition, over a wide range of ethylene incorporation, the peak temperature, $T_{max}$, is near 60° C. to 65° C. In the prior art, for similar levels of ethylene incorporation, this peak moves to higher elution temperatures with lower ethylene incorporation.

For conventional metallocene catalysts the approximate relationship of the mole fraction of propylene, $X_p$, to the TREF elution temperature for the peak maximum, $T_{Max}$, is given by the following equation:

$$Log_e(X_p) = -289/(273+T_{max}) + 0.74$$

For the inventive copolymers, the natural log of the mole fraction of propylene, LnP, is greater than that of the conventional metallocenes, as aiown in this equation:

$$LnP > -289/(273+T_{max}) + 0.75$$

TABLE 17

Summary of Skewness Index Results

| Inventive | Catalyst Type | Ethylene Content (Mole %) | Elution Temperature of Peak maximum (° C.) | Inventive $S_{ix}$ |
|---|---|---|---|---|
| Sample 17-1 | Catalyst H | 8.2 | 61.4 | 0.935 |
| Sample 17-2 | Catalyst J | 8.9 | 60.8 | −0.697 |

TABLE 17-continued

Summary of Skewness Index Results

| Inventive | Catalyst Type | Ethylene Content (Mole %) | Elution Temperature of Peak maximum (° C.) | Inventive $S_{ix}$ |
|---|---|---|---|---|
| Sample 17-3 | Catalyst J | 8.5 | 61.4 | −0.642 |
| Sample 17-4 | Catalyst J | 7.6 | 65.0 | 0.830 |
| Sample 17-5 | Catalyst J | 7.6 | 65.0 | 0.972 |
| Sample 17-6 | Catalyst J | 8.6 | 61.4 | 0.804 |
| Sample 17-7 | Catalyst J | 9.6 | 60.2 | −0.620 |
| Sample 17-8 | Catalyst J | 12.4 | 60.2 | 0.921 |
| Sample 17-9 | Catalyst J | 8.6 | 60.8 | −0.434 |
| Sample 17-10 | Catalyst J | 8.6 | 62.0 | 1.148 |
| Sample 17-11 | Catalyst H |  | 57.8 | 1.452 |
| Sample 17-12 | Catalyst J |  | 78.2 | 1.006 |
| Sample 17-13 | Catalyst H | 4.4 | 80.0 | −1.021 |
| Sample 17-14 | Catalyst E | 7.6 | 80.6 | −1.388 |
| Sample 17-15 | Catalyst E | 10.0 | 70.4 | −1.278 |
| Sample 17-16 | Catalyst E | 10.7 | 66.2 | −1.318 |
| Sample 17-17 | Catalyst F | 11.1 | 69.2 | −1.296 |
| Sample 17-18 | Catalyst E | 10.6 | 65.6 | −1.266 |

EXAMPLE 18

DSC analysis shows that propylene/ethylene copolymers produced by a solution polymerization process using a nonmetallocene, metal-centered, pyridal-amine ligand catalyst have melting behavior that differs in surprising ways from propylene/ethylene copolymers produced by metallocene polymerization processes that are known in the art. The different melting behavior of these copolymers compared to that of copolymers that are known in the art not only demonstrates the novelty of these materials, but also can be used to infer certain advantages of these materials for some applications. The novel aspects of the melting behavior of these copolymers and their associated utility are discussed below, after first describing the DSC analysis method.

Any volatile materials (e.g., solvent or monomer) are removed from the polymer prior to DSC analysis. A small amount of polymer, typically five to fifteen milligrams, is accurately weighed into an aluminum DSC pan with lid. Either hermetic or standard type pans are suitable. The pan containing the sample is then placed on one side of the DSC cell, with an empty pan with lid placed on the reference side of the DSC cell. The DSC cell is then closed, with a slow purge of nitrogen gas through the cell during the test. Then the sample is subjected to a programmed temperature sequence that typically has both isothermal segments and segments where the temperature is programmed to increase or decrease at a constant rate. Results that are presented here were all obtained using heat-flux type DSC instruments manufactured by TA Instruments (e.g., Model 2910 DSC). The measurement principles underlying heat-flux DSC are described on page 16 of Turi, ibid. The primary signals generated by such instruments are temperature (units: ° C.) and differential heat flow (units: watts) into or out of the sample (i.e., relative to the reference) as a function of elapsed time. Melting is endothermic and involves excess heat flow into the sample relative to the reference, whereas crystallization is exothermic and involves excess heat flow out of the sample. These instruments are calibrated using indium and other narrow-melting standards. Calibration ensures that the temperature scale is correct and for the proper correction of unavoidable heat losses.

Temperature programs for DSC analysis of semi-crystalline polymers involve several steps. Although the temperature programs used to generate the data presented here differed in some details, the critical steps were maintained constant throughout. The first step is an initial heating to a temperature sufficient to completely melt the sample; for polypropylene homopolymers and copolymers, this is 210° C. or higher. This first step also helps insure excellent thermal contact of the polymer sample with the pan. Although details of this first step differed for data presented here—for example, the rate of heating, the upper temperature, and the hold time at the upper temperature—in all cases the choices were sufficient to achieve the principal objectives of this step, of bringing all samples to a common completely melted starting point with good thermal contact. The second step involves cooling at a constant rate of 10° C./min from an upper temperature of at least 210° C. to a lower temperature of 0° C. or less. The lower temperature is chosen to be at or slightly below the glass transition temperature of the particular propylene polymer. The rate of crystallization becomes very slow at the glass transition temperature; hence, additional cooling will have little effect on the extent of crystallization. This second step serves to provide a standard crystallization condition, prior to examining subsequent melting behavior. After a brief hold at this lower temperature limit, typically one to three minutes, the third step is commenced. The third step involves heating the sample from a temperature of 0° C. or lower (i.e., the final temperature of the previous step) to 210° C. or higher at a constant rate of 10° C./min. This third step serves to provide a standard melting condition, as preceded by a standard crystallization condition. All the melting behavior results presented here were obtained from this third step, that is, from the second melting of the sample.

The output data from DSC consists of time (sec), temperature (° C.), and heat flow (watts). Subsequent steps in the analysis of melting endotherms are as follows. First, the heat flow is divided by the sample mass to give specific heat flow (units: W/g). Second, a baseline is constructed and subtracted from the specific heat flow to give baseline-subtracted heat flow. For the analyses presented here, a straight-line baseline is used. The lower temperature limit for the baseline is chosen as a point on the high temperature side of the glass transition. The upper temperature limit for the baseline is chosen as a temperature about 5–10° C. above the completion of the melting endotherm. Although a straight-line baseline is theoretically not exact, it offers greater ease and consistency of analysis, and the error introduced is relatively minor for samples with specific heats of melting of about 15–20 Joules per gram or higher. Employing a straight-line baseline in lieu of a more theoretically correct baseline does not substantively affect any of the results or conclusions presented below, although the fine details of the results would be expected to change with a different prescription of the instrumental baseline.

There are a number of quantities that can be extracted from DSC melting data. Quantities that are particularly useful in demonstrating differences or similarities among different polymers are: (1) the peak melting temperature, $T_{max}$ (° C.), which is the temperature at which the baseline-subtracted heat flow is a maximum (here the convention is that heat flow into the sample is positive); (2) the specific heat of melting, $\Delta h_m$ (J/g), which is the area under the melting endotherm obtained by integrating the baseline-subtracted heat flow (dq/dt) (W/g) versus time between the baseline limits; (3) the specific heat flow $(dq/dt)_{max}$ (W/g) at the peak melting temperature; (4) the peak specific heat flow normalized by the specific heat of melting, $\{(dq/dt)_{max}/\Delta h_m\}$ (sec$^{-1}$); (5) the first moment $T_1$ of the melting endotherm, defined and calculated as described below; (6) the variance $V_1$ (° C.$^2$) of the melting endotherm relative to the first moment $T_1$, defined and calculated as described below; and (7) the square root of the variance, $V_1^{1/2}$ (° C.), which is one measure of the breadth of the melting endotherm.

Treatment of the melting endotherm as a distribution is a useful way to quantify its breadth. The quantity that is distributed as a function of temperature is the baseline-subtracted heat flow (dq/dt). That this is also a distribution of temperature is made explicit using the calculus chain rule, (dq/dt)=(dq/Dt)(Dt/dt) where (Dt/dt) is the heating rate. The standard definition of the first moment $T_1$ of this distribution is given by the following equation, where the integrations are carried out between the baseline limits. All integrations are most reliably performed as (dq/dt) versus time, as opposed to the alternative (dq/Dt) versus temperature. In the following equation, (dq/dt) and T are the specific heat flow and temperature at time t.

$$T_1 = \frac{\int T \cdot (dq/dt)dt}{\int (dq/dt)dt}$$

The variance $V_1$ relative to the first moment is then standardly defined as:

$$V_1 = \frac{\int (T-T_1)^2 \cdot (dq/dt)dt}{\int (dq/dt)dt}$$

Both $V_1$ and $V_1^{1/2}$ are measures of the breadth of the melting endotherm.

Results of DSC analyses of both inventive and comparative polymers are shown in Table 18-1. All the samples are propylene/ethylene copolymers, with the exception of Samples 1–4 and 17 which are homopolymers. Polymers 1–16 were made using Catalyst H in a solution process. Polymers 17–27 were made with Catalyst E in a solution process. An idea of the precision of the experimental method plus the data analysis procedure is provided by replicates (polymers 17, 20, and 22) and by the consistency of results for sets of polymers that were synthesized under nearly identical conditions (polymers 1–4, 7–9, 10–12, and 13–16).

Figure 24:
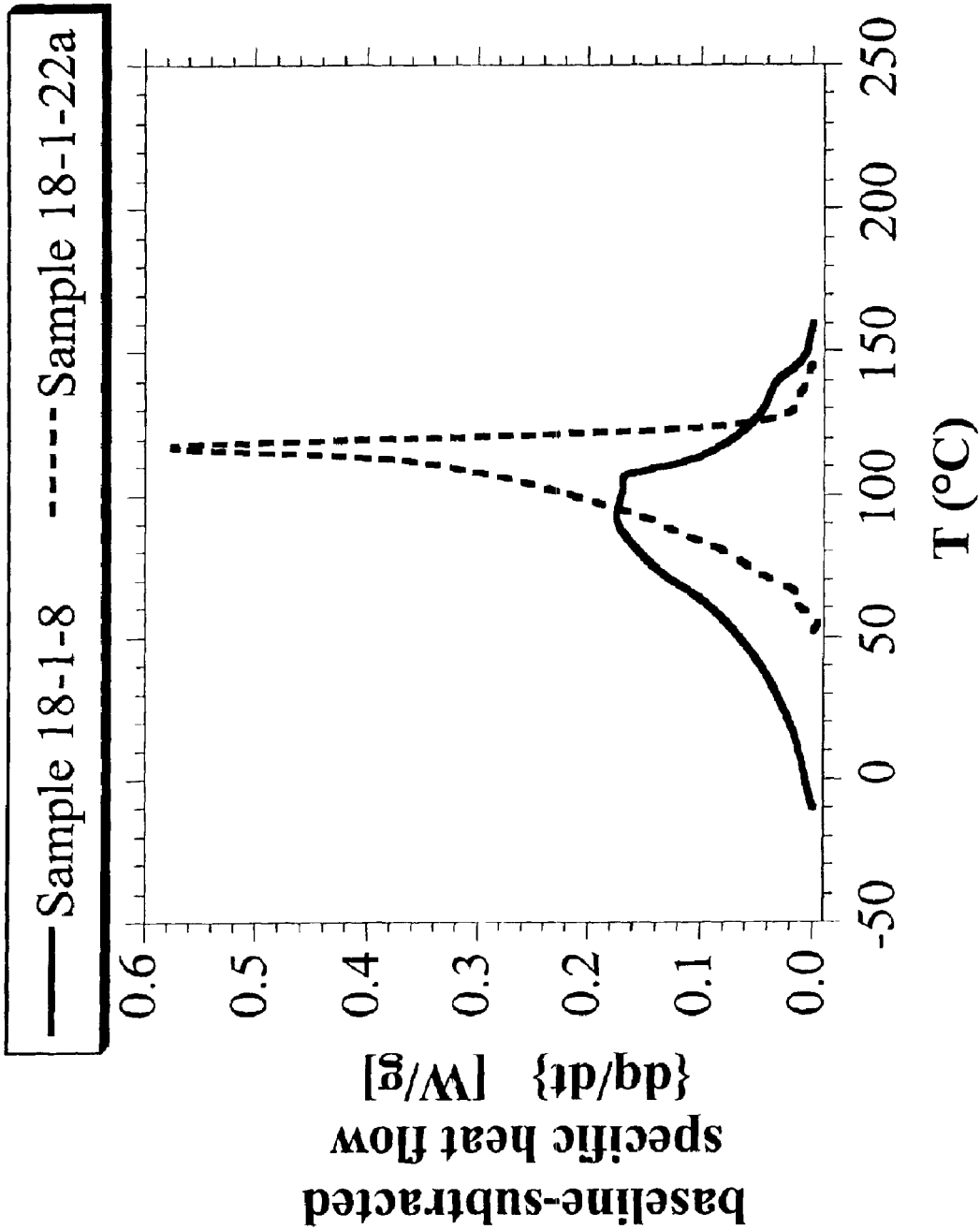
FIG. 24 compares the melting endotherms of Samples 8 and 22a of Example 18.

Differences in melting behavior are most easily seen with the aid of figures. FIG. 24 compares the melting endotherms of Samples 8 and 22a. These two propylene/ethylene copolymers have nearly equivalent heats of melting and mole percent ethylene contents, about 71 J/g and 8 mole %. However, despite these similarities, the melting behavior of the inventive copolymer (Sample 8) is surprisingly different than that of the comparative copolymer (Sample 22a). The melting endotherm of Sample 8 is shifted towards lower temperatures and significantly broadened, when comparing at equivalent heat of melting. These changes in melting behavior are unique to and characteristic of the copolymers of this invention.

Comparison at equivalent heats of melting is particularly meaningful and relevant. This is because equivalent heats of melting implies approximately equal levels of crystallinity, which in turn implies that the room temperature moduli should be similar. Therefore, at a given modulus or stiffness, the copolymers of this invention possess usefully broadened melting ranges compared to typical non-inventive copolymers.

FIGS. 25–29, which are derived from the results in Table 18-1, further highlight the differences in melting behavior for the copolymers of this invention compared to typical copolymers. For all five of these figures, quantities are plotted as functions of the heat of melting, which as described above is an especially meaningful and relevant basis for making intercomparisons and inferring utility. For these plots, data have broken into two series based on the catalyst type used to make the polymer, either metallocene or nonmetallocene type.

Figure 25:
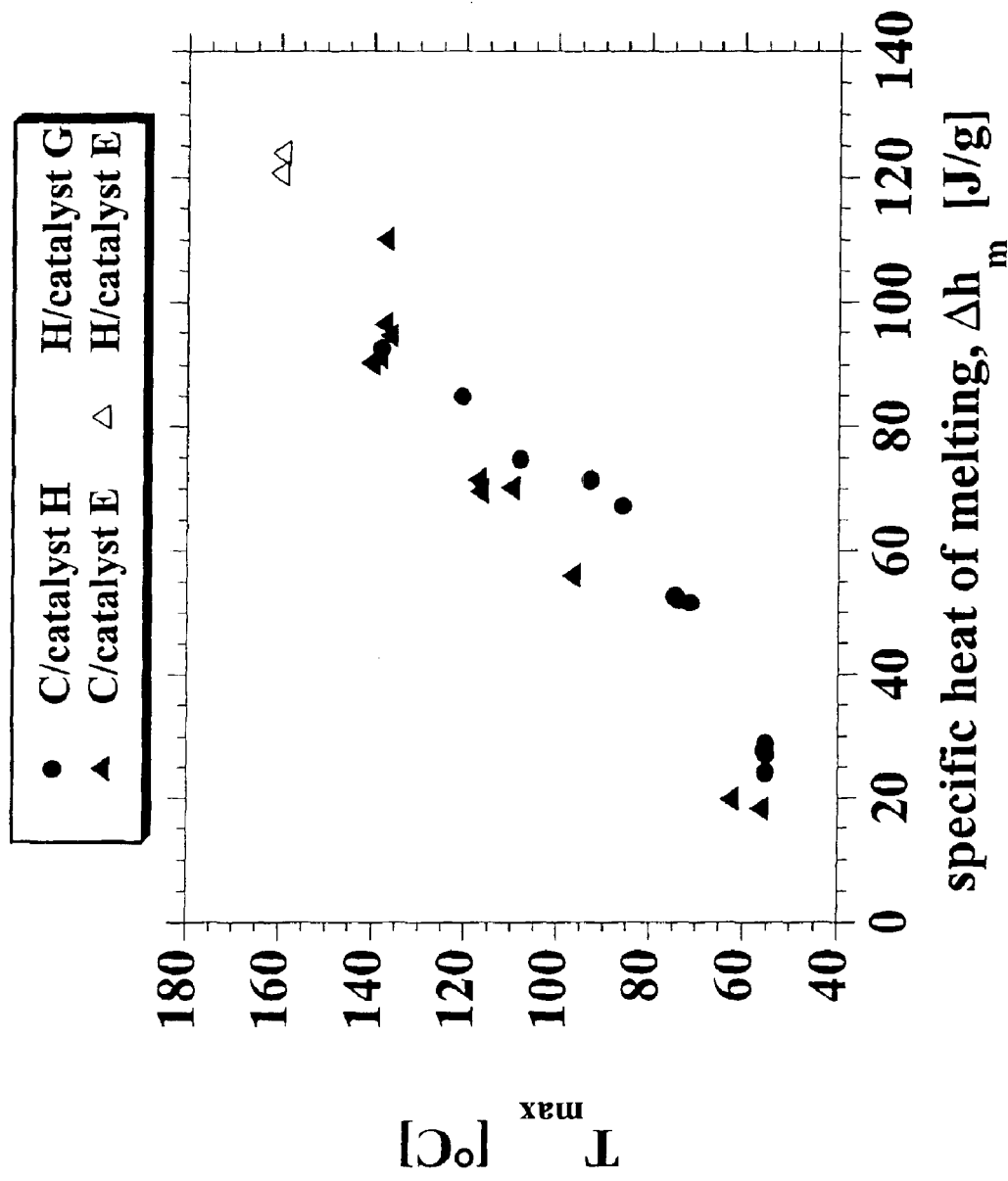
FIG. 25 demonstrates the shift in peak melting temperature towards lower temperature for samples of the copolymers of this invention of Example 18.

FIG. 25 demonstrates how the peak melting temperature is shifted towards lower temperature for the copolymers of this invention. All the changes in melting behavior, of which this shift in peak melting temperature is but one example, imply that there are differences in the crystalline structure at the level of crystal lamellae or other type of primary crystalline elements. In turn, such differences in crystalline structure can most reasonably be attributed to differences in microstructure, for example, the different type of misinsertion errors or the higher B values that characterize the polymers of this invention. Regardless of the exact nature of the microstructural features that give rise to the changes in melting behavior, the changes are in and of themselves evidence that the copolymers of this invention are novel compositions.

Figure 26:
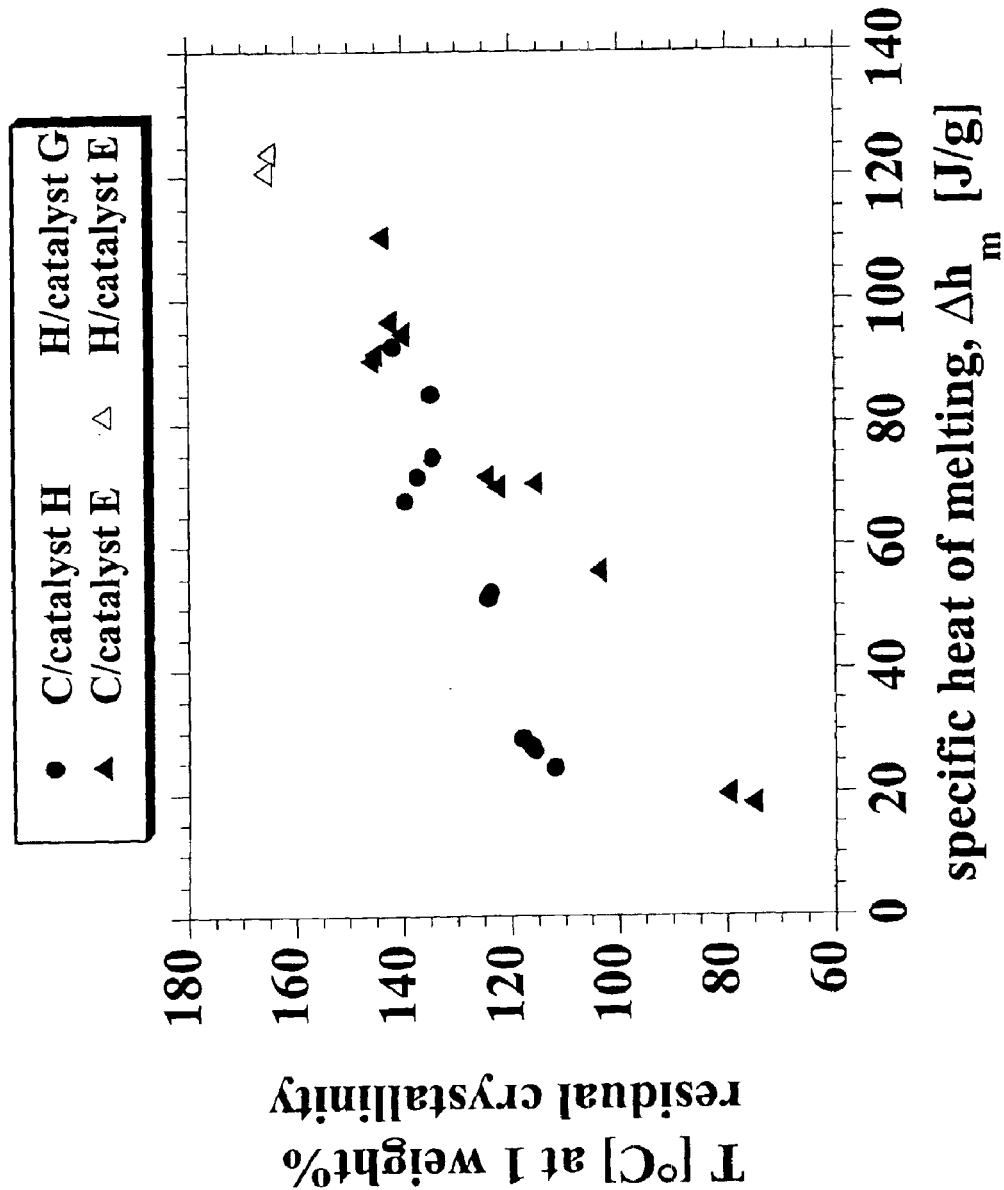
FIG. 26 is a plot of the temperature at which approximately 1 percent crystallinity remains in DSC samples of Example 18.

FIG. 26 which shows a plot of the temperature $T_{1\%c}$ at which there is approximately 1% residual crystallinity, demonstrates another surprising aspect of the melting behavior of the copolymers of this invention. The factor that is used to convert specific heat of melting into nominal weight % crystallinity is 165 J/g=100 weight % crystallinity. (Use of a different conversion factor could change details of the results but not substantive conclusions.) With this conversion factor, the total crystallinity of a sample (units: weight % crystallinity) is calculated as 100% times $\Delta h_m$ divided by 165 J/g. And, with this conversion factor, 1% residual crystallinity corresponds to 1.65 J/g. Therefore, $T_{1\%c}$ is defined as the upper limit for partial integration of the melting endotherm such that $\Delta h_m$ minus the partial integral equals 1.65 J/g, where the same lower limit and baseline are used for this partial integration as for the complete integration. Surprisingly, for nonmetallocene-catalyzed copolymers as compared to metallocene-catalyzed copolymers, this 1% residual crystallinity temperature shifts downward less rapidly with increase in ethylene level (i.e., with decrease in the heat of melting). This behavior of $T_{1\%c}$ is similar to that of the final temperature of melting $T_{me}$.

Figure 27:
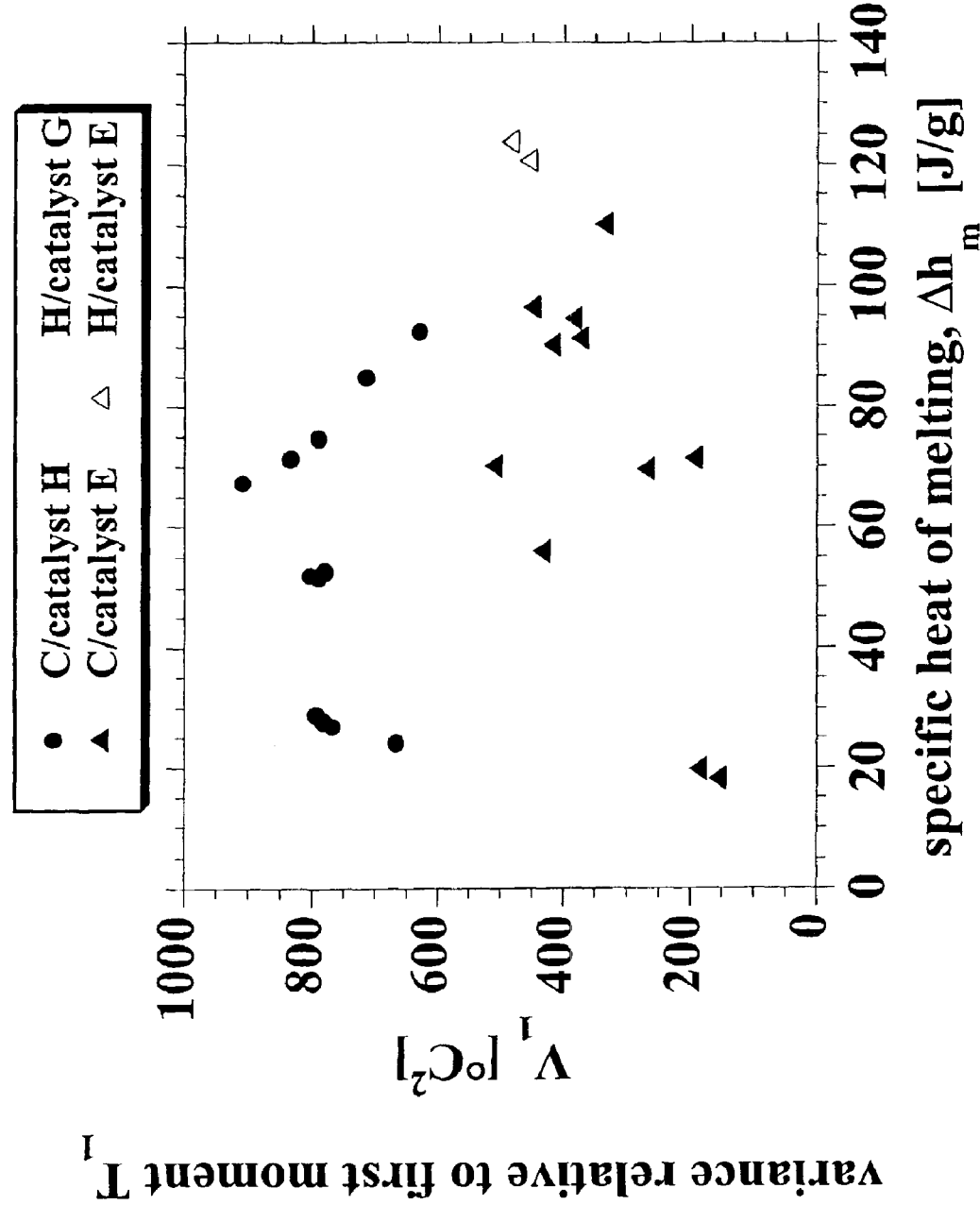
FIG. 27 shows the variance relative to the first moment of the melting endotherm as a function of the heat of melting of various samples of Example 18.

FIG. 27, which shows the variance relative to the first moment of the melting endotherm as a function of the heat of melting, demonstrates directly the greater breadth of the melting endotherm for the copolymers of this invention.

Figure 28:
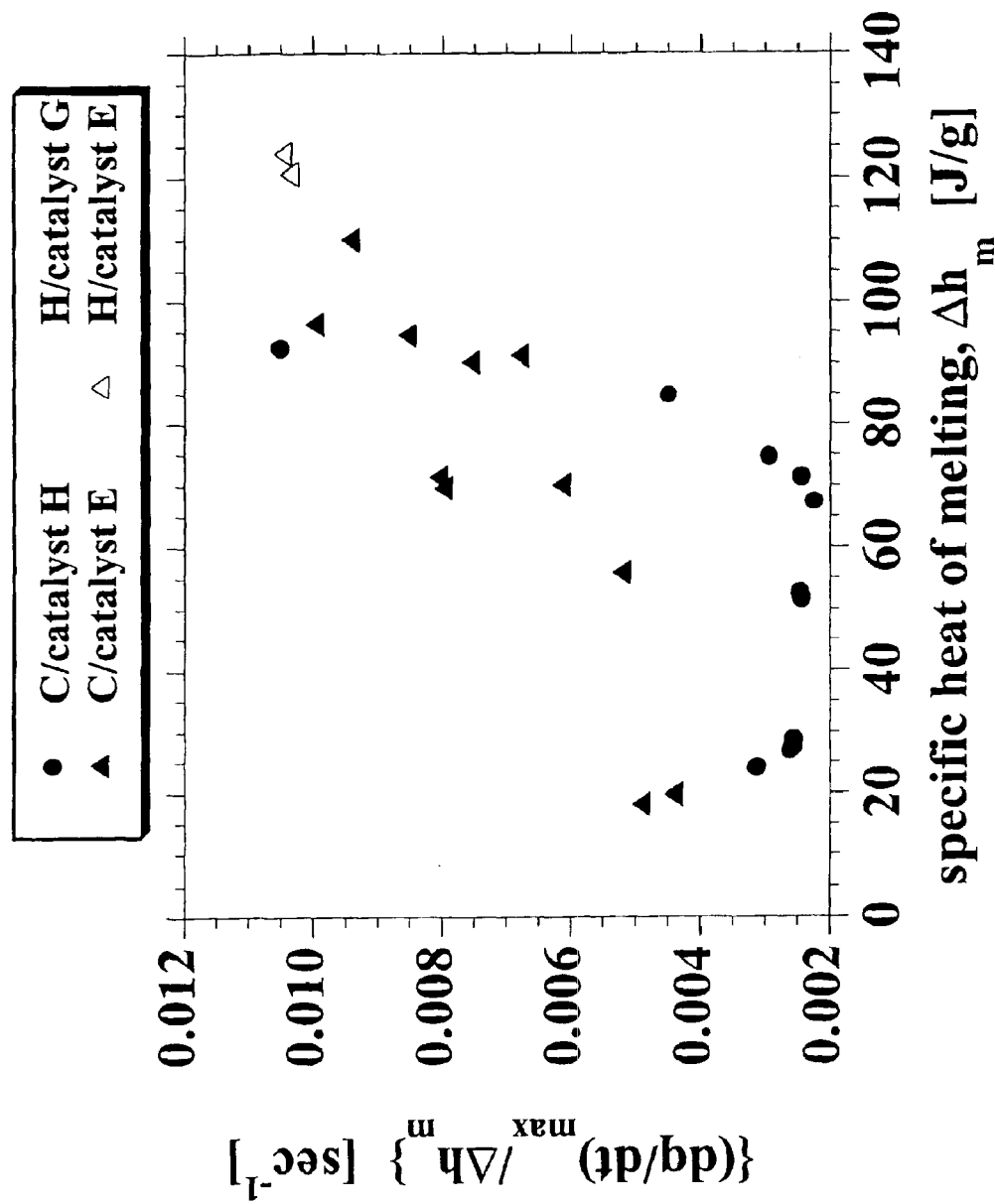
FIG. 28 shows the maximum heat flow normalized by the heat of melting as a function of the heat of melting for various samples of Example 18.

FIG. 28, which shows the maximum heat flow normalized by the heat of melting as a function of the heat of melting, further demonstrates the broadening of the melting endotherm. This is because, at equivalent heat of melting, a lower peak value implies that the distribution must be broadened to give the same area. Roughly approximating the shape of these melting curves as a triangle, for which the area is given by the formula one-half times the base times the height, then b1/b2=h2/h1. The inventive copolymers show as much as a four-fold decrease in height, implying a significant increase in breadth.

Figure 29:
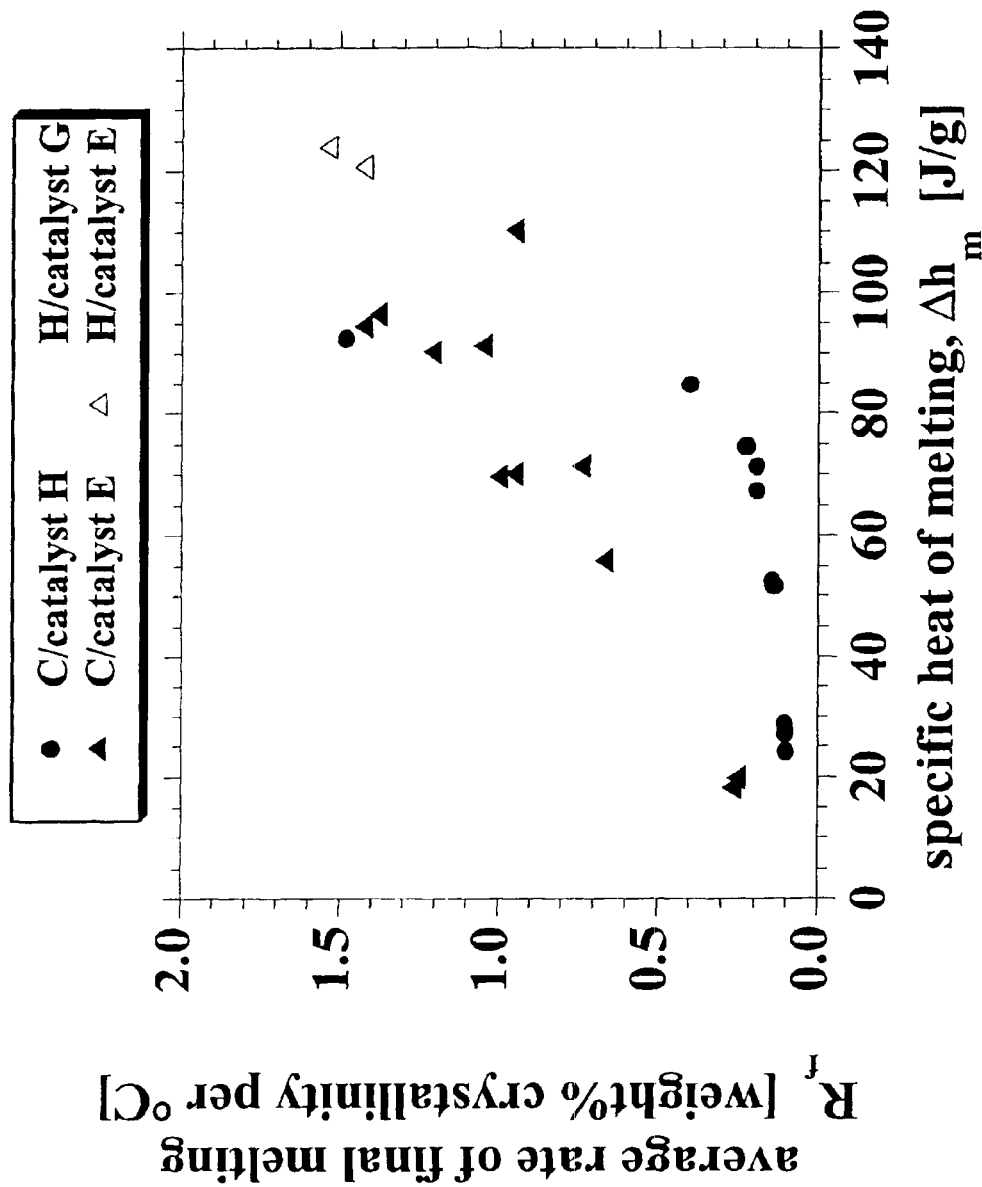
FIG. 29 illustrates that the rate at which the last portion of crystallinity disappears in the inventive polymers is significantly lower than for metallocene polymers.

FIG. 29 illustrates a useful aspect of the broader melting range of the inventive polymers, namely that the rate at which the last portion of crystallinity disappears (units: weight % crystallinity per° C.) is significantly lower than for metallocene polymers.

The data in Table 18-2 demonstrate in practical terms the utility of this broadening of the melting endotherm. Entries in Table 18-2 illustrate: (1) the extent to which a greater fraction of melting occurs at lower temperatures, which is important for heat seal and bonding applications, and which is greater for the inventive copolymers; and (2) the extent to which crystallinity remains at higher temperatures and the rate at which the final portion of crystallinity disappears, which can be important for fabrication operations such as thermoforming, foaming, blow molding, and the like, both of which are greater for the inventive copolymers.

TABLE 18-1

Melting Results from DSC

| Sample* | ethylene (mole %) | $\Delta h_m$ (J/g) | $T_{max}$ (° C.) | $T_1$ (° C.) | $(dq/dt)_{max}/\Delta h_m$ (sec$^{-1}$) | $V_1$ (° C.$^2$) | $T_{1\%c}$ (° C.) | $R_f$ (**) |
|---|---|---|---|---|---|---|---|---|
| 18-1-1 | 0.0 | 90.4 | 139.0 | 123.5 | 0.0109 | 416 | 143.0 | 1.60 |
| 18-1-2 | 0.0 | 94.3 | 138.8 | 122.2 | 0.0105 | 505 | 143.1 | 1.54 |
| 18-1-3 | 0.0 | 94.0 | 139.4 | 122.4 | 0.0105 | 505 | 143.3 | 1.60 |
| 18-1-4 | 0.0 | 95.9 | 139.5 | 121.4 | 0.0102 | 576 | 143.4 | 1.60 |
| 18-1-5 | 1.5 | 92.4 | 138.2 | 118.4 | 0.0105 | 630 | 142.0 | 1.48 |
| 18-1-6 | 4.3 | 85.0 | 120.7 | 99.2 | 0.0045 | 716 | 135.0 | 0.40 |
| 18-1-7 | 8.2 | 67.5 | 85.9 | 83.8 | 0.0023 | 909 | 139.7 | 0.19 |
| 18-1-8 | 8.2 | 71.2 | 93.0 | 84.4 | 0.0025 | 835 | 137.5 | 0.19 |
| 18-1-9 | 8.2 | 74.6 | 108.2 | 87.0 | 0.0029 | 790 | 134.6 | 0.23 |
| 18-1-10 | 11.8 | 51.6 | 71.7 | 69.3 | 0.0024 | 790 | 124.4 | 0.14 |
| 18-1-11 | 11.8 | 52.5 | 74.8 | 69.4 | 0.0025 | 781 | 123.7 | 0.14 |
| 18-1-12 | 11.8 | 51.9 | 73.9 | 69.4 | 0.0025 | 802 | 124.3 | 0.14 |
| 18-1-13 | 15.8 | 24.0 | 55.2 | 66.7 | 0.0031 | 667 | 112.0 | 0.10 |
| 18-1-14 | 15.8 | 28.7 | 55.2 | 66.3 | 0.0026 | 795 | 118.0 | 0.10 |
| 18-1-15 | 15.8 | 27.6 | 55.6 | 66.0 | 0.0026 | 783 | 116.4 | 0.10 |
| 18-1-16 | 15.8 | 26.9 | 55.2 | 66.4 | 0.0026 | 769 | 115.7 | 0.10 |
| 18-1-17a | 0.0 | 120.7 | 160.3 | 145.3 | 0.0104 | 457 | 165.9 | 1.43 |
| 18-1-17b | 0.0 | 123.9 | 159.8 | 144.5 | 0.0105 | 486 | 165.2 | 1.54 |
| 18-1-18 | . . . | 90.3 | 140.6 | 125.0 | 0.0076 | 419 | 146.1 | 1.21 |
| 18-1-19 | . . . | 91.3 | 139.0 | 123.9 | 0.0068 | 374 | 145.5 | 1.05 |

TABLE 18-1-continued

Melting Results from DSC

| Sample* | ethylene (mole %) | $\Delta h_m$ (J/g) | $T_{max}$ (° C.) | $T_1$ (° C.) | $(dq/dt)_{max}/\Delta h_m$ (sec$^{-1}$) | $V_1$ (° C.$^2$) | $T_{1\%c}$ (° C.) | $R_f$ (**) |
|---|---|---|---|---|---|---|---|---|
| 18-1-20a | 4.2 | 110.2 | 137.7 | 121.8 | 0.0094 | 337 | 144.3 | 0.95 |
| 18-1-20b | 4.2 | 96.5 | 137.9 | 121.1 | 0.0100 | 451 | 142.7 | 1.38 |
| 18-1-21 | ... | 94.6 | 136.7 | 120.3 | 0.0086 | 385 | 140.5 | 1.43 |
| 18-1-22a | 8.0 | 71.4 | 117.5 | 105.8 | 0.0081 | 197 | 124.8 | 0.74 |
| 18-1-22b | 8.0 | 69.7 | 117.0 | 103.4 | 0.0080 | 271 | 122.8 | 1.00 |
| 18-1-23 | ... | 70.1 | 110.3 | 91.0 | 0.0062 | 512 | 115.9 | 0.95 |
| 18-1-24 | ... | 55.9 | 97.0 | 78.7 | 0.0052 | 436 | 103.9 | 0.67 |
| 18-1-25 | ... | 19.8 | 63.0 | 61.1 | 0.0044 | 188 | 80.1 | 0.25 |
| 18-1-26 | ... | 18.2 | 56.6 | 58.8 | 0.0049 | 158 | 75.3 | 0.27 |

*Samples 18-1-1 to −4 made with catalyst G, samples −5 to −16 with catalyst H, and −17 to −24 with catalyst E.
**Units for $R_f$: weight % crystallinity per ° C.

TABLE 18-2

Broadening of the Melting Endotherm

| Sample | starting crystallinity (weight %) | Fraction Melted at $T_1 - 30°$ C. | fraction Melted at $T_1 - 20°$ C. | Fraction Remaining at $T_1 + 20°$ C. | fraction remaining at $T_1 + 30°$ C. |
|---|---|---|---|---|---|
| 18-2-8 (inventive) | 43.2 | 0.153 | 0.229 | 0.249 | 0.134 |
| 18-2-22a (comparative) | 43.3 | 0.040 | 0.112 | 0.019 | 0.004 |
| 18-2-11 (inventive) | 31.8 | 0.143 | 0.235 | 0.221 | 0.131 |
| 18-2-25 (comparative) | 33.9 | 0.103 | 0.170 | 0.127 | 0.009 |

EXAMPLE 19

The data of Table 19-1 shows that at the same level of haze (about 11%), the inventive P/E* polymer (19-1-1) has an equivalent modulus to a comparable metallocene catalyzed propylene/octene/ethylene terpolymer (P/O/E) polymer, with somewhat better toughness.

The data of Table 19-1 also shows that at the same level of haze (about 11%), the inventive P/E* polymer is about nine times more flexible and is much tougher (about 40 C. higher ductile brittle transition temperature (DBTT)) than a Ziegler-Natta catalyzed P/E.

The data of Table 19-2 shows that the inventive P/E* polymers exhibit a wide TMA range of 147–55 C., with an expected lowering of the TMA in response to an increasing ethylene content, and a similar TMA to ethylene-octene polymer (AFFINITY EG8100 shown in Table 19-3) at equivalent crystallinity. In this table, "crystallinity from density" was determined as follows:

$$Crystallinity\ from density = \left(\frac{0.936}{sample density}\right) \times \left(\frac{sample density - 0.853}{0.083}\right) \times 100$$

The data of Table 19-2 also shows not only that the inventive P/E* polymers exhibit a wide flexural modulus range, i.e., 1.6 to 195 kpsi, based on their respective ethylene contents, but also a higher modulus than ethylene-octene polymer (AFFINITY EG8100 shown in Table 19-3) at equivalent crystallinity.

TABLE 19-1

Comparative Injection Molded Properties of Various P/E Polymers

| Number | Description | Ethylene (mol %) | MFR (g/10 min) | Haze (%) | Flex. Mod. (1% sec., kpsi) | DBTT (° C., Dyn.) | Tm (° C.) |
|---|---|---|---|---|---|---|---|
| 19-1-1 | P/E* via Catalyst H | 11.8 | 2.2 | 11.6 | 19.5 | −20 | 121 |
| 19-1-2 | P/O/E via Catalyst E | 7.8 O + 1.3 E | 1.1 | 10.8 | 20 | −13 | 80 |
| 19-1-3 | Basell Profax SR256M | 4.4 | 2.0 | 11.3 | 169 | 20 | 150 |

19-1-2 is a Propylene-Octene-Ethylene copolymer prepared in solution via Catalyst H, containing 7.8 mol % octene and 1.3 mol % ethylene, with an MFR of 1.1 g/10 min.

TABLE 19-2

Comparative Injection Molding Properties of Various P/E and E/O Polymers

| Number | Description | Ethylene (mol %) | Cryst. (%) From density | Flex. Mod. (1% sec., kpsi) | TMA (° C., 1 mm) |
|---|---|---|---|---|---|
| 19-2-1 | HPP via Catalyst H | 0.0 | 61.4 | 195 | 147 |
| 19-2-2 | P/E* via Catalyst H | 8.2 | 40.8 | 48 | 106 |
| 19-2-3 | P/E* via Catalyst H | 11.8 | 27.2 | 19.5 | 87 |
| 19-2-4 | P/E* via Catalyst H | 15.8 | 15.4 | 5.6 | 70 |
| 19-2-5 | P/E* via Catalyst H | 18.6 | 6.7 | 1.6 | 55 |

TMA, "thermal mechanical analysis", is the upper service temperature determined from a thermal mechanical analyzer (Perkin-Elmer TMA 7 series) scanned at 5 C./min and a load of 1 Newton, and defined as the temperature at which the probe penetrates 1 mm into the sample.

TABLE 19-3

Comparative Injection Molding TMA Properties of Various P/E and E/O Polymers

| Number | Description | Ethylene (mol %) | Cryst. (%) From density | Flex. Mod. (1% sec., kpsi) | TMA (° C., 1 mm) |
|---|---|---|---|---|---|
| 19-3-1 | P/E* via Catalyst H | 15.8 | 15.4 | 5.6 | 70 |
| 19-3-2 | AFFINITY EG8100 | 82.9 | 11.9 | 2.4 | 68 |

EXAMPLE 20

The inventive polypropylenes reported in Table 20-1 were made according to the teachings of the present invention in a continuous solution process. These polymers were fed into a Killion blown film line available from Killion Extruders INC. under model designation KN-125. During the film blowing, the Killion line was equipped with a 1.5 inch (3.81 cm) diameter screw, 3 inch (7.62 cm) die diameter, and a 70 mil (1778 micron) die gap. The extruder is 50 inch (125 cm) long with a length to diameter ratio (L/D) of 30. The melt temperature was about 425 F. (218.2 C.) with a blow-up ratio (BUR) of 2.0 and an output rate of 10 lb/h.

The resulting films were 2.0 mil (50 micron) in thickness and film properties were measured according to the standard ASTM methods reported in Table 20-2.

For comparison, various commercially or experimentally available Ziegler-Natta catalyzed polypropylene resins, also reported in Table 20-1, were also fabricated with the Killion line under operating parameters similar to those used for the inventive polymers. Film properties were also measured according to the standard ASTM methods reportred in Table 20-2.

Film properties for all above films are shown in Table 20-3 and the haze, CD and MD-tear (cross and machine direction, respectively), gloss 45 and dart data are plotted in FIGS. 16–18 and 30–31. These Figures clearly demonstrate that films made by the polypropylene of this invention have better haze, CD and MD-tear, gloss-45 and dart properties than existing Ziegler-Natta polypropylene with similar comonomer content. Moreover, the hot tack and heat sealing properties of the films were measured, and the results are reported in FIGS. 19 and 20, respectively. Here too, the polymers of this invention exhibited superior properties to those of a Z-N catalyzed propylene/ethylene copolymer (even though the Z-N copolymer contained a larger amount of ethylene).

In an alternative embodiment of this invention, a commercially available Ziegler-Natta polypropylene, namely H308-02Z produced by the Dow Chemical Company, was used as based resin for a blending study. Various inventive polypropylenes and commercially/experimentally available polypropylene resins were dry blended with the Z-N catalyzed polypropylene with a weight ratio of 70/30 for Z-N polypropylenes. The above dry blended materials were fed into the Killion line, as described above, to produce blown films and the film properties were measured as described above.

Film properties for these blended films are reported in Table 20-4 and FIGS. 32–36. As can be seen from this data, the films made by blending 30% of inventive polypropylene with 70% of the commercial Z-N polypropylene have much better properties than similar films made by blending other Z-N polypropylenes with the H308-02Z.

TABLE 20-1

Resins

| Resins | MFR | co-monomer type | Co-monomer % | Manufacture/Trade name |
|---|---|---|---|---|
| 20-1-1 | 2 | | 0 | |
| 20-1-2 | 2 | Ethylene | 3 | Inventive copolymer |
| 20-1-3 | 2 | Ethylene | 5 | Inventive copolymer |
| 20-1-4 | 2 | Ethylene | 8 | Inventive copolymer |
| 20-1-5 | 2 | Ethylene | 11 | Inventive copolymer |
| 20-1-6 | 2 | Ethylene | 0.5 | Dow, PP, H308-02Z |
| 20-1-7 | 2 | Ethylene | 3 | Basell, PP, SR256M |
| 20-1-8 | 7 | Ethylene | 5.5 | Dow, PP, DS6082, propylene-butene copolymer |
| 20-1-9 | 2 | Ethylene | 3 | Dow, PP, 6D69 |
| 20-1-10 | 5 | 1-Butene | 12 | Dow, PP* |

TABLE 20-2

Test

| Test | Methods |
|---|---|
| Dart-A | ASTM D-1709 |
| Elmendorf Tear-B | ASTM D1922 |
| Haze | ASTM D1003 |
| Tensile, | ASTM D822 |
| Gloss-45 degree | ASTM D2457 |
| MFR | ASTM 1238 |
| Heat Seal | DOW* |
| Hot tack | DOW** |

*The term "Heat seal" is used as an expression for the strength of the heat seal after they have been allowed to cool. It should be pointed out that heat seal samples are conditioned in the laboratory for twenty four hours before they are tested on the Instron. Film samples size is 1 inch wide by 12.5 inch long for testing. The sealing time is 0.5 seconds, sealing pressure is 0.275 N/mm$^2$, the delay time is 0.1 second, the peel speed is 200 mm/second and the seal bars are 5 mm wide.
The seal temperature varies based upon polymer properties. Usually, 5 samples are tested.
**The term "Hot Tack" is used as an expression for the strength of the heat seals immediately after the sealing operating and before the seal has had a chance to cool. All testing procedures for hot tack is similar to that of heat seal except it is tested right after films have been sealed.

TABLE 20-3

File Property Comparison of Neat PP Resins

| Resin/properties | Wt % comonomer | MD-tear, g | CD-tear, g | Dart, g | Haze, % | Gloss-45 |
|---|---|---|---|---|---|---|
| 20-1-1 | 0 | 13 | 25 | 60 | 28 | 30 |
| 20-1-2 | 3 | 16 | 52 | 60 | 5.5 | 75 |
| 20-1-3 | 5 | 290 | 1063 | 640 | 5 | 74 |
| 20-1-4 | 8 | 740 | 1327 | 756 | 2 | 88 |
| 20-1-6 | 0.5 | 14 | 46 | 60 | 34 | 23 |
| 20-1-7 | 3 | 19 | 56 | 60 | | |
| 20-1-8 | 3.2 | | | | | |
| 20-1-9 | 5.5 | 23 | 43 | 68 | 10 | 68 |
| 20-1-10 | 12 | 23 | 43 | 68 | 10 | 68 |

TABLE 20-4

Comparison of Film Properties of Blended PP Resins

| Resin/properties | MD-tear, g | CD-tear, g | Dart, g | CD-elongation, % | CD-Ultimate, psi |
|---|---|---|---|---|---|
| (70/30) Sample 20-1-6/Sample 20-1-4 | 36 | 75 | 89 | 843 | 6212 |
| (70/30) Sample 20-1-6/Sample 20-1-5 | 50 | 243 | 117 | 805 | 6015 |
| (70/30) Sample 20-1-6/Dow PP SRD4190 | 16 | 56 | 60 | 10 | 4672 |
| (70/30) Sample 20-1-6/Sample 20-1-8 | 17 | 47 | 60 | 10 | 4580 |

EXAMPLE 21

Table 21 reports the details behind FIGS. 13–16. All these samples were made by a solution polymerization process. Homopolymer samples 21-1 and 21-12 were made with catalysts E and G, respectively. Comparative metallocene propylene/ethylene copolymer samples 21-2 through 21-11 were made with catalyst E. Non-metallocene propylene/ethylene copolymer samples 21-13 through 21-16 were made with catalyst H. Mole % ethylene was determined by $^{13}$C-NMR. $T_{max}$ was determined by DSC, second heating scan at 10° C./min. Flexural modulus values in Table 21 are either from: (a) direct measurement on injection molded specimens by ASTM D790 (samples marked by asterisks); or (b) measurement of tensile modulus on compression molded microtensile specimens by ASTM D638 then use of established correlations between tensile and flexural moduli to estimate the flexural modulus; or (c) estimation of flexural modulus from correlations of flexural modulus to heat of fusion by DSC. Haze was measured on 10 mil thick compression molded films by ASTM D1003 using Model XC211 Haze-Gard System manufactured by Pacific Scientific, Gardner/Neotec Instrument Division. Films for haze measurements were compression molded at 200° C. with six minute preheat at low pressure plus four minute molding at about 200 psi pressure, followed by ten minute cooling to 30° C. at 200 psi pressure. Mylar film was used as backing in contact with the polymer in order to obtain films with minimal surface haze. After molding, films or other specimens were aged two weeks or longer at room temperature prior to mechanical testing or haze testing.

TABLE 21

Data for FIGS. 13–16

| Sample | Mole % E | $T_{max}$ (° C.) | $E_{flex}$ (ksi) | % Haze |
|---|---|---|---|---|
| 21-1* | 0 | 154 | 216 | 49.5 |
| 21-2 | 2.6 | 147 | 183 | 31.2 |
| 21-3 | 3.4 | 142 | 163 | 29.1 |
| 21-4 | 5.1 | 132 | 122 | 30.0 |
| 21-5 | 5.5 | 131 | 118 | 30.4 |
| 21-6* | 6.5 | 120 | 91 | 30.8 |
| 21-7* | 7.2 | 120 | 83 | 34.2 |
| 21-8 | 9.8 | 113 | 63 | 30.6 |
| 21-9 | 12.3 | 94 | 26 | 24.4 |
| 21-10 | 14.6 | 81 | 14 | 20.6 |
| 21-11 | 17.4 | 66 | 12 | 21.3 |
| 21-12* | 0 | 144 | 195 | 33.3 |
| 21-13 | 8.2 | 104 | 57 | 27.0 |
| 21-14* | 11.8 | 68 | 20 | 22.3 |
| 21-15* | 15.8 | 54 | 5.6 | 14.0 |
| 21-16* | 18.6 | 39 | 1.6 | 13.2 |

EXAMPLE 22

Figure 15:
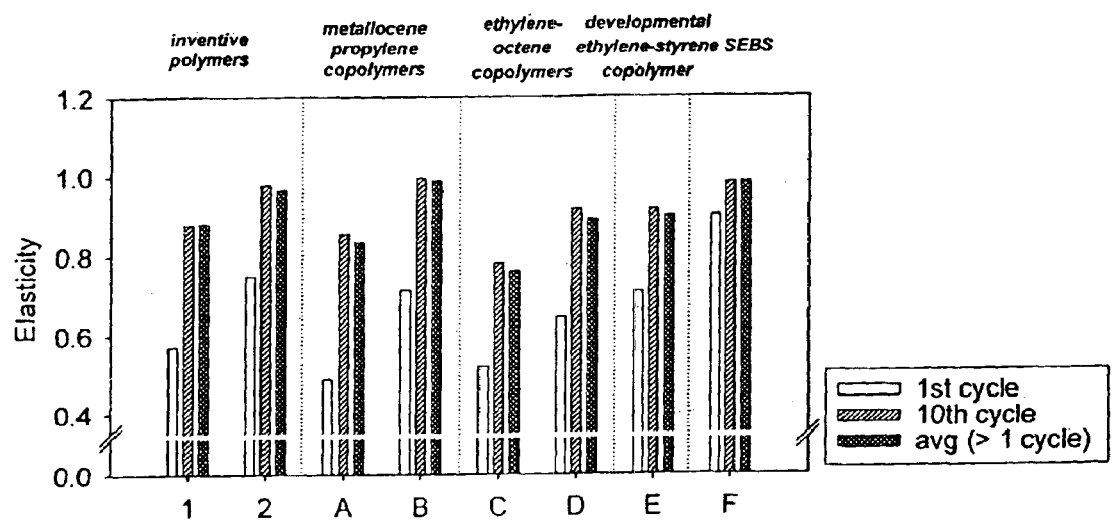
FIG. 15 is a bar graph comparing the elasticity of pre-stretched P/E* copolymers of this invention against various conventional pre-stretched thermoplastic elastomers.

FIGS. 14 and 15 report certain elasticity data for the polymers of this invention and certain comparative polymers. Table 22-1 describes the elastomers.

The test samples were compression molded specimens. Polymer in pellet form was compression molded at 190 C. into 1.5 mm thick sheets. The sheets were cooled by placing each between two platens at 25 C. under light pressure. The specimens were allowed to age for at least seven days at ambient conditions before testing.

Tensile "dog bones" were punched out of the sheets using a knife shaped according to ASTM D-1708. The first melting behavior was measured by cutting out a 5 to 10 mg piece of the aged specimen. The specimen was loaded into an aluminum pan and analyzed in a differential scanning calorimeter manufactured by TA Instruments Incorporated. Heating spanned −50 to 230 C. at 10 C./min.

The specimens were tested in uniaxial tension with a mechanical test device (Instron Corp.) fitted with pneumatic grips. The engineering strain rate was 400% per minute. Both strain to break and multicycle loading strain histories were used. In the case of multicycle loading, specimens were loaded and unloaded to various strains (100 to 900%) for up to 10 cycles. No pause was used between successive cycles.

Table 22-2 reports the data in FIGS. 14 and 15. The data in Table 22-2 reports elasticity versus crystallinity for the same group of elastomers. Crystallinity is an important property in elastomeric applications because it controls to a large extent the stiffness (i.e., modulus) of a material. The virgin or unstretched metallocene polypropylenes exhibit elasticity versus crystallinity similar to the homogeneous polyethylene and ethylene-stryene elastomers, while the elastomeric polymers of this invention exhibit higher elasticity at the same crystallinity. Even after pre-stretching, the elastomeric polymers of this invention continue to exhibit superior elasticity at the same crystallinity as compared to both the metallocene propylenes and the homogeneous polyethylene and ethylene-stryene elastomers. The polymers of this invention demonstrate similar elasticity after stretching as do commercial grade SEBS polymers, e.g., Krayton G-1657.

TABLE 22-1

Elastomers

| Polymer samples | Description | Copolymer (wt. %) | (mol %) | DSC Crystallinity (wt. %) |
|---|---|---|---|---|
| 1 | inventive polymer | 11 | 16 | 18 |
| 2 | inventive polymer | 13 | 19 | 10 |
| A | metallocene propylene-ethylene copolymer | — | — | 21 |
| B | metallocene propylene-ethylene copolymer | — | — | 4 |
| C | developmental ethylene-octene copolymer5 | 41 | 15 | 14 |
| D | Affinity EG8100 | 35 | 12 | 6 |
| E | developmental ethylene-styrene copolymer | 41 | 16 | 5 |
| F | Kraton G-1657 (SEBS) | — | — | — |

TABLE 22-2

Elasticity Values of the Data in FIGS. 14 and 15

| Polymer | virgin 1st cycle | pre-stretched 10th cycle | average (>1 cycle) |
|---|---|---|---|
| 1 | 0.57 | 0.88 | 0.88 |
| 2 | 0.75 | 0.97 | 0.97 |
| A | 0.49 | 0.85 | 0.83 |
| B | 0.71 | 0.99 | 0.99 |
| C | 0.52 | 0.78 | 0.76 |
| D | 0.64 | 0.92 | 0.89 |
| E | 0.71 | 0.92 | 0.90 |
| F | 0.90 | 0.98 | 0.99 |

EXAMPLE 23

This example demonstrates the use of a continuous 2-reactor solution process in series wherein a higher modulus polypropylene is produced in the first reactor, a lower modulus propylene/ethylene copolymer is prepared in series in a second reactor, and the solvent and unreacted monomers are recycled to the reactors. The catalyst for this example is Catalyst J. Catalyst J can be made in an analogous manner to Catalyst H, excepting that 2-methyl-bromobenzene is used instead of 9-bromophenanthrene.

Purified ISOPAR-E solvent, ethylene, hydrogen, and 1-octene are supplied to a 1 gallon jacketed reactor equipped with a jacket for temperature control and an internal thermocouple. The solvent feed to the reactor is measured by a mass-flow controller. A variable speed diaphragm pump controls the solvent flow rate and increases the solvent pressure to the reactor. The compressed, liquified propylene feed is measured by a mass flow meter and the flow is controlled by a variable speed diaphragm pump. At the discharge of the pump, a side stream is taken to provide flush flows for the catalyst injection line and the reactor agitator. The remaining solvent is combined with ethylene and hydrogen and delivered to the reactor. The ethylene stream is measured with a mass flow meter and controlled with a Research Control valve. A mass flow controller is used to deliver hydrogen into the ethylene stream at the outlet of the ethylene control valve. The temperature of the solvent/monomer is controlled by use of a heat exchanger before entering the reactor. This stream enters the bottom of the reactor. The catalyst component solutions are metered using pumps and mass flow meters, and are combined with the catalyst flush solvent. This stream enters the bottom of the reactor, but in a different port than the monomer stream. The reactor is run liquid-full at 500 psig with vigorous stirring. The process flow is in from the bottom and out of the top. All exit lines from the reactor are steam traced and insulated. The exit of the first reactor is connected by insulated piping to a second 6 gallon reactor similarly equipped to the first, with a provision for independent catalyst and cocatalyst addition, and additional monomer, hydrogen, solvent addition and jacket temperature control. After the polymer solution stream exits the second reactor, polymerization is stopped with the addition of a small amount of water, and other additives and stabilizers can be added at this point. The stream flows through a static mixer and a heat exchanger in order to heat the solvent/polymer mixture. The solvent and unreacted monomers are removed at reduced pressure, and the product is recovered by extrusion using a devolatilizing extruder. The solvent and unreacted monomers are condensed and recovered into a storage tank, from which they can be pumped (optionally with the addition of fresh solvent, propylene, and/or other monomers) back to the first and/or the second reactor. The extruded strand is cooled under water and chopped into pellets. The operation of the dual-reactor system is controlled with a process control computer.

A 4 L catalyst tank is filled with an ISOPAR E solution of Catalyst J at a concentration of 50 ppm Hf. Additional tanks are provided with a solution of N,N-dioctadecylanilinium tetrakis(pentafluorophenyl)borate in ISOPAR E at a concentration of 100 ppm B, and MMAO-3A in ISOPAR E at a concentration of 100 ppm Al. ISOPAR E is continuously fed into the first reactor, along with propylene. The Catalyst J solution, along with enough N,N-dioctadecylanilinium tetrakis(pentafluorophenyl)borate in ISOPAR E and MMAO-3A in ISOPAR E to maintain a Hf:B:Al molar ratio of 1:1.2:5 is added to the first reactor. The solvent and propylene feed rate, as well as the jacket temperature and catalyst feed rate are adjusted to produce 1.5 pounds per hour of a propylene polymer having a melting point >140 degrees C. The flow rate of Catalyst J is adjusted to maintain a first-reactor product melt flow rate (MFR) of 2.0, while maintaining 50% propylene conversion at 16 weight % polymer in solution and a reactor temperature of 100 degrees C. by adjusting the temperature of the reactor jacket, the feed temperature and through the addition of hydrogen as a molecular weight control agent. The molar ratio of aluminum can be adjusted in order to optimize the overall catalyst efficiency. The contents of the first reactor flow into the second reactor, where additional solvent and a mixture of propylene and ethylene is added at a feed temperature of 5 degrees C. The Catalyst J solution, along with enough N,N-dioctadecylanilinium tetrakis(pentafluorophenyl) borate in ISOPAR E and MMAO-3A in ISOPAR E to maintain a Hf:B:Al molar ratio of 1:1.2:5 is added to the second reactor at a rate sufficient to maintain a 65% propylene conversion and a reaction temperature of 110° C., with an overall production rate (the combination of the product of reactor 1 and reactor 2) of 5 pounds per hour. The ethylene feed rate is adjusted to produce a second reactor product that is 8 weight % ethylene. This corresponds to a reactor split of 30% (1.5 pounds/hr from the first reactor out of 5 pounds/hr overall). The flow rate of Catalyst J is adjusted to maintain an overall product melt flow rate (MFR) of 2.0 by adjusting the temperature of the reactor jacket and through the addition of hydrogen as a molecular weight control agent. The ethylene conversion into polymer is >96%. The molar ratio of aluminum can be adjusted in order to optimize the overall catalyst efficiency. After the post-reactor deactivation of the catalyst, antioxidant is added, and the product is devolatilized and extruded to recover the solid product. The solvent and unreacted monomers, which contain very low levels of unreacted ethylene, are condensed, recovered, and can be pumped back into reactor 1 and reactor 2 in a continuous process. Because most of the ethylene is consumed in the second reactor, very little is recycled to the first reactor and the melting point and modulus of the polymer produced there is relatively high. The product, which is a solution blend of 30 weight % high melting polypropylene (containing trace amounts of ethylene) having a 2 MFR and 70 weight % of a 9 weight % ethylene/propylene copolymer, with the overall product having a 2 MFR. This product is useful in a variety of applications, including BOPP (biaxially-oriented polypropylene) sealants and films.

EXAMPLE 24

The procedure of Example 23 is followed, except that the first reactor is used to produce a copolymer of ethylene and propylene, and the second reactor is used to produce a lower melting copolymer of propylene and ethylene. For this example, the general procedure of Example A is followed except that the feeds are adjusted so that the first reactor produces 1.5 pounds/hr of a copolymer of propylene with 2 weight % ethylene, having an MFR of 2. The first reactor temperature is 90 degrees C. and the first reactor propylene conversion is 65%. At this propylene conversion, the ethylene conversion can be >98%. The contents of the first reactor, along with fresh catalyst and fresh propylene in additional solvent at 5° C. passes into the second reactor. Additional ethylene is added to the second reactor in order to produce a 8 weight % ethylene copolymer in the second reactor at a reactor temperature of 110° C., with a 30% reactor split and an overall isolated product of 2 MFR. This product is particularly useful for BOPP.

EXAMPLE 25

The procedure of Example 23 is followed, except that the first reactor is used to produce a high molecular weight copolymer of ethylene and propylene, and the second reactor is used to produce a high melting polymer of propylene of lower molecular weight. For this example, the general procedure of Example 23 is followed except that the feeds are adjusted so that the first reactor produces 1.5 pounds per hour of a copolymer of propylene with 8 weight % ethylene, having an MFR of 0.1. The first reactor temperature is 90° C. and the first reactor propylene conversion is 65%. At this propylene conversion, the ethylene conversion can be >98%. The contents of the first reactor, along with fresh catalyst and fresh propylene in additional solvent at 5° C. passes into the second reactor. The feeds to the second reactor are adjusted in order to produce a high melting propylene polymer in the second reactor at a reactor temperature of 110° C., with a 30% reactor split and an overall isolated product of 2 MFR. This product is particularly useful for thermoforming and extrusion blowmolding.

EXAMPLE 26

For this example, the general procedure of Example 25 is followed except that the feeds are adjusted so that the first reactor produces 1.5 pounds/hr of a copolymer of propylene with 13 weight % ethylene, having an MFR of 0.1. The first reactor temperature is 90° C. and the first reactor propylene conversion is 65%. At this propylene conversion, the ethylene conversion can be >98%. The contents of the first reactor, along with fresh catalyst and fresh propylene in additional solvent at 5° C. passes into the second reactor. The feeds to the second reactor are adjusted in order to produce a high melting propylene polymer in the second reactor at a reactor temperature of 110° C., with a 30% reactor split and an overall isolated product of 2 MFR. This product is particularly useful for thermoforming and extrusion blowmolding.

EXAMPLE 27

For this example, the general procedure of Example 25 is followed except that the feeds are adjusted so that the first reactor produces a copolymer of propylene with 13 weight % ethylene, having an MFR of 25. The first reactor temperature is 90° C. and the first reactor propylene conversion is 65%. At this propylene conversion, the ethylene conversion can be >98%. The contents of the first reactor, along with fresh catalyst and fresh propylene in additional solvent at 5° C. passes into the second reactor. The feeds to the second reactor are adjusted in order to produce a high melting propylene polymer in the second reactor at a reactor temperature of 110 degrees C., with a 30% reactor split and an overall isolated product of 25 MFR. This product is particularly useful for producing fibers.

EXAMPLE 28

The general procedure of Example 23 is followed except that the feeds are adjusted so that the first reactor produces a high melting propylene polymer having an MFR of 25. The first reactor temperature is 90° C. and the first reactor propylene conversion is 55%. The contents of the first reactor, along with fresh catalyst and fresh propylene and ethylene in additional solvent at 5° C. passes into the second reactor. The feeds to the second reactor are adjusted in order to produce a propylene/ethylene copolymer polymer in the second reactor at a reactor temperature of 110° C., with a 30% reactor split and an overall isolated product of 25 MFR. This product is particularly useful for producing fibers.

Although the invention has been described in considerable detail, this detail is for the purpose of illustration. Many variations and modifications can be made on the invention as described above without departing from the spirit and scope of the invention as described in the appended claims. All publications identified above, specifically including all U.S. patents and allowed U.S. patent applications, are incorporated in their entirety herein by reference.

What is claimed is:

1. A propylene/ethylene copolymer comprising at least about 60 weight percent of units derived from propylene and at least about 0.1 weight percent of units derived from ethylene, the copolymer characterized as having $^{13}$C NMR peaks corresponding to a regio-error at about 14.6 and about 15.7 ppm, the peaks of about equal intensity.

2. The copolymer of claim 1 further characterized as having a skewness index, $S_{ix}$, greater than about −1.20.

3. The copolymer of claim 1 further characterized as having a DSC curve with a $T_{me}$ that remains essentially the same and a $T_{max}$ that decreases as the amount of ethylene in the copolymer is increased.

4. The copolymer of claim 1 further characterized as having an X-ray diffraction pattern exhibiting more gamma-form crystals than a propylene/ethylene copolymer comparable in weight average molecular weight except that it is prepared with a Ziegler-Natta catalyst.

5. The copolymer of claim 1 further characterized as having a B-value greater than about 1.3 when the ethylene content of the copolymer is at least about 3 weight percent.

6. The copolymer of claim 2 further characterized as having a DSC curve with a $T_{me}$ that remains essentially the same and a $T_{max}$ that decreases as the amount of ethylene in the copolymer is increased.

7. The copolymer of claim 2 further characterized as having an X-ray diffraction pattern exhibiting more gamma-form crystals than a propylene/ethylene copolymer comparable in weight average molecular weight except that it is prepared with a Ziegler-Natta catalyst.

8. The copolymer of claim 2 further characterized as having a B-value greater than about 1.3 when the ethylene content of the copolymer is at least about 3 weight percent.

9. The copolymer of claim 6 further characterized as having an X-ray diffraction pattern exhibiting more gamma-form crystals than a propylene/ethylene copolymer comparable in weight average molecular weight except that it is prepared with a Ziegler-Natta catalyst.

10. The copolymer of claim 6 further characterized as having a B-value greater than about 1.3 when the ethylene content of the copolymer is at least about 3 weight percent.

11. The copolymer of claim 9 further characterized as having a B-value greater than about 1.3 when the ethylene content of the copolymer is at least about 3 weight percent.

12. A process for making the copolymer of claim 1, the process comprising contacting under polymerization conditions propylene and ethylene with a nonmetallocene, metal-centered, heteroaryl ligand catalyst in combination with at least one activator.

13. The process of claim 12 which the metal component of the catalyst is at least one of hafnium and zirconium.

14. The process of claim 13 in which the catalyst comprises a ligand of the general formula:

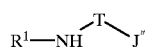

(I)

wherein $R^1$ is characterized by the general formula:

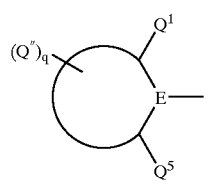

(II)

where $Q^1$ and $Q^5$ are substituents on the ring other than atom E, with E selected from the group consisting of carbon and nitrogen, and with at least one of $Q^1$ or $Q^5$ having at least 2 atoms;

q is 1, 2, 3, 4 or 5;

Q" is selected from the group consisting of hydrogen, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxyl, aryloxyl, silyl, boryl, phosphino, amino, thio, seleno, halide, nitro, and combinations thereof;

T is a bridging group selected from the group consisting of —$CR^2R^3$— and —$SiR^2R^3$— with $R^2$ and $R^3$ independently selected from the group consisting of hydrogen, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxyl, aryloxyl, silyl, boryl, phosphino, amino, thio, seleno, halide, nitro, and combinations thereof; and J" is selected from the group consisting of heteroaryl and substituted heteroaryl.

15. The process of claim 14 conducted under solution polymerization conditions.

16. The process of claim 14 conducted under slurry polymerization conditions.

17. The process of claim 14 conducted under gas phase polymerization conditions.

18. The process of claim 14 in which the unsaturated comonomer is at least one of a $C_{4-20}$ α-olefin, a $C_{4-20}$ diolefin, a $C_{8-40}$ vinyl aromatic compound, and a halogen-substituted $C_{8-40}$ vinyl aromatic compound.

19. The process of claim 18 in which the unsaturated comonomer is a $C_{4-12}$ α-olefin.

20. The process of claim 18 in which the unsaturated comonomer is styrene.

21. The process of claim 14 in which the comonomer is ethylene.

22. A solution phase process for making the copolymer of claim 1, the process comprising contacting propylene and at least one of ethylene and an unsaturated comonomer under solution phase polymerization conditions with a nonmetallocene, metal-centered, heteroaryl ligand catalyst.

23. The process of claim 22 in which the catalyst comprises a ligand of the general formula:

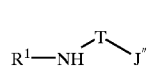

(I)

wherein $R^1$ is characterized by the general formula:

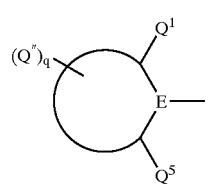

(II)

where $Q^1$ and $Q^5$ are substituents on the ring other than atom E, with E selected from the group consisting of carbon and nitrogen, and with at least one of $Q^1$ or $Q^5$ having at least 2 atoms;

q is 1, 2, 3, 4 or 5;

Q" is selected from the group consisting of hydrogen, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxyl, aryloxyl, silyl, boryl, phosphino, amino, thio, seleno, halide, nitro, and combinations thereof;

T is a bridging group selected from the group consisting of —$CR^2R^3$— and —$SiR^2R^3$— with $R^2$ and $R^3$ independently selected from the group consisting of hydrogen, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxyl, aryloxyl, silyl, boryl, phosphino, amino, thio, seleno, halide, nitro, and combinations thereof; and J" is selected from the group consisting of heteroaryl and substituted heteroaryl.

24. The process of claim 23 in which the metal component of the catalyst is at least one of hafnium and zirconium.

25. A fabricated article made from the copolymer of claim 1.

26. The fabricated article of claim 25 in the form of a film.

27. The fabricated article of claim 25 in the form of a molded article.

28. The fabricated article of claim 25 in the form of a foam.

29. The fabricated article of claim 25 in the form of a sheet.

* * * * *